United States Patent
Fleming et al.

(10) Patent No.: US 9,023,832 B2
(45) Date of Patent: May 5, 2015

(54) DERIVATIVES OF 1-AMINO-2-CYCLOPROPYLETHYLBORONIC ACID

(71) Applicant: Millennium Pharmaceuticals, Inc., Cambridge, MA (US)

(72) Inventors: Paul E. Fleming, Weston, MA (US); Jing Li, Lansdale, PA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 14/189,303

(22) Filed: Feb. 25, 2014

(65) Prior Publication Data

US 2014/0179631 A1  Jun. 26, 2014

Related U.S. Application Data

(63) Continuation of application No. 13/934,989, filed on Jul. 3, 2013, which is a continuation of application No. 13/075,306, filed on Mar. 30, 2011, now Pat. No. 8,513,218.

(60) Provisional application No. 61/319,464, filed on Mar. 31, 2010.

(51) Int. Cl.
  *A61K 31/69* (2006.01)
  *C07F 5/04* (2006.01)
  *C07F 5/02* (2006.01)

(52) U.S. Cl.
  CPC .. *C07F 5/04* (2013.01); *C07F 5/025* (2013.01)

(58) Field of Classification Search
  USPC ......... 514/64; 546/13; 544/69, 229; 548/110, 548/405; 564/8
  See application file for complete search history.

(56) References Cited

U.S. PATENT DOCUMENTS

| | | |
|---|---|---|
| 4,499,082 A | 2/1985 | Shenvi et al. |
| 5,106,948 A | 4/1992 | Kinder et al. |
| 5,159,060 A | 10/1992 | Kinder et al. |
| 5,169,841 A | 12/1992 | Kleeman et al. |
| 5,187,157 A | 2/1993 | Kettner et al. |
| 5,492,900 A | 2/1996 | LaHann |
| 5,574,017 A | 11/1996 | Gutheil |
| 5,580,486 A | 12/1996 | Labeque et al. |
| 5,780,454 A | 7/1998 | Adams et al. |
| 6,060,462 A | 5/2000 | Galemmo, Jr. et al. |
| 6,846,806 B2 | 1/2005 | Priestley |
| 6,939,854 B2 | 9/2005 | Priestley |
| 7,442,830 B1 | 10/2008 | Olhava et al. |
| 8,513,218 B2 * | 8/2013 | Fleming et al. ............ 514/64 |
| 2002/0188100 A1 | 12/2002 | Plamondon et al. |
| 2004/0171556 A1 | 9/2004 | Purandare et al. |
| 2005/0107307 A1 | 5/2005 | Bernadini et al. |
| 2006/0084592 A1 | 4/2006 | Boucher |
| 2010/0081633 A1 | 4/2010 | Fleming et al. |
| 2011/0245203 A1 | 10/2011 | Fleming et al. |
| 2012/0041196 A1 | 2/2012 | Bernardini et al. |

FOREIGN PATENT DOCUMENTS

| | | |
|---|---|---|
| EP | 0092999 A2 | 11/1983 |
| EP | 315574 A2 | 5/1989 |
| EP | 354522 A1 | 2/1990 |
| EP | 1267880 B1 | 12/2005 |
| EP | 2178888 B1 | 7/2012 |
| WO | WO-9613266 A1 | 5/1996 |
| WO | WO-9614857 A1 | 5/1996 |
| WO | WO-98/35691 A1 | 8/1998 |
| WO | WO-9915183 A1 | 4/1999 |
| WO | WO-9930707 A1 | 6/1999 |
| WO | WO-00/57887 A1 | 10/2000 |
| WO | WO-0102424 A2 | 1/2001 |
| WO | WO-02/059130 A1 | 8/2002 |
| WO | WO-02059131 A1 | 8/2002 |
| WO | WO-03033507 A1 | 4/2003 |
| WO | WO-03059898 A2 | 7/2003 |
| WO | WO-2005021558 A2 | 3/2005 |
| WO | WO-2005097809 A2 | 10/2005 |
| WO | WO-2007005991 A1 | 1/2007 |
| WO | WO-2007089618 A2 | 8/2007 |
| WO | WO-2009006473 A2 | 1/2009 |
| WO | WO-2009/020448 A1 | 2/2009 |
| WO | WO-2009/154737 A1 | 12/2009 |
| WO | WO-2010036357 A1 | 4/2010 |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Bartusek, M., et al., "Boron chelates with citrate," Scripta-Chemistry, vol. 21 (1991) pp. 63-67.
Capitulo 28: liofilizacion, Farmacotecnia: teoria y practicatomo 3, 1982, MX, pp. 1038-1041.
Dick, L.R., et al., "Building on bortezomib: second-generation proteasome inhibitors as anti-cancer therapy", Elsevier, Drug Discovery Today, vol. 15, No. 5, Mar. 6, 2010, pp. 243-249.
EP09767050.9 Communication pursuant to Article 94(3) EPC (Examination Report) dated Oct. 25, 2011 from corresponding European patent application 09 767 050.9-2117.
EP1660507 Opposition, May 4, 2010, Opponent's Notice of Opposition, 26 pages.

(Continued)

*Primary Examiner* — Kristin Vajda
(74) *Attorney, Agent, or Firm* — Honigman Miller Schwartz and Cohn LLP; Lucy X. Yang; Jonathan P. O'Brien

(57) ABSTRACT

The present invention provides novel compounds useful as proteasome inhibitors. The invention also provides pharmaceutical compositions comprising the compounds of the invention and methods of using the compositions in the treatment of various diseases.

21 Claims, No Drawings

(56) References Cited

OTHER PUBLICATIONS

EP1660507 Opposition, Jan. 17, 2011, Proprietor's Response to the Notice of Opposition with Amended Claims, 61 pages.
EP1660507 Opposition, Apr. 1, 2011, Summons to Attend Oral Proceedings with Annex, 11 pages.
EP1660507 Opposition, Sep. 7, 2011, Proprietor's Submissions and Amendments, 122 pages.
EP1660507 Opposition, Sep. 19, 2011, Opponent's Reply to Proprietor's Sep. 5, 2011 Submission, 23 pages.
EP1660507 Opposition, Sep. 21, 2011, Proprietor's Letters Regarding Oral Proceedings, 9 pages.
EP1660507 Opposition, Nov. 2, 2011, Oral Proceedings Minutes and Results, 59 pages.
EP1660507 Opposition, Nov. 10, 2011, Opponent's Request for Correction of Minutes of Oral Proceedings, 3 pages.
EP1660507 Opposition, Nov. 29, 2011, Proprietor's Request Regarding Minutes of Oral Proceedings, 3 pages.
EP1660507 Opposition, Dec. 5, 2011, Correction of Minutes of Oral Proceedings, 3 pages.
EP1660507 Opposition, Dec. 7, 2011, Annex to Opposition Letter Dated Nov. 2, 2011, 2 pages.
EP1660507 Opposition, Dec. 7, 2011, Opponent's Letter Further to Proprietor's Representative's Letter Dated Nov. 29, 2011, 3 pages.
EP1660507 Opposition, Dec. 14, 2011, Interlocutory Decision in Opposition Proceedings, 263 pages.
EP1660507 Opposition, Feb. 23, 2012, Opponent's Notice of Appeal Against Decision of the Opposition Division, 5 pages.
EP1660507 Opposition, Feb. 23, 2012, Proprietor's Notice of Appeal Against Decision of the Opposition Division, 2 pages.
EP1660507 Opposition, Apr. 23, 2012, Opponent's Statement of Grounds of Appeal, 38 pages.
EP1660507 Opposition, Apr. 24, 2012, Proprietor's Submissions and Amendments, 189 pages.
EP1660507 Opposition, Sep. 12, 2012, Opponent's Reply to Proprietor's Grounds of Appeal of Apr. 24, 2012, 13 pages.
EP1660507 Opposition, Sep. 12, 2012, Proprietor's Response to Opponent's Grounds of Appeal, 498 pages.
EP1660507 Opposition, Jan. 11, 2013, Proprietor's Submission, 10 pages.
EP2178888 Opposition, Oct. 17, 2011, Summons to Attend Oral Proceedings with Annex, 3 pages.
EP2178888 Opposition, Dec. 30, 2011, Annex to Proprietor's Letter dated Dec. 30, 2011, 3 pages.
EP2178888 Opposition, Dec. 30, 2011, Proprietor's Submission, 3 pages.
EP2178888 Opposition, Apr. 4, 2013, Opponent's Submission, 25 pages.
Gennaro, A.R. (editor), "Remington: The science and practice of pharrnacy," 20th Edition, Chapter 42, Lippincott Williams & Wilkins (publishers), Baltimore, MD (2000) pp. 802-803.
Gray, C.W., "Boronic acid receptors for a-hydroxycarboxylates: high affinity of Shinkai's glucose receptor for tartrate," Journal of Organic Chemistry, vol. 67, No. 15 (2002) pp. 5426-5428.
Houston, T.A., et al., "Boric acid catalyzed chemoselective esterification of a-hydroxycarboxylic acids," Organic Letters, vol. 6, No. 5 (2004) pp. 679-681.
Kataoka, K., et al., "Totally synthetic polymer gels responding to external glucose concentration: their preparation and application to on-off regulation of insulin release," Journal of the American Chemical Society, vol. 120 (1998) pp. 12694-12695.
Kibbe, A.H. (editor), "Handbook of Pharmaceutical Excipients," 3rd Edition, American Pharmaceutical Association (publishers), Washington, D.C. (2000) pp. 324-328.
Korcek, S., et al., "Absolute rate constants for the autoxidation of organometallic compounds. Part II. Benzylboranes and 1-phenylethylboranes," Journal of the Chemical Society, Perkin Transaction 2, (1972) pp. 242-248.
Lieberman, H., et al., "Tablet formulation and design." Pharmaceutical Dosage Forms: tablets vol. 1,1989, US, pp. 91-127.

Lorand, J.P., et al., "Polyol complexes and structure of the benzeneboronate ion," Journal of Organic Chemistry, vol. 24 (1958) pp. 769-774.
Matteson, D.S., et al., "99% Chirally Selective Syntheses via Pinanediol Boronic Esters: Insect Pheromones, Diols, and an Amino Alcohol," Journal of American Chemical Society, vol. 108, No. 4, 1986, pp. 810-819.
Meiland, M., et al., "Seven-membered ring boronates at trans-diol moieties of carbohydrates," Tetrahedron Letters, vol. 50 (2009) pp. 469-472.
Mullard, A., "Next-generation proteasome blockers promise safer cancer therapy", Nature Medicine, vol. 18 No. 1, Jan. 2012, p. 7.
Prasad S., et al., "Studies on the formation of some borocitrates," Journal of the Indian Chemistry Society, vol. 44, No. 3 (1967) pp. 219-220.
Richardson, P.G., et al., "A phase 2 study of bortezomib in relapsed, refractory myeloma," The New England Journal of Medicine, vol. 348, No. 26 (Jun. 26, 2003) pp. 2609-2617.
Ruggeri, B., "The Development and Pharmacology of Proteasome Inhibitors for the Management and Treatment of Cancer," Advances in Pharmacology, vol. 57, 2009, pp. 91-135.
Scheibe, E., "The borocitrates and their preparation," The Pharmaceutical Journal and Transactions, Third Series, No. 542 (Nov. 18, 1880) p. 389.
Snyder, H.R., et al., "Aryl boronic acids, II. Aryl boronic anhydrides and their amine complexes," Journal of the American Chemical Society, vol. 80 (Jul. 20, 1958) pp. 3611-3615.
Stella, V.J., et al., "Development of parenteral formulations of experimental cytotoxic agents. I. Rhizoxin (NSC-332598)," International Journal of Pharmaceutics, vol. 43 (1988) pp. 191-199.
U.S. Appl. No. 13/075,306: Office Action dated May 18, 2012 in pending U.S. Appl. No. 13/075,306, 11 pages.
U.S. Appl. No. 13/249,738: Office Action (made final) Mailed Sep. 7, 2012 in U.S. Appl. No. 13/249,738, 15 pages.
U.S. Appl. No. 13/249,738: Office Action Mailed Mar. 7, 2012 in U.S. Appl. No. 13/249,738 (EPO date Mar. 7, 2012), 62 pages (EPO Mar. 7, 2012) is examiner amend.
U.S. Appl. No. 13/249,739: Response Filed Jul. 9, 2012 to Mar. 7, 2012 Office Action in U.S. Appl. No. 13/249,739, 9 pages.
Van Duin, M., et al., "Studies on borate esters I," Tetrahedron, vol. 40, No. 15 (1984) pp. 2901-2911.
Van Duin, M., et al., "Studies on borate esters II," Tetrahedron, vol. 41, No. 16 (1985) pp. 3411-3421.
Williams, N.A., et al., "The effects of cooling rate on solid phase transitions and associated vial breakage occurring in frozen mannitol solutions," Journal of Parenteral Science & Technology, vol. 40, No. 4 (Jul.-Aug. 1986) pp. 135-141.
Williams, N.A., et al., "Vial breakage by frozen mannitol solutions: correlation with thermal characteristics and effect of stereoisomerism, additives, and vial configuration," Journal of Parenteral Science & Technology, vol. 45, No. 2 (Mar.-Apr. 1991) pp. 94-100.
Written Opinion of the International Searching Authority dated Oct. 5, 2009 issued in International Application No. PCT/US2009/003602, which corresponds to U.S. Appl. No. 12/485,344, 9 pages.
Andersen, M.W. et al., "E- and Z-Pentenylboronates, Reagents for Simple Diasteroselection on Addition to Aldehydes," Chemische Berichte, vol. 122, (1989), pp. 1777-1782.
Armstrong, T., et al., "Central Nervous System Toxicity from Cancer Treatment," Current Oncology Reports, vol. 5, (2004), pp. 11-19.
Ciechanover, A., "The Ubiquitin-Proteasome Proteolytic Pathway," Cell, vol. 79 (Oct. 7, 1994), pp. 13-21.
Gardner, R.C., et al., "Characterization of peptidyl boronic acid inhibitors of mammalian 20 S and 26 S proteasomes and their inhibition of proteasomes in cultured cells," Biochemistry, vol. 346 (2000) pp. 447-454.
Groll, M., et al., "Structure of 20S Proteasome from Yeast at 2.4A Resolution", Nature, vol. 386 (Apr. 3, 1997), pp. 463-471.
Gross, E., et al., "The Peptides: Analysis, Synthesis, Biology," Protection of Functional Groups in Peptide Synthesis, vol. 3, (Academic Press New York) (1981), pp. 3-88.
Harris, J.L., et al., "Substrate Specificity of the Human Proteasome," Chemistry & Biology, vol. 8 (2001), pp. 1131-1141.

(56) References Cited

OTHER PUBLICATIONS

Hoffmann, R.W. et al., "Towards an Understanding of Cram/anti-Cram Selectivity on Addition of Crotylboronates to a-Methylbutyraldehyde," Chemische Berichte, vol. 123, (1990), pp. 2387-2394.

Kettner, C.A. et al., "Inhibition of the Serine Proteases Leukocyte Elastase, Pancreatic Elastase, Cathepsin G, and Chymotrypsin by Peptide Boronic Acids," The Journal of Biological Chemistry, vol. 259, No. 24, (Dec. 25, 1984), pp. 15106-15114.

King, R.W., et al., "How Proteolysis Drives the Cell Cycle," Science, vol. 274 (Dec. 6, 1996), pp. 1652-1659.

Kisselev, A.F., et al., "Proteasome inhibitors: from research tools to drug candidates," Chemistry & Biology, vol. 8, No. 8 (2001) pp. 739-758.

Kupperman, E., et al., "Evaluation of the Proteasome Inhibitor MLN9708 in Preclinical Models of Human Cancer," Cancer Research, vol. 70, No. 5, Mar. 1, 2010, pp. 1970-1980.

Loidl, G., et al., "Bifunctional inhibitors of the trypsin-like activity of eukaryotic proteasomes," Chemistry & Biology, vol. 6, No. 4 (1999) pp. 197-204.

Palombella, V.J., et al., "The Ubiquitin-Proteasome Pathway is Required for Processing the NF-x131 Precursor Protein and the Activation of NF-KB," Cell, vol. 78, (Sep. 9, 1994), pp. 773-785.

Greene, T.W., et al., "Protective groups in organic synthesis," John Wiley & Sons, Inc., Editor (1999) Third Edition, pp. 531-537.

Wallace, R.H. et al., "Preparation and 1-Carbon Homologation of Boronic Ester Substituted 02-isoxazolines: The 1,3 Dipolar Cycloadditon of Nitrile Oxides to Vinyl Boronic Esters," Tetrahedron Letters, vol. 33, No. 46, (1992), pp. 6941-6944.

Zenk, R., et al., "Organic Boronic Acids and Boronic Acid Esters in Industrial Synthesis," Chimica Oggi (Chemistry Today), (May 2003), pp. 70-73.

Kinder, D.H., et al., "Acylamino boronic acids and difluoroborane analogues of amino acids: potent inhibitors of chymotrypsin and elastase," Journal of Medicinal Chemistry, vol. 28, No. 12 (1985) pp. 1917-1925.

Office Action dated Nov. 15, 2012 in pending U.S. Appl. No. 12/586,650.

Tran, T., et al., "Synthesis and structure-activity relationship of N-acyl-Gly-, N-acyl-Sar- and N-blocked-boroPro inhibitors of FAP, DPP4, and POP," Bioorganic & Medicinal Chemistry Letters, vol. 17 (2007) pp. 1438-1442.

International Search Report and Written Opinion for PCT/US2007/017440 dated Dec. 3, 2007, 3 pages.

Written Opinion of the International Searching Authority dated Jun. 7, 2011 issued in International Application No. PCT/US2011/30455 corresponding to U.S. Appl. No. 13/075,306, 4 pages; International Search Report for PCT/US2011/030455 dated Jun. 7, 2011, 2 pages.

Written Opinion of the International Searching Authority dated Jan. 19, 2010 issued in International Application No. PCT/US2009/005324 corresponding to U.S. Appl. No. 12/586,650, 4 pages; International Search Report for PCT/US2009/005324 dated Jan. 19, 2010, 2 pages.

Lala, P.K. et al., "Role of Nitric Oxide in Tumor Progression: Lessons from Experimental Tumors," Cancer and Metastasis Reviews, vol. 17, pp. 91-106 (1998).

Golub, T.R., et al., "Molecular Classification of Cancer: Class Discovery and Class Prediction by Gene Expression Monitoring," Science, vol. 286, pp. 531-537 (Oct. 15, 1999).

Cancer [online], Retrieved on Jul. 6, 2007: MedlinePlus, a service of Medicine and the National Institutes of Health, Retrieved from the Internet, URL: http://www.nlm.nih.gov/medlineplus/cancer.html, 10 pages.

http://goldbook.iupac.org/A00228.html. Retrieved from IUPAC, Compendium of Chemical Terminology, 2nd ed. (the "Gold Book"). Compiled by A. D. McNaught and A. Wilkinson, Blackwell Scientific Publications, Oxford (1997), XML on-line corrected version: http://goldbook.iupac.org (2006-) created by M. Nic, J. Jirat, B. Kosata; updates compiled by A. Jenkins. I SBN 0-9678550-9-8. doi:10.1351/goldbook, 1 page.

* cited by examiner

DERIVATIVES OF 1-AMINO-2-CYCLOPROPYLETHYLBORONIC ACID

PRIORITY CLAIM

This application is a continuation of U.S. application Ser. No. 13/934,989 filed Jul. 3, 2013, which is a continuation of U.S. application Ser. No. 13/075,306 filed Mar. 30, 2011, now U.S. Pat. No. 8,513,218, issued on Aug. 20, 2013, which claims the benefit under 35 U.S.C. §119(e) of U.S. Provisional Patent Application Ser. No. 61/319,464, filed Mar. 31, 2010 which is hereby incorporated by reference in its entirety.

FIELD OF THE INVENTION

The present invention relates to boronic acid and boronic ester compounds useful as proteasome inhibitors. The invention also provides pharmaceutical compositions comprising the compounds of the invention and methods of using the compositions in the treatment of various diseases.

BACKGROUND OF THE INVENTION

Boronic acid and ester compounds display a variety of pharmaceutically useful biological activities. Shenvi et al., U.S. Pat. No. 4,499,082 (1985), discloses that peptide boronic acids are inhibitors of certain proteolytic enzymes. Kettner and Shenvi, U.S. Pat. No. 5,187,157 (1993), U.S. Pat. No. 5,242,904 (1993), and U.S. Pat. No. 5,250,720 (1993), describe a class of peptide boronic acids that inhibit trypsin-like proteases. Kleeman et al., U.S. Pat. No. 5,169,841 (1992), discloses N-terminally modified peptide boronic acids that inhibit the action of renin. Kinder et al., U.S. Pat. No. 5,106,948 (1992), discloses that certain boronic acid compounds inhibit the growth of cancer cells. Bachovchin et al., WO 07/000,5991, discloses peptide boronic acid compounds that inhibit fibroblast activating protein. Kettner et al., WO 01/02424 discloses peptide boronic acid compounds that inhibit hepatitis C viral protease.

Boronic acid and ester compounds hold particular promise as inhibitors of the proteasome, a multicatalytic protease responsible for the majority of intracellular protein turnover. Adams et al., U.S. Pat. No. 5,780,454 (1998), describes peptide boronic ester and acid compounds useful as proteasome inhibitors. The reference also describes the use of boronic ester and acid compounds to reduce the rate of muscle protein degradation, to reduce the activity of NF-κB in a cell, to reduce the rate of degradation of p53 protein in a cell, to inhibit cyclin degradation in a cell, to inhibit the growth of a cancer cell, and to inhibit NF-κB dependent cell adhesion. Furet et al., WO 02/096933, Chatterjee et al., WO 05/016859, and Bernadini et al., WO 05/021558 and WO 06/08660, disclose additional boronic ester and acid compounds that are reported to have proteasome inhibitory activity.

Ciechanover, Cell, 79: 13-21 (1994), discloses that the proteasome is the proteolytic component of the ubiquitin-proteasome pathway, in which proteins are targeted for degradation by conjugation to multiple molecules of ubiquitin. Ciechanover also discloses that the ubiquitin-proteasome pathway plays a key role in a variety of important physiological processes. Rivett et al., Biochem. J. 291:1 (1993) discloses that the proteasome displays tryptic-, chymotryptic-, and peptidylglutamyl-peptidase activities. Constituting the catalytic core of the 26S proteasome is the 20S proteasome. McCormack et al., Biochemistry 37:7792 (1998), teaches that a variety of peptide substrates, including Suc-Leu-Leu-Val-Tyr-AMC, Z-Leu-Leu-Arg-AMC, and Z-Leu-Leu-Glu-2NA, wherein Suc is N-succinyl, AMC is 7-amino-4-methylcoumarin, and 2NA is 2-naphthylamine, are cleaved by the 20S proteasome.

Proteasome inhibition represents an important new strategy in cancer treatment. King et al., Science 274:1652-1659 (1996), describes an essential role for the ubiquitin-proteasome pathway in regulating cell cycle, neoplastic growth and metastasis. The authors teach that a number of key regulatory proteins, including cyclins, and the cyclin-dependent kinases p21 and p27$^{KIP1}$, are temporally degraded during the cell cycle by the ubiquitin-proteasome pathway. The ordered degradation of these proteins is required for the cell to progress through the cell cycle and to undergo mitosis.

Furthermore, the ubiquitin-proteasome pathway is required for transcriptional regulation. Palombella et al., Cell, 78:773 (1994), teaches that the activation of the transcription factor NF-κB is regulated by proteasome-mediated degradation of the inhibitor protein IκB. In turn, NF-κB plays a central role in the regulation of genes involved in the immune and inflammatory responses. Read et al., Immunity 2:493-506 (1995), teaches that the ubiquitin-proteasome pathway is required for expression of cell adhesion molecules, such as E-selectin, ICAM-1, and VCAM-1. Zetter, Seminars in Cancer Biology 4:219-229 (1993), teaches that cell adhesion molecules are involved in tumor metastasis and angiogenesis in vivo, by directing the adhesion and extravastation of tumor cells to and from the vasculature to distant tissue sites within the body. Moreover, Beg and Baltimore, Science 274:782 (1996), teaches that NF-κB is an anti-apoptotic controlling factor, and inhibition of NF-κB activation makes cells more sensitive to environmental stress and cytotoxic agents.

The proteasome inhibitor VELCADE® (bortezomib; N-2-pyrazinecarbonyl-L-phenylalanine-L-leucineboronic acid) is the first proteasome inhibitor to achieve regulatory approval. Mitsiades et al., Current Drug Targets, 7:1341 (2006), reviews the clinical studies leading to the approval of bortezomib for the treatment of multiple myeloma patients who have received at least one prior therapy. Fisher et al., J. Clin. Oncol., 30:4867, describes an international multi-center Phase II study confirming the activity of bortezomib in patients with relapsed or refractory mantle cell lymphoma. Ishii et al., Anti-Cancer Agents in Medicinal Chemistry, 7:359 (2007), and Roccaro et al., Curr. Pharm. Biotech., 7:1341 (2006), discuss a number of molecular mechanisms that may contribute to the antitumor activities of bortezomib.

Structural analysis reported by Voges et al., Annu. Rev. Biochem., 68:1015 (1999) reveals that the 20S proteasome comprises 28 subunits, with the catalytic subunits β1, β2, and β5 being responsible for peptidylglutamyl, tryptic, and chymotryptic peptidase activity, respectively. Rivett et al., Curr. Protein Pept. Sci., 5:153 (2004) discloses that when the proteasome is exposed to certain cytokines, including IFN-γ and TNF-α, the β1, β2, and β5 subunits are replaced with alternate catalytic subunits, β1i, β2i, and β5i, to form a variant form of the proteasome known as the immunoproteasome.

Orlowski, Hematology (Am. Soc. Hematol. Educ. Program) 220 (2005), discloses that the immunoproteasome also is expressed constitutively in some cells derived from hematopoietic precursors. The author suggests that inhibitors specific for the immunoproteasome may allow for targeted therapy against cancers arising from hematologic origins, thereby potentially sparing normal tissues, such as gastrointestinal and neurological tissues, from side effects.

As evidenced by the above references, the proteasome represents an important target for therapeutic intervention. There is thus a continuing need for new and/or improved proteasome inhibitors.

DESCRIPTION OF THE INVENTION

The present invention provides compounds that are effective inhibitors of one or more peptidase activities of the proteasome. These compounds are useful for inhibiting proteasome activity in vitro and in vivo, and are especially useful for the treatment of various cell proliferative diseases.

Compounds of the invention are of the general formula (I):

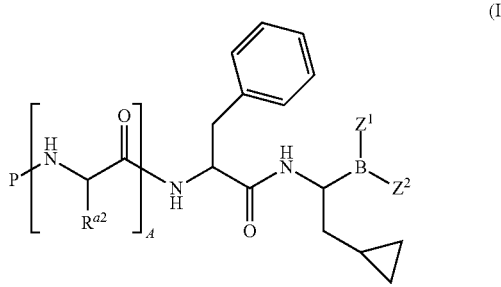

(I)

or a pharmaceutically acceptable salt or boronic acid anhydride thereof, wherein:

A is 0, 1, or 2;

P is hydrogen or an amino-group-blocking moiety;

each $R^{a2}$ independently is hydrogen, $C_{1-6}$ aliphatic, $C_{1-6}$ fluoroaliphatic, $-(CH_2)_m-CH_2-R^B$, $-(CH_2)_m-CH_2-NHC(=NR^4)NH-Y$, $-(CH_2)_m-CH_2-CON(R^4)_2$, $-(CH_2)_m-CH_2-N(R^4)CON(R^4)_2$, $-(CH_2)_m-CH(R^6)N(R^4)_2$, $-(CH_2)_m-CH(R^5)-OR^5$, or $-(CH_2)_m-CH(R^5)-SR^5$;

each Y independently is hydrogen, $-CN$, $-NO_2$, or $-S(O)_2-R^{10}$;

each $R^B$ independently is a substituted or unsubstituted mono- or bicyclic ring system;

each $R^4$ independently is hydrogen or a substituted or unsubstituted aliphatic, aryl, heteroaryl, or heterocyclyl group; or two $R^4$ on the same nitrogen atom, taken together with the nitrogen atom, form a substituted or unsubstituted 4- to 8-membered heterocyclyl ring having, in addition to the nitrogen atom, 0-2 ring heteroatoms independently selected from N, O, and S;

each $R^5$ independently is hydrogen or a substituted or unsubstituted aliphatic, aryl, heteroaryl, or heterocyclyl group;

each $R^6$ independently is a substituted or unsubstituted aliphatic, aryl, or heteroaryl group;

each $R^{10}$ independently is $C_{1-6}$ aliphatic, $C_{6-10}$ aryl, or $-N(R^4)_2$;

m is 0, 1, or 2; and $Z^1$ and $Z^2$ are each independently hydroxy, alkoxy, aryloxy, or aralkoxy; or $Z^1$ and $Z^2$ together form a moiety derived from a boronic acid complexing agent.

Unless otherwise explicitly stated, the term "proteasome" is intended to refer to constitutive proteasome, immunoproteasome, or both.

The term "aliphatic" or "aliphatic group", as used herein, means a substituted or unsubstituted straight-chain, branched, or cyclic $C_{1-12}$ hydrocarbon, which is completely saturated or which contains one or more units of unsaturation, but which is not aromatic. For example, suitable aliphatic groups include substituted or unsubstituted linear, branched or cyclic alkyl, alkenyl, or alkynyl groups and hybrids thereof, such as (cycloalkyl)alkyl, (cycloalkenyl)alkyl or (cycloalkyl)alkenyl. In various embodiments, the aliphatic group has 1 to 12, 1 to 8, 1 to 6, 1 to 4, or 1 to 3 carbons.

The terms "alkyl", "alkenyl", and "alkynyl", used alone or as part of a larger moiety, refer to a straight or branched chain aliphatic group having from 1 to 12 carbon atoms. For purposes of the present invention, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, and hexyl.

For purposes of the present invention, the term "alkenyl" will be used when the carbon atom attaching the aliphatic group to the rest of the molecule forms part of a carbon-carbon double bond. Alkenyl groups include, without limitation, vinyl, 1-propenyl, 1-butenyl, 1-pentenyl, and 1-hexenyl.

For purposes of the present invention, the term "alkynyl" will be used when the carbon atom attaching the aliphatic group to the rest of the molecule forms part of a carbon-carbon triple bond. Alkynyl groups include, without limitation, ethynyl, 1-propynyl, 1-butynyl, 1-pentynyl, and 1-hexynyl.

The term "cycloaliphatic", used alone or as part of a larger moiety, refers to a saturated or partially unsaturated cyclic aliphatic ring system having from 3 to about 14 members, wherein the aliphatic ring system is optionally substituted. In some embodiments, the cycloaliphatic is a monocyclic hydrocarbon having 3-8 or 3-6 ring carbon atoms. Nonlimiting examples include cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloaliphatic is a bridged or fused bicyclic hydrocarbon having 6-12, 6-10, or 6-8 ring carbon atoms, wherein any individual ring in the bicyclic ring system has 3-8 members.

In some embodiments, two adjacent substituents on the cycloaliphatic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the term "cycloaliphatic" includes aliphatic rings that are fused to one or more aryl, heteroaryl, or heterocyclyl rings. Nonlimiting examples include indanyl, 5,6,7,8-tetrahydroquinoxalinyl, decahydronaphthyl, or tetrahydronaphthyl, where the radical or point of attachment is on the aliphatic ring.

The terms "aryl" and "ar-", used alone or as part of a larger moiety, e.g., "aralkyl", "aralkoxy", or "aryloxyalkyl", refer to a $C_6$ to $C_{14}$ aromatic hydrocarbon, comprising one to three rings, each of which is optionally substituted. Preferably, the aryl group is a $C_{6-10}$ aryl group. Aryl groups include, without limitation, phenyl, naphthyl, and anthracenyl. In some embodiments, two adjacent substituents on the aryl ring, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the term "aryl", as used herein, includes groups in which an aryl ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group may be mono-, bi-, tri-, or polycyclic, preferably mono-, bi-, or tricyclic, more preferably mono- or bicyclic. The term "aryl" may be used interchangeably with the terms "aryl group", "aryl moiety", and "aryl ring".

An "aralkyl" or "arylalkyl" group comprises an aryl group covalently attached to an alkyl group, either of which independently is optionally substituted. Preferably, the aralkyl group is $C_{6-10}$ aryl($C_{1-6}$)alkyl, $C_{6-10}$ aryl($C_{1-4}$)alkyl, or $C_{6-10}$ aryl($C_{1-3}$)alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to four heteroatoms. The term "heteroatom" refers to nitrogen, oxygen, or sulfur, and includes any oxidized form of nitrogen or sulfur, and any quaternized form of a basic nitrogen. Thus, when used in reference to a ring atom of a heteroaryl, the term "nitrogen" includes an oxidized nitrogen (as in pyridine N-oxide). Certain nitrogen atoms of 5-membered heteroaryl groups also are substitutable, as further defined below. Heteroaryl groups include, without limitation, radicals derived from thiophene, furan, pyrrole, imidazole, pyrazole, triazole, tetrazole, oxazole, isoxazole, oxadiazole, thiazole, isothiazole, thiadiazole, pyridine, pyridazine, pyrimidine, pyrazine, indolizine, naphthyridine, pteridine, pyrrolopyridine, imidazopyridine, oxazolopyridine, thiazolopyridine, triazolopyridine, pyrrolopyrimidine, purine, and triazolopyrimidine. As used herein, the phrase "radical derived from" means a monovalent radical produced by removal of a hydrogen radical from the parent heteroaromatic ring system. The radical (i.e., the point of attachment of the heteroaryl to the rest of the molecule) may be created at any substitutable position on any ring of the parent heteroaryl ring system.

In some embodiments, two adjacent substituents on the heteroaryl, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, benzoxazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono-, bi-, tri-, or polycyclic, preferably mono-, bi-, or tricyclic, more preferably mono- or bicyclic. The term "heteroaryl" may be used interchangeably with the terms "heteroaryl ring", or "heteroaryl group", any of which terms include rings that are optionally substituted. The term "heteroaralkyl" refers to an alkyl group substituted by a heteroaryl, wherein the alkyl and heteroaryl portions independently are optionally substituted.

As used herein, the terms "aromatic ring" and "aromatic ring system" refer to an optionally substituted mono-, bi-, or tricyclic group having 0-6, preferably 0-4 ring heteroatoms, and having 6, 10, or 14 πelectrons shared in a cyclic array. Thus, the terms "aromatic ring" and "aromatic ring system" encompass both aryl and heteroaryl groups.

As used herein, the terms "heterocycle", "heterocyclyl", "heterocyclic radical", and "heterocyclic ring" are used interchangeably and refer to a stable 3- to 7-membered monocyclic, or to a fused 7- to 10-membered or bridged 6- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a heterocyclyl ring having 1-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). A heterocyclic ring can be attached to its pendant group at any heteroatom or carbon atom that results in a stable structure, and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

In some embodiments, two adjacent substituents on a heterocyclic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the terms "heterocycle", "heterocyclyl", "heterocyclyl ring", "heterocyclic group", "heterocyclic moiety", and "heterocyclic radical", are used interchangeably herein, and include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "linker group" or "linker" means an organic moiety that connects two parts of a compound. Linkers typically comprise an atom such as oxygen or sulfur, a unit such as —NH—, —CH$_2$—, —C(O)—, —C(O)NH—, or a chain of atoms, such as an alkylene chain. The molecular mass of a linker is typically in the range of about 14 to 200, preferably in the range of 14 to 96 with a length of up to about six atoms. In some embodiments, the linker is a $C_{1-6}$ alkylene chain.

The term "alkylene" refers to a bivalent alkyl group. An "alkylene chain" is a polymethylene group, i.e., $-(CH_2)_x-$, wherein x is a positive integer, preferably from 1 to 6, from 1 to 4, from 1 to 3, from 1 to 2, or from 2 to 3. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

An alkylene chain also can be optionally interrupted by a functional group. An alkylene chain is "interrupted" by a functional group when an internal methylene unit is replaced with the functional group. Nonlimiting examples of suitable "interrupting functional groups" include $-C(R^*)=C(R^*)-$, $-C\equiv C-$, $-O-$, $-S-$, $-S(O)-$, $-S(O)_2-$, $-S(O)_2N(R^+)-$, $-N(R^*)-$, $-N(R^+)CO-$, $-N(R^+)C(O)N(R^+)-$, $-N(R^+)C(=NR^+)-N(R^+)-$, $-N(R^+)-C(=NR^+)-$, $-N(R^+)CO_2-$, $-N(R^+)SO_2-$, $-N(R^+)SO_2N(R^+)-$, $-OC(O)-$, $-OC(O)O-$, $-OC(O)N(R^+)-$, $-C(O)-$, $-CO_2-$, $-C(O)-N(R^+)-$, $-C(O)-C(O)-$, $-C(=NR^+)-N(R^+)-$, $-C(NR^+)=N-$, $-C(=NR^+)-O-$, $-C(OR^*)=N-$, $-C(R^\circ)=N-O-$, or $-N(R^+)-N(R^+)-$. Each $R^+$, independently, is hydrogen or an optionally substituted aliphatic, aryl, heteroaryl, or heterocyclyl group, or two $R^+$ on the same nitrogen atom, taken together with the nitrogen atom, form a 5-8 membered aromatic or non-aromatic ring having, in addition to the nitrogen atom, 0-2 ring heteroatoms selected from N, O, and S. Each $R^*$ independently is hydrogen or an optionally substituted aliphatic, aryl, heteroaryl, or heterocyclyl group.

Examples of $C_{3-6}$ alkylene chains that have been "interrupted" with $-O-$ include. e.g., $-CH_2OCH_2-$, $-CH_2-O-(CH_2)_2-$, $-CH_2-O-(CH_2)_3-$, $-CH_2-O-(CH_2)_4-$, $-(CH_2)_2OCH_2-$, $-(CH_2)_2O(CH_2)_2-$, $-(CH_2)_2O(CH_2)_3-$, $-(CH_2)_3-O-(CH_2)-$, $-(CH_2)_3-O-(CH_2)_2-$, and $-(CH_2)_4O(CH_2)-$. Other examples of alkylene chains that are "interrupted" with functional groups include $-CH_2ZCH_2-$, $-CH_2Z(CH_2)_2-$, $-CH_2Z(CH_2)_3-$, $-CH_2Z(CH_2)_4-$, $-(CH_2)_2ZCH_2-$, $-(CH_2)_2Z(CH_2)_2-$, $-(CH_2)_2Z(CH_2)_3-$, $-(CH_2)_3Z(CH_2)-$, $-(CH_2)_3Z(CH_2)_2-$, and $-(CH_2)_4Z(CH_2)-$, wherein Z is one of the "interrupting" functional groups listed above.

One of ordinary skill in the art will recognize that when an alkylene chain having an interruption is attached to a functional group, certain combinations would not be sufficiently stable for pharmaceutical use. Similarly, certain combinations of $T^1$ and $R^{2c}$, or $T^2$ and $R^{2d}$, would not be sufficiently stable for pharmaceutical use. Only stable or chemically feasible compounds are within the scope of the present invention. A stable or chemically feasible compound is one which maintains its integrity long enough to be useful for therapeutic or prophylactic administration to a patient. Preferably, the chemical structure is not substantially altered when kept at a temperature below −70° C., below −50° C., below −20° C., below 0° C., or below 20° C., in the absence of moisture or other chemically reactive conditions for at least a week.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different.

As used herein, the term "independently selected" means that the same or different values may be selected for multiple instances of a given variable in a single compound.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Nonlimiting examples of suitable substituents on the unsaturated carbon atom of an aryl or heteroaryl group include -halo, $-NO_2$, $-CN$, $-R^*$, $-C(R^*)=C(R^*)_2$, $-C\equiv C-R^*$, $-OR^*$, $-SR^\circ$, $-S(O)R^\circ$, $-SO_2R^\circ$, $-SO_3R^*$, $-SO_2N(R^+)_2$, $-N(R^+)_2$, $-NR^+C(O)R^*$, $-NR^+C(O)N(R^+)_2$, $-N(R^+)C(=NR^+)-N(R^+)_2$, $-N(R^+)-C(=NR^+)-R^\circ$, $-NR^+CO_2R^\circ$, $-NR^+SO_2R^\circ$, $-NR^+SO_2N(R^+)_2$, $-O-C(O)R^*$, $-O-CO_2R^*$, $-OC(O)-N(R^+)_2$, $-C(O)R^*$, $-CO_2R^*$, $-C(O)-C(O)N(R^+)_2$, $-C(O)N(R^+)-OR^*$, $-C(O)N(R^+)-C(=NR^+)-N(R^+)_2$, $-N(R^+)C(=NR^+)-N(R^+)-C(O)R^*$, $-C(=NR^+)-N(R^+)_2$, $-C(=NR^+)-OR^*$, $-N(R^+)-N(R^+)_2$, $-C(=NR^+)-N(R^+)-OR^*$, $-C(R_o)=N-OR^*$, $-P(O)(R^*)_2$, $-P(O)(OR^*)_2$, $-O-P(O)-OR^*$, and $-P(O)(NR^+)-N(R^+)_2$, wherein $R^\circ$ is an optionally substituted aliphatic, aryl, or heteroaryl group, and $R^+$ and $R^*$ are as defined above, or two adjacent substituents, taken together with their intervening atoms, form a 5-6 membered unsaturated or partially unsaturated ring having 0-3 ring atoms selected from the group consisting of N, O, and S.

An aliphatic group or a non-aromatic heterocyclic ring may be substituted with one or more substituents. Examples of suitable substituents on the saturated carbon of an aliphatic group or of a non-aromatic heterocyclic ring include, without limitation, those listed above for the unsaturated carbon of an aryl or heteroaryl group and the following: =O, =S, $=C(R^*)_2$, $=N-N(R^*)_2$, $=N-OR^*$, $=N-NHC(O)R^*$, $=N-NHCO_2R^\circ$, $=N-NHSO_2R^\circ$, or $=N-R^*$, where each $R^*$ and $R^\circ$ is as defined above.

Suitable substituents on a substitutable nitrogen atom of a heteroaryl or non-aromatic heterocyclic ring include, without limitation, $-R^*$, $-N(R^*)_2$, $-C(O)R^*$, $-CO_2R^*$, $-C(O)-C(O)R^*-C(O)CH_2C(O)R^*$, $-SO_2R^*$, $-SO_2N(R^*)_2$, $-C(=S)N(R^*)_2$, $-C(=NH)-N(R^*)_2$, and $-NR^*SO_2R^*$; wherein each $R^*$ is as defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "comprises" means "includes, but is not limited to."

It will be apparent to one skilled in the art that certain compounds of this invention may exist in tautomeric forms, all such tautomeric forms of the compounds being within the scope of the invention. Unless otherwise stated, structures depicted herein are also meant to include all geometric (or conformational) isomers, i.e., (Z) and (E) double bond isomers and (Z) and (E) conformational isomers, as well as all stereochemical forms of the structure; i.e., the R and S configurations for each asymmetric center. Therefore, single stereochemical isomers as well as enantiomeric and diastereomeric mixtures of the present compounds are within the scope of the invention. When a mixture is enriched in one stereoisomer relative to another stereoisomer, the mixture may contain, for example, an enantiomeric excess of at least 50%, 75%, 90%, 99%, or 99.5%.

Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}$C— or $^{14}$C-enriched carbon are within the scope of the invention.

In the compounds of formula (I), the variable P is hydrogen or an amino-group-blocking moiety. Non-limiting examples of amino-group-blocking moieties can be found in P. G. M. Wuts and T. W. Greene, *Greene's Protective Groups in Organic Synthesis* (4$^{th}$ ed.), John Wiley & Sons, NJ (2007), and include, e.g., acyl, sulfonyl, oxyacyl, and aminoacyl groups.

In some embodiments, P is $R^c$—C(O)—, $R^c$—O—C(O)—, $R^c$—N($R^{4c}$)—C(O)—, $R^c$—S(O)$_2$—, or $R^c$—N($R^{4c}$)—S(O)$_2$—, where $R^c$ is selected from the group consisting of $C_{1-6}$ aliphatic, $C_{1-6}$ fluoroaliphatic, —$R^D$, -$T^1$-$R^D$, and -$T^1$-$R^{2c}$, and the variables $T^1$, $R^D$, $R^{2c}$, and $R^{4c}$ have the values described below.

The variable $R^{4c}$ is hydrogen, $C_{1-4}$ alkyl, $C_{1-4}$ fluoroalkyl, or $C_{6-10}$ ar($C_{1-4}$)alkyl, the aryl portion of which is substituted or unsubstituted. In some embodiments, $R^{4c}$ is hydrogen or $C_{1-4}$ alkyl. In certain particular embodiments, $R^{4c}$ is hydrogen.

The variable $T^1$ is a $C_{1-6}$ alkylene chain substituted with 0-2 independently selected $R^{3a}$ or $R^{3b}$, wherein the alkylene chain optionally is interrupted by —C($R^5$)=C($R^5$)—, —C≡C—, or —O—. Each $R^{3a}$ independently is selected from the group consisting of —F, —OH, —O($C_{1-4}$ alkyl), —CN, —N($R^4$)$_2$, —C(O)($C_{1-4}$ alkyl), —CO$_2$H, —CO$_2$($C_{1-4}$ alkyl), —C(O)NH$_2$, and —C(O)—NH($C_{1-4}$ alkyl). Each $R^{3b}$ independently is a $C_{1-3}$ aliphatic optionally substituted with $R^{3a}$ or $R^7$. Each $R^7$ is a substituted or unsubstituted aromatic group. In some embodiments, $T^1$ is a $C_{1-4}$ alkylene chain.

The variable $R^{2a}$ is halo, —OR$^5$, —SR$^6$, —S(O)R$^6$, —SO$_2$R$^6$, —SO$_2$N($R^4$)$_2$, —N($R^4$)$_2$, —NR$^4$C(O)R$^5$, —NR$^4$C(O)N($R^4$)$_2$, —NR$^4$CO$_2$R$^6$, —N($R^4$)SO$_2$R$^6$, —N($R^4$)SO$_2$N($R^4$)$_2$, —O—C(O)R$^5$, —OC(O)N($R^4$)$_2$, —C(O)R$^5$, —CO$_2$R$^5$, or —C(O)N($R^4$)$_2$, where:

each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 4- to 8-membered heterocyclyl ring having, in addition to the nitrogen atom, 0-2 ring heteroatoms independently selected from N, O, and S;

each $R^5$ independently is hydrogen or an optionally substituted aliphatic, aryl, heteroaryl, or heterocyclyl group; and each $R^6$ independently is an optionally substituted aliphatic, aryl, or heteroaryl group.

The variable $R^D$ is a substituted or unsubstituted aromatic, heterocyclyl, or cycloaliphatic ring, any of which is optionally fused to a substituted or unsubstituted aromatic, heterocyclyl or cycloaliphatic ring. Each saturated ring carbon atom in $R^D$ is unsubstituted or is substituted with =O, $R^d$, or $R^{8d}$. Each unsaturated ring carbon in $R^D$ is unsubstituted or is substituted with $R^d$ or $R^{8d}$. Each substitutable ring nitrogen atom in $R^D$ is unsubstituted or is substituted with —C(O)R$^5$, —C(O)N($R^4$)$_2$, —CO$_2$R$^6$, —SO$_2$R$^6$, —SO$_2$N($R^4$)$_2$, $C_{1-4}$ aliphatic, a substituted or unsubstituted $C_{6-10}$ aryl, or a $C_{6-10}$ ar($C_{1-4}$)alkyl, the aryl portion of which is substituted or unsubstituted.

In some embodiments, one or two saturated ring carbon atoms in $R^D$ are substituted with =O; the remaining substitutable ring carbon atoms in $R^D$ are substituted with 0-2 $R^d$ and 0-2 $R^{8d}$; and each substitutable ring nitrogen atom in $R^D$ is unsubstituted or is substituted with —C(O)R$^5$, —C(O)N($R^4$)$_2$, —CO$_2$R$^6$, —SO$_2$R$^6$, —SO$_2$N($R^4$)$_2$, $C_{1-4}$ aliphatic, a substituted or unsubstituted $C_{6-10}$ aryl, or a $C_{6-10}$ ar($C_{1-4}$)alkyl, the aryl portion of which is substituted or unsubstituted.

Each $R^d$ independently is selected from the group consisting of $C_{1-6}$ aliphatic, $C_{1-6}$ fluoroaliphatic, halo, —$R^{1d}$, —$R^{2d}$, -$T^2$-$R^{1d}$, and -$T^2$-$R^{2d}$, where the variables $T^2$, $R^{1d}$, $R^{2d}$, and $R^{8d}$ have the values described below.

$T^2$ is a $C_{1-6}$ alkylene chain substituted with 0-2 independently selected $R^{3a}$ or $R^{3b}$, wherein the alkylene chain optionally is interrupted by —C($R^5$)=C($R^5$)—, —C≡C—, or —O—. The variables $R^{3a}$ and $R^{3b}$ have the values described above.

Each $R^{1d}$ independently is a substituted or unsubstituted aryl, heteroaryl, heterocyclyl, or cycloaliphatic ring.

Each $R^{2d}$ independently is —NO$_2$, —CN, —C($R^5$)=C($R^5$)$_2$, —C≡C—R$^5$, —OR$^5$, —SR$^6$, —S(O)R$^6$, —SO$_2$R$^6$, —SO$_2$N($R^4$)$_2$, —N($R^4$)$_2$, —NR$^4$C(O)R$^5$, —NR$^4$C(O)N($R^4$)$_2$, —N($R^4$)C(=NR$^4$)—N($R^4$)$_2$, —N($R^4$)C(=NR$^4$)—R$^6$, —NR$^4$CO$_2$R$^6$, —N($R^4$)SO$_2$R$^6$, —N($R^4$)SO$_2$N($R^4$)$_2$, —O—C(O)R$^5$, —OC(O)N($R^4$)$_2$, —C(O)R$^5$, —CO$_2$R$^5$, —C(O)N($R^4$)$_2$, —C(O)N($R^4$)—OR$^5$, —C(O)N($R^4$)C(=NR$^4$)—N($R^4$)$_2$, —N($R^4$)C(=NR$^4$)—N($R^4$)—C(O)R$^5$, or —C(=NR$^4$)—N($R^4$)$_2$.

Each $R^{8d}$ independently is selected from the group consisting of $C_{1-4}$ aliphatic, $C_{1-4}$ fluoroaliphatic, halo, —OH, —O($C_{1-4}$ aliphatic), —NH$_2$, —NH($C_{1-4}$ aliphatic), and —N($C_{1-4}$ aliphatic)$_2$.

In some embodiments, $R^D$ is a substituted or unsubstituted mono- or bicyclic ring system selected from the group consisting of furanyl, thienyl, pyrrolyl, isoxazolyl, oxazolyl, thiazolyl, isothiazolyl, imidazolyl, pyrazolyl, oxadiazolyl, thiadiazolyl, phenyl, pyridinyl, pyridazinyl, pyrimidinyl, pyrazinyl, benzofuranyl, benzothiophenyl, benzothiazolyl, indolyl, benzoxazolyl, benzisoxazolyl, benzimidazolyl, indazolyl, purinyl, naphthyl, quinolinyl, isoquinolinyl, cinnolinyl, quinazolinyl, quinoxalinyl, phthalazinyl, naphthyridinyl, tetrahydroquinolinyl, tetrahydroisoquinolinyl, tetrahydroquinoxalinyl, oxodihydroindolyl, oxodihydrobenzoxazinyl, and dihydrobenzoxazinyl. In some embodiments, $R^D$ is a substituted or unsubstituted mono- or bicyclic ring system selected from the group consisting of phenyl, pyridinyl, pyrimidinyl, pyrazinyl, naphthyl, benzimidazolyl, benzothiazolyl, indolyl, quinolinyl, isoquinolinyl, quinoxalinyl, tetrahydroquinolinyl, tetrahydroisoquinolinyl, tetrahydroquinoxalinyl, oxodihydroindolyl, oxodihydrobenzoxazinyl, and dihydrobenzoxazinyl. In some embodiments, $R^D$ is a substituted or unsubstituted mono- or bicyclic ring system selected from the group consisting of phenyl, pyridinyl, pyrazinyl, benzothiazolyl, indolyl, isoquinolinyl, tetrahydroquinoxalinyl, oxodihydroindolyl, oxodihydrobenzoxazinyl, and dihydrobenzoxazinyl.

In some embodiments, $R^D$ is a substituted or unsubstituted tricyclic ring system selected from the group consisting of dibenzofuranyl, dibenzothienyl, indenopyridyl, benzofuropyridyl, benzothienopyridyl, benzofuropyrazinyl, S,S-dioxodibenzothiophenyl, xanthenyl, dibenzo-1,4-dioxinyl, phenoxathiinyl, phenoxazinyl, phenothiazinyl, pyridoindolyl, acridinyl, and phenanthridinyl. In some embodiments, $R^D$ is a substituted or unsubstituted tricyclic ring system selected from the group consisting of benzofuropyridyl, pyridoindolyl, and benzofuropyrazinyl. In some embodiments, $R^D$ is substituted or unsubstituted benzofuropyridyl.

In some embodiments, one or two saturated ring carbon atoms in $R^D$ are substituted with =O, and the remaining substitutable ring carbon atoms in $R^D$ are substituted with 0-1 $R^d$ and 0-2 $R^{8d}$, wherein:

each $R^d$ independently is selected from the group consisting of $C_{1-6}$ aliphatic, $C_{1-6}$ fluoroaliphatic, halo, —$R^{1d}$, —$R^{2d}$, -$T^2$-$R^{1d}$, and -$T^2$-$R^{2d}$;

$T^2$ is a $C_{1-3}$ alkylene chain that is unsubstituted or is substituted with $R^{3a}$ or $R^{3b}$;

each $R^{1d}$ independently is a substituted or unsubstituted aryl, heteroaryl, heterocyclyl, or cycloaliphatic ring; and each $R^{2d}$ independently is –$OR^5$, —$SR^6$, —$S(O)R^6$, —$SO_2R^6$, —$SO_2N(R^4)_2$, —$N(R^4)_2$, —$NR^4C(O)R^5$, —$NR^4C(O)N(R^4)_2$, —O—$C(O)R^5$, —$OC(O)N(R^4)_2$, —$C(O)R^5$, —$CO_2R^5$, or —$C(O)N(R^4)_2$.

In some embodiments, the variable $R^d$ has the formula -Q-$R^E$, where Q is —O—, —NH—, —S(O)—, —S(O)$_2$—, —C(O)—, or —CH$_2$—, and $R^E$ is a substituted or unsubstituted aryl, heteroaryl, heterocyclyl, or cycloaliphatic ring. In some embodiments, $R^E$ is a substituted or unsubstituted phenyl, pyridinyl, pyrimidinyl, pyrazinyl, quinolinyl, benzothiazolyl, benzimidazolyl, indolyl, piperidinyl, piperazinyl, or morpholinyl ring.

In some embodiments, the variable $R^d$ has the formula -Q-$R^E$, where Q is a bond and $R^E$ is a substituted or unsubstituted aryl, heteroaryl, heterocyclyl, or cycloaliphatic ring. In some embodiments, $R^E$ is a substituted or unsubstituted phenyl, pyridinyl, pyrimidinyl, pyrazinyl, quinolinyl, thiazolyl, oxazolyl, imidazolyl, benzothiazolyl, benzimidazolyl, indolyl, piperidinyl, piperazinyl, or morpholinyl ring. In some embodiments, $R^E$ is a substituted or unsubstituted phenyl, pyridinyl, pyrimidinyl, pyrazinyl, thiazolyl, oxazolyl, imidazolyl, piperidinyl, piperazinyl, or morpholinyl ring.

In some embodiments, P has the formula $R^c$—C(O)—, where $R^c$ is $C_{1-4}$ alkyl, $C_{1-4}$ fluoroalkyl, or $C_{6-10}$ ar($C_{1-4}$) alkyl, the aryl portion of which is substituted or unsubstituted. In certain such embodiments, P is selected from the group consisting of acetyl, trifluoroacetyl, and phenylacetyl.

In some other embodiments, P has the formula $R^D$—C(O)—, where $R^D$ is a substituted or unsubstituted phenyl, pyridinyl, pyrazinyl, pyrimidinyl, quinolinyl, or quinoxalinyl. In certain embodiments, P has the formula $R^D$—C(O)—, where $R^D$ is a phenyl, pyridinyl, pyrazinyl, pyrimidinyl, naphthyl, quinolinyl, quinoxalinyl, benzimidazolyl, or dihydrobenzoxazinyl substituted with 0-1 $R^d$ and 0-2 $R^{8d}$. In certain particular embodiments, P has the formula $R^D$—C(O)—, where $R^D$ is a phenyl, or pyrazinyl, substituted with 0-1 $R^d$ and 0-2 $R^{8d}$. In certain particular embodiments, P has the formula $R^D$—C(O)—, where $R^D$ is a pyridinyl, pyrazinyl, or pyrimidinyl, which is substituted with a substituent of formula —O—$R^E$, and $R^E$ is a substituted or unsubstituted phenyl. In certain other particular embodiments, P has the formula $R^D$—C(O)—, where $R^D$ is a phenyl, which is substituted with a substituent of formula —O—$R^E$, and $R^E$ is a substituted or unsubstituted pyridinyl, pyrazinyl, or pyrimidinyl.

In some other embodiments, P has the formula $R^c$—$SO_2$—, where $R^c$ is —$R^D$ or -$T^1$-$R^D$, where $T^1$ is $C_{1-4}$ alkylene and $R^D$ is a phenyl, pyridinyl, pyrazinyl, pyrimidinyl, naphthyl, quinolinyl, isoquinolinyl, quinoxalinyl, benzimidazolyl, benzothiazolyl, indolyl, oxodihydroindolyl, oxodihydrobenzoxazinyl, or dihydrobenzoxazinyl substituted with 0-1 $R^d$ and 0-2 $R^{8d}$. In some embodiments, P has the formula $R^D$—$SO_2$—, where $R^D$ is a substituted or unsubstituted phenyl, pyridinyl, pyrazinyl, pyrimidinyl, naphthyl, quinolinyl, isoquinolinyl, quinoxalinyl, benzimidazolyl, benzothiazolyl, indolyl, oxodihydroindolyl, oxodihydrobenzoxazinyl, or dihydrobenzoxazinyl. In certain embodiments, P has the formula $R^D$—$SO_2$—, where $R^D$ is a phenyl, pyridinyl, pyrazinyl, isoquinolinyl, benzothiazolyl, indolyl, oxodihydroindolyl, oxodihydrobenzoxazinyl, or dihydrobenzoxazinyl substituted with 0-1 $R^d$ and 0-2 $R^{8d}$. In certain particular embodiments, P has the formula $R^D$—$SO_2$—, where $R^D$ is a pyridinyl, pyrazinyl, or pyrimidinyl, which is substituted with a substituent of formula —O—$R^E$, and $R^E$ is a substituted or unsubstituted phenyl. In certain other particular embodiments, P has the formula $R^D$—$SO_2$—, where $R^D$ is a phenyl, which is substituted with a substituent of formula —O—$R^E$, and $R^E$ is a substituted or unsubstituted pyridinyl, pyrazinyl, pyrimidinyl, quinolinyl, benzothiazolyl, benzimidazolyl, or indolyl.

Each variable $R^{a2}$ is independently $C_{1-6}$ aliphatic, $C_{1-6}$ fluoroaliphatic, —(CH$_2$)$_m$—CH$_2$—$R^B$, —(CH$_2$)$_m$—CH$_2$—NHC(=NR$^4$)NH—Y, —(CH$_2$)$_m$—CH$_2$—CON(R$^4$)$_2$, —(CH$_2$)$_m$—CH$_2$—N(R$^4$)CON(R$^4$)$_2$, —(CH$_2$)$_m$—CH(R$^6$)N(R$^4$)$_2$, —(CH$_2$)$_m$—CH(R$^5$)—OR$^5$, or —(CH$_2$)$_m$—CH(R$^5$)—SR$^5$, where the variables $R^4$, $R^5$, and $R^6$ have the values described above, and the variables $R^B$ and m have the values described below.

Each $R^B$, independently, is a substituted or unsubstituted mono- or bicyclic ring system. In some embodiments, each $R^B$ independently is a substituted or unsubstituted phenyl, pyridyl, indolyl, benzimidazolyl, naphthyl, quinolinyl, quinoxalinyl, or isoquinolinyl ring. In certain embodiments, $R^B$ is a substituted or unsubstituted phenyl ring.

The variable m is 0, 1, or 2. In some embodiments, m is 0 or 1.

In some embodiments, each $R^{a2}$ is independently $C_{1-6}$ aliphatic, $C_{1-6}$ fluoroaliphatic, or —(CH$_2$)$_m$—CH$_2$—$R^B$, and m is 0 or 1. In some such embodiments, $R^B$ is substituted or unsubstituted phenyl. In certain embodiments, $R^{a2}$ is isopropyl, benzyl, or phenethyl.

The variable A is 0, 1, or 2. In some embodiments, A is 0 or 1. In certain embodiments, A is 0.

In some embodiments, the invention relates to a compound of formula (I) characterized by formula (I-A):

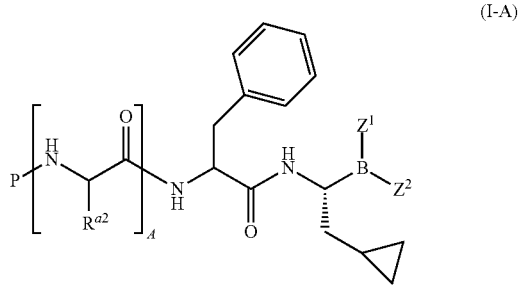

(I-A)

or a pharmaceutically acceptable salt or boronic acid anhydride thereof, wherein each of the variables P, $R^{a2}$, A, $Z^1$, and $Z^2$ has the values and preferred values described above for formula (I).

In certain embodiments, the invention relates to a compound of formula (I) characterized by formula (I-B):

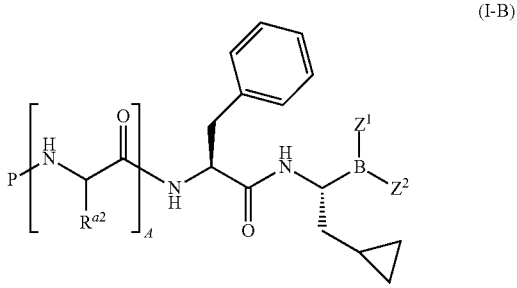

(I-B)

or a pharmaceutically acceptable salt or boronic acid anhydride thereof, wherein each of the variables P, $R^{a2}$, A, $Z^1$, and $Z^2$ has the values and preferred values described above for formula (I).

In certain particular embodiments, the invention relates to a compound of formula (I), characterized by formula (II):

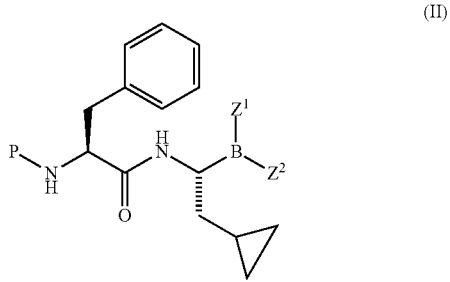

(II)

or a pharmaceutically acceptable salt or boronic acid anhydride thereof, wherein each of the variables P, $Z^1$, and $Z^2$ has the values and preferred values described above for formula (I).

In some embodiments, the invention relates to a compound of formula (II), wherein P has the formula $R^D$—C(O)—, where $R^D$ is a substituted or unsubstituted phenyl, pyridinyl, pyrazinyl, pyrimidinyl, quinolinyl, or quinoxalinyl. In certain embodiments, P has the formula $R^D$—C(O)—, where $R^D$ is a phenyl, pyridinyl, pyrazinyl, pyrimidinyl, naphthyl, quinolinyl, quinoxalinyl, benzimidazolyl, or dihydrobenzoxazinyl substituted with 0-1 $R^d$ and 0-2 $R^{8d}$. In certain particular embodiments, P has the formula $R^D$—C(O)—, where $R^D$ is a phenyl, or pyrazinyl, substituted with 0-1 $R^d$ and 0-2 $R^{8d}$. In some such embodiments, $R^d$ is a substituted or unsubstituted aryl, heteroaryl, heterocyclyl, or cycloaliphatic ring, and each $R^{8d}$ independently is $C_{14}$ aliphatic, $C_{1-4}$ fluoroaliphatic, or halo.

In certain particular embodiments, P has the formula $R^D$—C(O)—, where $R^D$ is a pyridinyl, pyrazinyl, or pyrimidinyl, which is substituted with a substituent of formula —O—$R^E$, and $R^E$ is a substituted or unsubstituted phenyl. In certain other particular embodiments, P has the formula $R^D$—C(O)—, where $R^D$ is a phenyl, which is substituted with a substituent of formula —O—$R^E$, and $R^E$ is a substituted or unsubstituted pyridinyl, pyrazinyl, or pyrimidinyl.

In some other embodiments, the invention relates to a compound of formula (II), wherein P has the formula $R^c$—$SO_2$—, where $R^c$ is —$R^D$ or -$T^1$-$R^D$, where $T^1$ is $C_{1-4}$ alkylene and $R^D$ is a phenyl, pyridinyl, pyrazinyl, pyrimidinyl, naphthyl, quinolinyl, isoquinolinyl, quinoxalinyl, benzimidazolyl, benzothiazolyl, indolyl, oxodihydroindolyl, oxodihydrobenzoxazinyl, or dihydrobenzoxazinyl substituted with 0-1 $R^d$ and 0-2 $R^{8d}$. In some embodiments, P has the formula $R^D$—$SO_2$—, where $R^D$ is a substituted or unsubstituted phenyl, pyridinyl, pyrazinyl, pyrimidinyl, quinolinyl, isoquinolinyl, quinoxalinyl, benzimidazolyl, benzothiazolyl, indolyl, oxodihydroindolyl, oxodihydrobenzoxazinyl, or dihydrobenzoxazinyl. In certain embodiments, P has the formula $R^D$—$SO_2$—, where $R^D$ is a phenyl, pyridinyl, pyrazinyl, isoquinolinyl, benzothiazolyl, indolyl, oxodihydroindolyl, oxodihydrobenzoxazinyl, or dihydrobenzoxazinyl substituted with 0-1 $R^d$ and 0-2 $R^{8d}$. In some such embodiments, $R^d$ is a substituted or unsubstituted aryl, heteroaryl, heterocyclyl, or cycloaliphatic ring, and each $R^{8d}$ independently is $C_{1-4}$ aliphatic, $C_{1-4}$ fluoroaliphatic, or halo. In certain embodiments, P has the formula $R^D$—$SO_2$—, where $R^D$ is a phenyl substituted with 0-1 $R^d$, and $R^d$ is a substituted or unsubstituted aryl, heteroaryl, heterocyclyl, or cycloaliphatic ring. In certain such embodiments, P has the formula $R^D$—$SO_2$—, where $R^D$ is a phenyl substituted with 1 $R^d$, and $R^d$ is a substituted or unsubstituted oxazolyl, thiazolyl, or imidazolyl; wherein if substituted, $R^d$ is substituted with 1 $R^{dd}$; and $R^{dd}$ is methyl, ethyl, trifluoromethyl, chloro, or fluoro.

In certain particular embodiments, P has the formula $R^D$—$SO_2$—, where $R^D$ is a pyridinyl, pyrazinyl, or pyrimidinyl, which is substituted with a substituent of formula —O—$R^E$, and $R^E$ is a substituted or unsubstituted phenyl. In certain other particular embodiments, P has the formula $R^D$—$SO_2$—, where $R^D$ is a phenyl, which is substituted with a substituent of formula —O—$R^E$, and $R^E$ is a substituted or unsubstituted pyridinyl, pyrazinyl, pyrimidinyl, quinolinyl, benzothiazolyl, benzimidazolyl, or indolyl. In certain such embodiments, $R^E$ is a substituted or unsubstituted pyridinyl, pyrazinyl, pyrimidinyl, quinolinyl, benzothiazolyl, benzimidazolyl, or indolyl; wherein if substituted, $R^E$ is substituted with 1-2 $R^{dd}$. In some such embodiments, each $R^{dd}$ is independently $C_{14}$ aliphatic, $C_{1-4}$ fluoroaliphatic, or halo. In certain such embodiments, $R^E$ is a substituted or unsubstituted pyridinyl; wherein if substituted, $R^E$ is substituted with 1 $R^{dd}$. In some such embodiments, $R^{dd}$ is methyl, ethyl, trifluoromethyl, chloro, or fluoro.

In certain particular embodiments, P has the formula $R^D$—$SO_2$—, where $R^D$ is phenyl, which is substituted with a substituent of formula —C(O)—$R^E$, and $R^E$ is a substituted or unsubstituted pyridinyl, pyrazinyl, or pyrimidinyl. In certain such embodiments, $R^E$ is a substituted or unsubstituted pyridinyl, pyrazinyl, or pyrimidinyl; wherein if substituted, $R^E$ is substituted with 1-2 $R^{dd}$. In some such embodiments, each $R^{dd}$ is independently $C_{14}$ aliphatic, $C_{1-4}$ fluoroaliphatic, or halo. In certain such embodiments, $R^E$ is a substituted or unsubstituted pyridinyl; wherein if substituted, $R^E$ is substituted with 1 $R^{dd}$. In some such embodiments, $R^{dd}$ is methyl, ethyl, trifluoromethyl, chloro, or fluoro.

In certain other particular embodiments, P has the formula $R^D$—$SO_2$—, where $R^D$ is phenyl, which is substituted with a substitutent of formula —S(O)—$R^E$, and $R^E$ is a substituted or unsubstituted pyridinyl, pyrazinyl, or pyrimidinyl. In certain other particular embodiments, P has the formula $R^D$—$SO_2$—, where $R^D$ is phenyl, which is substituted with a substitutent of formula —$S(O)_2$—$R^E$, and $R^E$ is a substituted or unsubstituted pyridinyl, pyrazinyl, or pyrimidinyl. In certain other particular embodiments, P has the formula $R^D$—$SO_2$—, where $R^D$ is phenyl, which is substituted with a substituent of formula —NH—$R^E$, and $R^E$ is a substituted or unsubstituted pyridinyl, pyrazinyl, or pyrimidinyl.

In certain embodiments, the invention relates to a compound of formula (I), characterized by formula (II):

(II)

or a pharmaceutically acceptable salt or boronic acid anhydride thereof, wherein each of the variables $Z^1$ and $Z^2$ has the values and preferred values described herein for formula (I);

P is $R^D$—SO$_2$—;
$R^D$ is phenyl substituted with 0-1 $R^d$; and
$R^d$ is a substituted or unsubstituted aryl, heteroaryl, heterocyclyl, or cycloaliphatic ring.

In certain such embodiments:
$R^D$ is phenyl substituted with 1 $R^d$;
$R^d$ is substituted or unsubstituted oxazolyl, thiazolyl, or imidazolyl;
wherein if substituted, $R^d$ is substituted with 1 $R^{dd}$; and
$R^{dd}$ is methyl, ethyl, trifluoromethyl, chloro, or fluoro.

In certain embodiments, the invention relates to a compound of formula (I), characterized by formula (II):

(II)

or a pharmaceutically acceptable salt or boronic acid anhydride thereof, wherein each of the variables $Z^1$ and $Z^2$ has the values and preferred values described herein for formula (I);

P is $R^D$—SO$_2$—;
$R^D$ is a phenyl substituted with —O—$R^E$;
$R^E$ is a substituted or unsubstituted pyridinyl, pyrazinyl, pyrimidinyl, quinolinyl, benzothiazolyl, benzimidazolyl, or indolyl;
wherein if substituted, $R^E$ is substituted with 1-2 $R^{dd}$; and
each $R^{dd}$ is independently $C_{1-4}$ aliphatic, $C_{1-4}$ fluoroaliphatic, or halo.

In certain such embodiments:
$R^E$ is a substituted or unsubstituted pyridinyl;
wherein if substituted, $R^E$ is substituted with 1 $R^{dd}$; and
$R^{dd}$ is methyl, ethyl, trifluoromethyl, chloro, or fluoro.

In certain embodiments, the invention relates to a compound of formula (I), characterized by formula (II):

(II)

or a pharmaceutically acceptable salt or boronic acid anhydride thereof, wherein each of the variables $Z^1$ and $Z^2$ has the values and preferred values described herein for formula (I);

P is $R^D$—SO$_2$—;
$R^D$ is a phenyl substituted with —C(O)—$R^E$,
$R^E$ is a substituted or unsubstituted pyridinyl, pyrazinyl, or pyrimidinyl;
wherein if substituted, $R^E$ is substituted with 1-2 $R^{dd}$; and
each $R^{dd}$ is independently $C_{1-4}$ aliphatic, $C_{1-4}$ fluoroaliphatic, or halo.

In certain such embodiments:
$R^E$ is a substituted or unsubstituted pyridinyl;
wherein if substituted, $R^E$ is substituted with 1 $R^{dd}$; and
$R^{dd}$ is methyl, ethyl, trifluoromethyl, chloro, or fluoro.

Representative examples of compounds of formula (I) are shown in Table 1.

TABLE 1

Proteasome Inhibitors

1

2

TABLE 1-continued
Proteasome Inhibitors
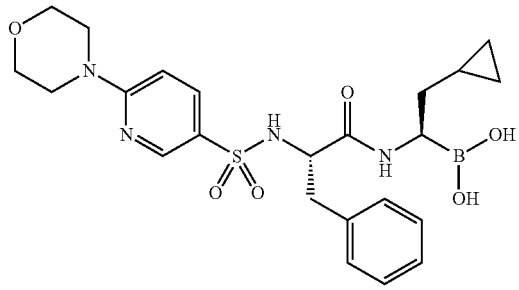 [SMILES: O=C(N[C@@H](CC1CC1)B(O)O)[C@H](Cc1ccccc1)NS(=O)(=O)c1ccc(N2CCOCC2)nc1]
3
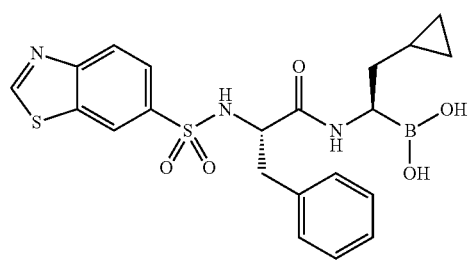 [SMILES: O=C(N[C@@H](CC1CC1)B(O)O)[C@H](Cc1ccccc1)NS(=O)(=O)c1ccc2ncsc2c1]
4
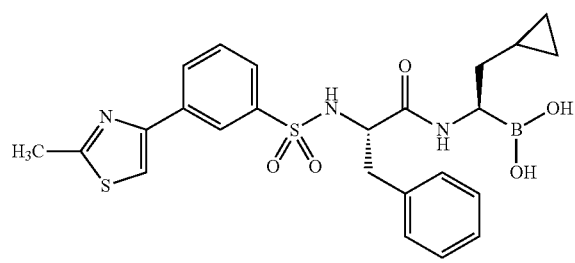 [SMILES: Cc1nc(-c2cccc(S(=O)(=O)N[C@@H](Cc3ccccc3)C(=O)N[C@@H](CC3CC3)B(O)O)c2)cs1]
5
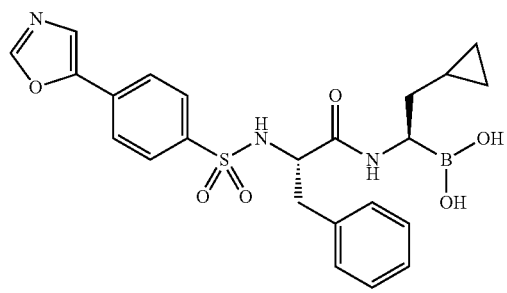 [SMILES: O=C(N[C@@H](CC1CC1)B(O)O)[C@H](Cc1ccccc1)NS(=O)(=O)c1ccc(-c2cnco2)cc1]
6
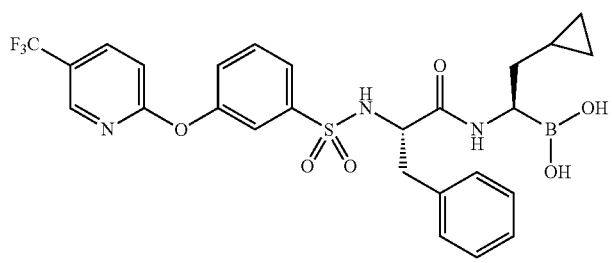 [SMILES: O=C(N[C@@H](CC1CC1)B(O)O)[C@H](Cc1ccccc1)NS(=O)(=O)c1cccc(Oc2ccc(C(F)(F)F)cn2)c1]
7

TABLE 1-continued
Proteasome Inhibitors
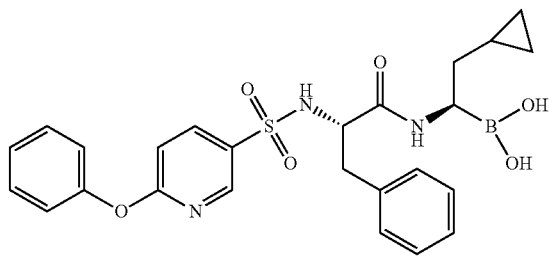 [SMILES: O=C(N[C@@H](CC1CC1)B(O)O)[C@H](Cc1ccccc1)NS(=O)(=O)c1ccc(Oc2ccccc2)nc1]
8
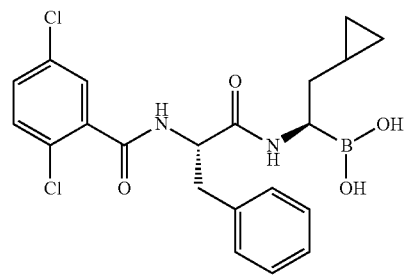 [SMILES: O=C(N[C@@H](Cc1ccccc1)C(=O)N[C@@H](CC1CC1)B(O)O)c1cc(Cl)ccc1Cl]
9
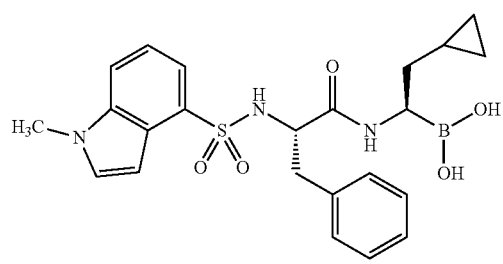 [SMILES: Cn1ccc2c(S(=O)(=O)N[C@@H](Cc3ccccc3)C(=O)N[C@@H](CC3CC3)B(O)O)cccc21]
10
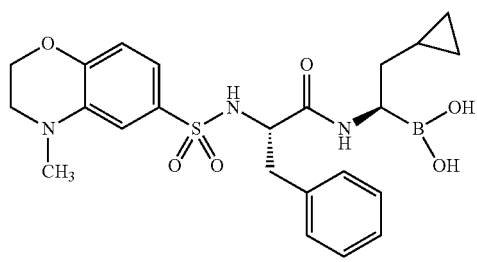 [SMILES: CN1CCOc2ccc(S(=O)(=O)N[C@@H](Cc3ccccc3)C(=O)N[C@@H](CC3CC3)B(O)O)cc21]
11
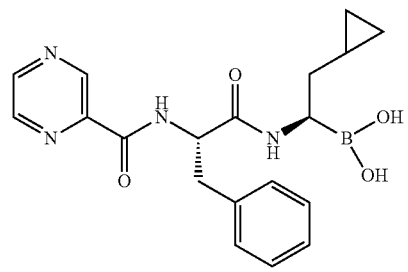 [SMILES: O=C(N[C@@H](Cc1ccccc1)C(=O)N[C@@H](CC1CC1)B(O)O)c1cnccn1]
12
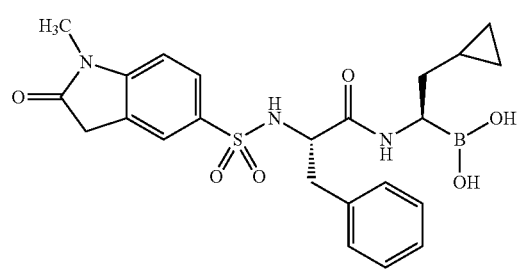 [SMILES: CN1C(=O)Cc2cc(S(=O)(=O)N[C@@H](Cc3ccccc3)C(=O)N[C@@H](CC3CC3)B(O)O)ccc21]
13

TABLE 1-continued
Proteasome Inhibitors
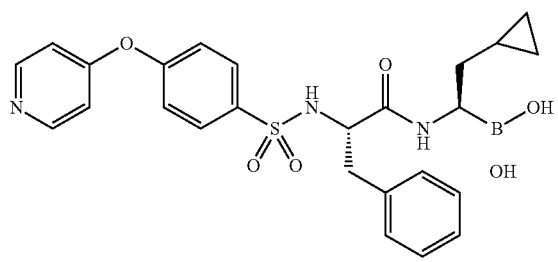
14
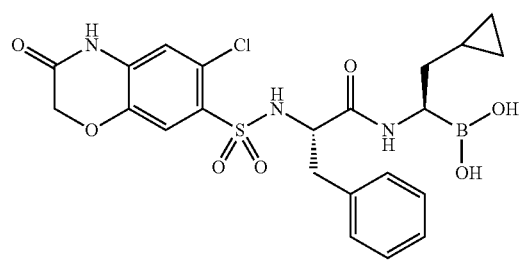 [SMILES: O=C1COc2cc(S(=O)(=O)N[C@@H](Cc3ccccc3)C(=O)N[C@@H](CC3CC3)B(O)O)c(Cl)cc2N1]
15
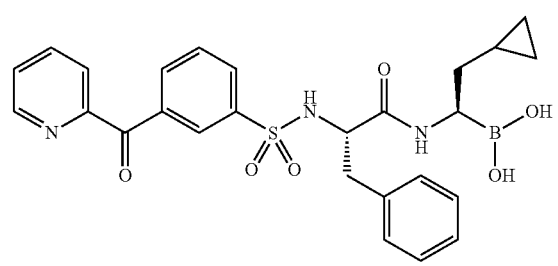 [SMILES: O=C(c1cccc(S(=O)(=O)N[C@@H](Cc2ccccc2)C(=O)N[C@@H](CC2CC2)B(O)O)c1)c1ccccn1]
16
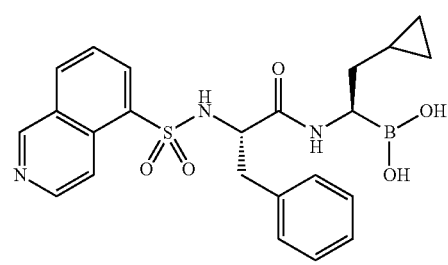 [SMILES: O=C(N[C@@H](CC1CC1)B(O)O)[C@H](Cc1ccccc1)NS(=O)(=O)c1cccc2cnccc12]
17
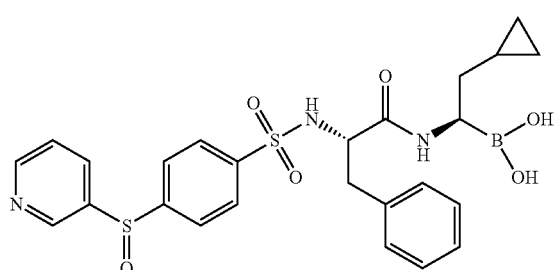
18
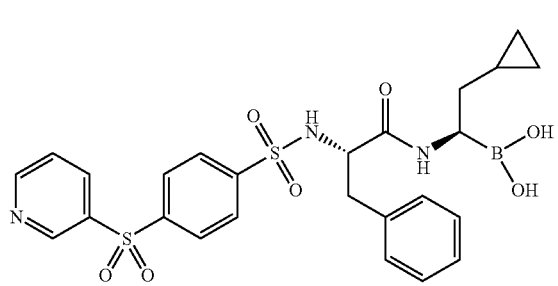 [SMILES: O=C(N[C@@H](CC1CC1)B(O)O)[C@H](Cc1ccccc1)NS(=O)(=O)c1ccc(S(=O)(=O)c2cccnc2)cc1]
19

TABLE 1-continued
Proteasome Inhibitors
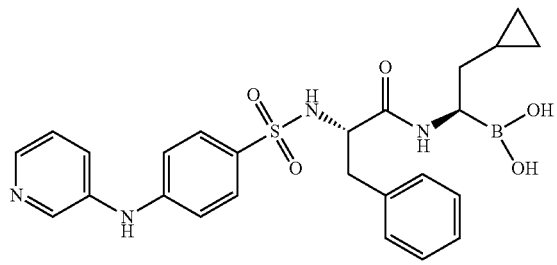 [SMILES: O=C(N[C@@H](CC1CC1)B(O)O)[C@H](Cc1ccccc1)NS(=O)(=O)c1ccc(Nc2cccnc2)cc1]
20
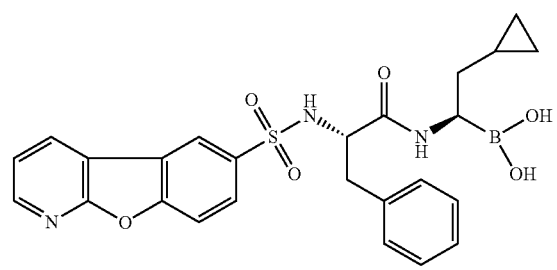 [SMILES: O=C(N[C@@H](CC1CC1)B(O)O)[C@H](Cc1ccccc1)NS(=O)(=O)c1ccc2oc3ncccc3c2c1]
21
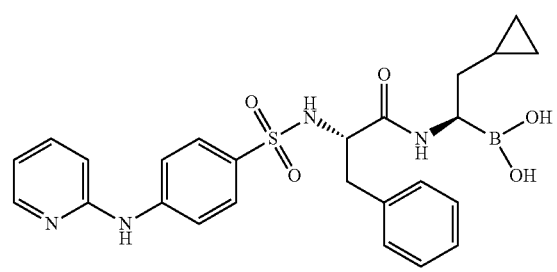 [SMILES: O=C(N[C@@H](CC1CC1)B(O)O)[C@H](Cc1ccccc1)NS(=O)(=O)c1ccc(Nc2ccccn2)cc1]
22
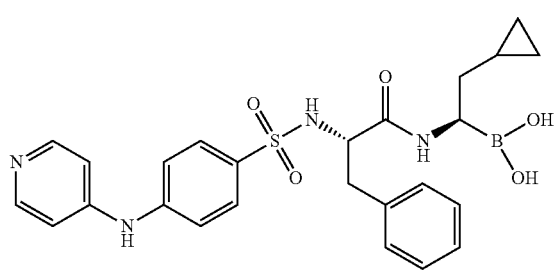 [SMILES: O=C(N[C@@H](CC1CC1)B(O)O)[C@H](Cc1ccccc1)NS(=O)(=O)c1ccc(Nc2ccncc2)cc1]
23
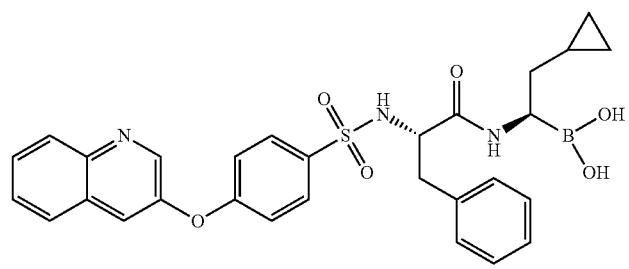 [SMILES: O=C(N[C@@H](CC1CC1)B(O)O)[C@H](Cc1ccccc1)NS(=O)(=O)c1ccc(Oc2cnc3ccccc3c2)cc1]
24

TABLE 1-continued
Proteasome Inhibitors
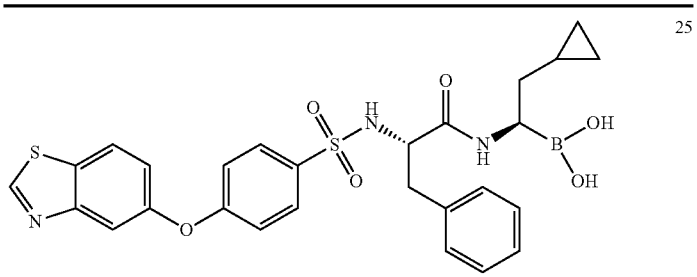
25
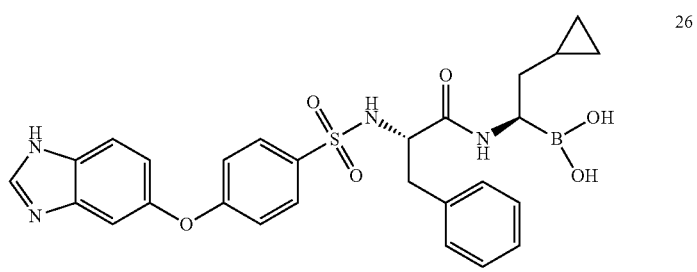
26
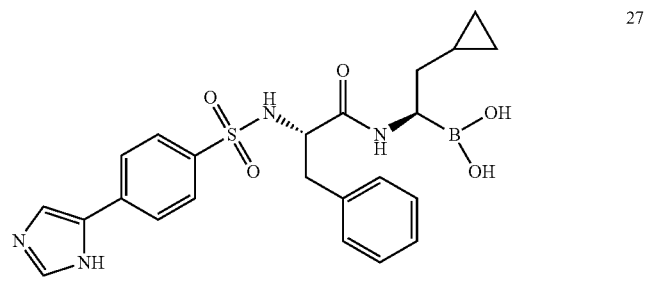
27
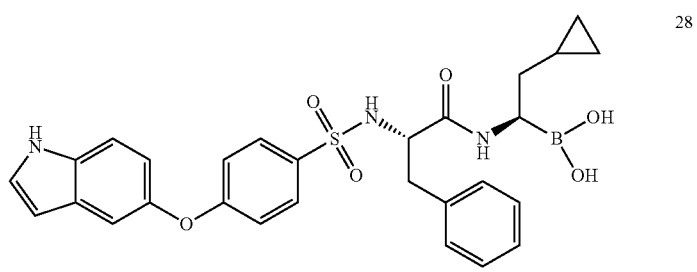
28
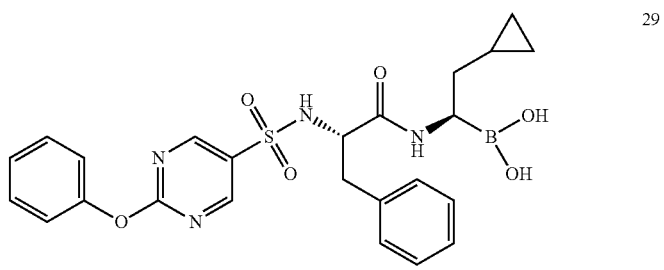
29

TABLE 1-continued

Proteasome Inhibitors

30

31

32

33

The compounds in Table 1 above may also be identified by the following chemical names:

1. ((1R)-2-cyclopropyl-1-{[(2S)-3-phenyl-2-({[4-(pyridin-2-yloxy)phenyl]sulfonyl}amino)propanoyl]amino}ethyl)boronic acid
2. ((1R)-2-cyclopropyl-1-{[(2S)-3-phenyl-2-({[4-(pyridin-3-yloxy)phenyl]sulfonyl}amino)propanoyl]amino}ethyl)boronic acid
3. {(1R)-2-cyclopropyl-1-[((2S)-2-{[(6-morpholin-4-ylpyridin-3-yl)sulfonyl]amino}-3-phenylpropanoyl)amino]ethyl}boronic acid
4. [(1R)-1-({(2S)-2-[(1,3-benzothiazol-6-ylsulfonyl)amino]-3-phenylpropanoyl}amino)-2-cyclopropylethyl]boronic acid
5. ((1R)-2-cyclopropyl-1-{[(2S)-2-({[3-(2-methyl-1,3-thiazol-4-yl)phenyl]sulfonyl}amino)-3-phenylpropanoyl]amino}ethyl)boronic acid
6. ((1R)-2-cyclopropyl-1-{[(2S)-2-({[4-(1,3-oxazol-5-yl)phenyl]sulfonyl}amino)-3-phenylpropanoyl]amino}ethyl)boronic acid
7. {(1R)-2-cyclopropyl-1-[((2S)-3-phenyl-2-{[(3-{[5-(trifluoromethyl)pyridin-2-yl]oxy}phenyl)sulfonyl]amino}propanoyl)amino]ethyl}boronic acid
8. {(1R)-2-cyclopropyl-1-[((2S)-2-{[(6-phenoxypyridin-3-yl)sulfonyl]amino}-3-phenylpropanoyl)amino]ethyl}boronic acid
9. [(1R)-2-cyclopropyl-1-({(2S)-2-[(2,5-dichlorobenzoyl)amino]-3-phenylpropanoyl}amino)ethyl]boronic acid
10. {(1R)-2-cyclopropyl-1-[((2S)-2-{[(1-methyl-1H-indol-4-yl)sulfonyl]amino}-3-phenylpropanoyl)amino]ethyl}boronic acid
11. {(1R)-2-cyclopropyl-1-[((2S)-2-{[(4-methyl-3,4-dihydro-2H-1,4-benzoxazin-6-yl)sulfonyl]amino}-3-phenylpropanoyl)amino]ethyl}boronic acid
12. [(1R)-2-cyclopropyl-1-({(2S)-3-phenyl-2-[(pyrazin-2-ylcarbonyl)amino]propanoyl}amino)ethyl]boronic acid
13. {(1R)-2-cyclopropyl-1-[((2S)-2-{[(1-methyl-2-oxo-2,3-dihydro-1H-indol-5-yl)sulfonyl]amino}-3-phenylpropanoyl)amino]ethyl}boronic acid
14. ((1R)-2-cyclopropyl-1-{[(2S)-3-phenyl-2-({[4-(pyridin-4-yloxy)phenyl]sulfonyl}amino)propanoyl]amino}ethyl)boronic acid
15. {(1R)-1-[((2S)-2-{[(6-chloro-3-oxo-3,4-dihydro-2H-1,4-benzoxazin-7-yl)sulfonyl]amino}-3-phenylpropanoyl)amino]-2-cyclopropylethyl}boronic acid 16 ((1R)-2-cyclopropyl-1-{[(2S)-3-phenyl-2-({[3-(pyridin-2-ylcarbonyl)phenyl]sulfonyl}amino)propanoyl]amino}ethyl)boronic acid
17 [(1R)-2-cyclopropyl-1-({(2S)-2-[(isoquinolin-5-ylsulfonyl)amino]-3-phenylpropanoyl}amino)ethyl]boronic acid
18 ((1R)-2-cyclopropyl-1-{[(2S)-3-phenyl-2-({[4-(pyridin-3-ylsulfinyl)phenyl]sulfonyl}amino)propanoyl]amino}ethyl)boronic acid
19 ((1R)-2-cyclopropyl-1-{[(2S)-3-phenyl-2-({[4-(pyridin-3-ylsulfonyl)phenyl]sulfonyl}amino)propanoyl]amino}ethyl)boronic acid
20 ((1R)-2-cyclopropyl-1-{[(2S)-3-phenyl-2-({[4-(pyridin-3-ylamino)phenyl]sulfonyl}amino)propanoyl]amino}ethyl)boronic acid
21 [(1R)-1-({(2S)-2-[([1]benzofuro[2,3-b]pyridin-6-ylsulfonyl)amino]-3-phenylpropanoyl}amino)-2-cyclopropylethyl]boronic acid
22 ((1R)-2-cyclopropyl-1-{[(2S)-3-phenyl-2-({[4-(pyridin-2-ylamino)phenyl]sulfonyl}amino)propanoyl]amino}ethyl)boronic acid
23 ((1R)-2-cyclopropyl-1-{[(2S)-3-phenyl-2-({[4-(pyridin-4-ylamino)phenyl]sulfonyl}amino)propanoyl]amino}ethyl)boronic acid
24 ((1R)-2-cyclopropyl-1-{[(2S)-3-phenyl-2-({[4-(quinolin-3-yloxy)phenyl]sulfonyl}amino)propanoyl]amino}ethyl)boronic acid
25 ((1R)-1-{[(2S)-2-({[4-(1,3-benzothiazol-5-yloxy)phenyl]sulfonyl}amino)-3-phenylpropanoyl]amino}-2-cyclopropylethyl)boronic acid
26 ((1R)-1-{[(2S)-2-({[4-(1H-benzimidazol-5-yloxy)phenyl]sulfonyl}amino)-3-phenylpropanoyl]amino}-2-cyclopropylethyl)boronic acid
27 ((1R)-2-cyclopropyl-1-{[(2S)-2-({[4-(1H-imidazol-5-yl)phenyl]sulfonyl}amino)-3-phenylpropanoyl]amino}ethyl)boronic acid
28 ((1R)-2-cyclopropyl-1-{[(2S)-2-({[4-(1H-indol-5-yloxy)phenyl]sulfonyl}amino)-3-phenylpropanoyl]amino}ethyl)boronic acid
29 {(1R)-2-cyclopropyl-1-[((2S)-2-{[(2-phenoxypyrimidin-5-yl)sulfonyl]amino}-3-phenylpropanoyl)amino]ethyl}boronic acid
30 ((1R)-2-cyclopropyl-1-{[(2S)-3-phenyl-2-({[4-(pyrimidin-2-yloxy)phenyl]sulfonyl}amino)propanoyl]amino}ethyl)boronic acid
31 {(1R)-2-cyclopropyl-1-[((2S)-2-{[(5-phenoxypyrazin-2-yl)sulfonyl]amino}-3-phenylpropanoyl)amino]ethyl}boronic acid
32 ((1R)-2-cyclopropyl-1-{[(2S)-3-phenyl-2-({[4-(pyrazin-2-yloxy)phenyl]sulfonyl}amino)propanoyl]amino}ethyl)boronic acid
33 {(1R)-2-cyclopropyl-1-[((2S)-2-{[(5-phenoxypyridin-2-yl)sulfonyl]amino}-3-phenylpropanoyl)amino]ethyl}boronic acid The corresponding pinanediol esters, mannitol esters, and citrate esters of each of the Compounds 1-33 are listed in Table 2 below. For example, Compound 1-A is the corresponding pinanediol ester of Compound 1; Compound 1-B is the corresponding mannitol ester of Compound 1; Compound 1-C is the corresponding citrate ester of Compound 1, and so on. The pinanediol esters and mannitol esters may be synthesized by procedures outlined in the Experimental Section below. The citrate esters may be synthesized by procedures described in Elliott et al., WO 09/154,737, herein incorporated by reference.

TABLE 2

| | Proteasome Inhibitors |
|---|---|
| 1-A | ((1R)-2-cyclopropyl-1-{[(2S)-3-phenyl-2-({[4-(pyridin-2-yloxy)phenyl]sulfonyl}amino)propanoyl]amino}ethyl)boronic acid pinanediol ester |
| 1-B | ((1R)-2-cyclopropyl-1-{[(2S)-3-phenyl-2-({[4-(pyridin-2-yloxy)phenyl]sulfonyl}amino)propanoyl]amino}ethyl)boronic acid D-mannitol ester |
| 1-C | ((1R)-2-cyclopropyl-1-{[(2S)-3-phenyl-2-({[4-(pyridin-2-yloxy)phenyl]sulfonyl}amino)propanoyl]amino}ethyl)boronic acid citrate ester |
| 2-A | ((1R)-2-cyclopropyl-1-{[(2S)-3-phenyl-2-({[4-(pyridin-3-yloxy)phenyl]sulfonyl}amino)propanoyl]amino}ethyl)boronic acid pinanediol ester |
| 2-B | ((1R)-2-cyclopropyl-1-{[(2S)-3-phenyl-2-({[4-(pyridin-3-yloxy)phenyl]sulfonyl}amino)propanoyl]amino}ethyl)boronic acid D-mannitol ester |
| 2-C | ((1R)-2-cyclopropyl-1-{[(2S)-3-phenyl-2-({[4-(pyridin-3-yloxy)phenyl]sulfonyl}amino)propanoyl]amino}ethyl)boronic acid citrate ester |
| 3-A | {(1R)-2-cyclopropyl-1-[((2S)-2-{[(6-morpholin-4-ylpyridin-3-yl)sulfonyl]amino}-3-phenylpropanoyl)amino]ethyl}boronic acid pinanediol ester |
| 3-B | {(1R)-2-cyclopropyl-1-[((2S)-2-{[(6-morpholin-4-ylpyridin-3-yl)sulfonyl]amino}-3-phenylpropanoyl)amino]ethyl}boronic acid D-mannitol ester |
| 3-C | {(1R)-2-cyclopropyl-1-[((2S)-2-{[(6-morpholin-4-ylpyridin-3-yl)sulfonyl]amino}-3-phenylpropanoyl)amino]ethyl}boronic acid citrate ester |
| 4-A | [(1R)-1-({(2S)-2-[(1,3-benzothiazol-6-ylsulfonyl)amino]-3-phenylpropanoyl}amino)-2-cyclopropylethyl]boronic acid pinanediol ester |
| 4-B | [(1R)-1-({(2S)-2-[(1,3-benzothiazol-6-ylsulfonyl)amino]-3-phenylpropanoyl}amino)-2-cyclopropylethyl]boronic acid D-mannitol ester |
| 4-C | [(1R)-1-({(2S)-2-[(1,3-benzothiazol-6-ylsulfonyl)amino]-3-phenylpropanoyl}amino)-2-cyclopropylethyl]boronic acid citrate ester |
| 5-A | ((1R)-2-cyclopropyl-1-{[(2S)-2-({[3-(2-methyl-1,3-thiazol-4-yl)phenyl]sulfonyl}amino)-3-phenylpropanoyl]amino}ethyl)boronic acid pinanediol ester |
| 5-B | ((1R)-2-cyclopropyl-1-{[(2S)-2-({[3-(2-methyl-1,3-thiazol-4-yl)phenyl]sulfonyl}amino)-3-phenylpropanoyl]amino}ethyl)boronic acid D-mannitol ester |
| 5-C | ((1R)-2-cyclopropyl-1-{[(2S)-2-({[3-(2-methyl-1,3-thiazol-4-yl)phenyl]sulfonyl}amino)-3-phenylpropanoyl]amino}ethyl)boronic acid citrate ester |
| 6-A | ((1R)-2-cyclopropyl-1-{[(2S)-2-({[4-(1,3-oxazol-5-yl)phenyl]sulfonyl}amino)-3-phenylpropanoyl]amino}ethyl)boronic acid pinanediol ester |

TABLE 2-continued

Proteasome Inhibitors

| | |
|---|---|
| 6-B | ((1R)-2-cyclopropyl-1-{[(2S)-2-({[4-(1,3-oxazol-5-yl)phenyl]sulfonyl}amino)-3-phenylpropanoyl]amino}ethyl)boronic acid D-mannitol ester |
| 6-C | ((1R)-2-cyclopropyl-1-{[(2S)-2-({[4-(1,3-oxazol-5-yl)phenyl]sulfonyl}amino)-3-phenylpropanoyl]amino}ethyl)boronic acid citrate ester |
| 7-A | {(1R)-2-cyclopropyl-1-[((2S)-3-phenyl-2-{[(3-{[5-(trifluoromethyl)pyridin-2-yl]oxy}phenyl)sulfonyl]amino}propanoyl)amino]ethyl}boronic acid pinanediol ester |
| 7-B | {(1R)-2-cyclopropyl-1-[((2S)-3-phenyl-2-{[(3-{[5-(trifluoromethyl)pyridin-2-yl]oxy}phenyl)sulfonyl]amino}propanoyl)amino]ethyl}boronic acid D-mannitol ester |
| 7-C | {(1R)-2-cyclopropyl-1-[((2S)-3-phenyl-2-{[(3-{[5-(trifluoromethyl)pyridin-2-yl]oxy}phenyl)sulfonyl]amino}propanoyl)amino]ethyl}boronic acid citrate ester |
| 8-A | {(1R)-2-cyclopropyl-1-[((2S)-2-{[(6-phenoxypyridin-3-yl)sulfonyl]amino}-3-phenylpropanoyl)amino]ethyl}boronic acid pinanediol ester |
| 8-B | {(1R)-2-cyclopropyl-1-[((2S)-2-{[(6-phenoxypyridin-3-yl)sulfonyl]amino}-3-phenylpropanoyl)amino]ethyl}boronic acid D-mannitol ester |
| 8-C | {(1R)-2-cyclopropyl-1-[((2S)-2-{[(6-phenoxypyridin-3-yl)sulfonyl]amino}-3-phenylpropanoyl)amino]ethyl}boronic acid citrate ester |
| 9-A | [(1R)-2-cyclopropyl-1-({(2S)-2-[(2,5-dichlorobenzoyl)amino]-3-phenylpropanoyl}amino)ethyl]boronic acid pinanediol ester |
| 9-B | [(1R)-2-cyclopropyl-1-({(2S)-2-[(2,5-dichlorobenzoyl)amino]-3-phenylpropanoyl}amino)ethyl]boronic acid D-mannitol ester |
| 9-C | [(1R)-2-cyclopropyl-1-({(2S)-2-[(2,5-dichlorobenzoyl)amino]-3-phenylpropanoyl}amino)ethyl]boronic acid citrate ester |
| 10-A | {(1R)-2-cyclopropyl-1-[((2S)-2-{[(1-methyl-1H-indol-4-yl)sulfonyl]amino}-3-phenylpropanoyl)amino]ethyl}boronic acid pinanediol ester |
| 10-B | {(1R)-2-cyclopropyl-1-[((2S)-2-{[(1-methyl-1H-indol-4-yl)sulfonyl]amino}-3-phenylpropanoyl)amino]ethyl}boronic acid D-mannitol ester |
| 10-C | {(1R)-2-cyclopropyl-1-[((2S)-2-{[(1-methyl-1H-indol-4-yl)sulfonyl]amino}-3-phenylpropanoyl)amino]ethyl}boronic acid citrate ester |
| 11-A | {(1R)-2-cyclopropyl-1-[((2S)-2-{[(4-methyl-3,4-dihydro-2H-1,4-benzoxazin-6-yl)sulfonyl]amino}-3-phenylpropanoyl)amino]ethyl}boronic acid pinanediol ester |
| 11-B | {(1R)-2-cyclopropyl-1-[((2S)-2-{[(4-methyl-3,4-dihydro-2H-1,4-benzoxazin-6-yl)sulfonyl]amino}-3-phenylpropanoyl)amino]ethyl}boronic acid D-mannitol ester |
| 11-C | {(1R)-2-cyclopropyl-1-[((2S)-2-{[(4-methyl-3,4-dihydro-2H-1,4-benzoxazin-6-yl)sulfonyl]amino}-3-phenylpropanoyl)amino]ethyl}boronic acid citrate ester |
| 12-A | [(1R)-2-cyclopropyl-1-({(2S)-3-phenyl-2-[(pyrazin-2-ylcarbonyl)amino]propanoyl}amino)ethyl]boronic acid pinanediol ester |
| 12-B | [(1R)-2-cyclopropyl-1-({(2S)-3-phenyl-2-[(pyrazin-2-ylcarbonyl)amino]propanoyl}amino)ethyl]boronic acid D-mannitol ester |
| 12-C | [(1R)-2-cyclopropyl-1-({(2S)-3-phenyl-2-[(pyrazin-2-ylcarbonyl)amino]propanoyl}amino)ethyl]boronic acid citrate ester |
| 13-A | {(1R)-2-cyclopropyl-1-[((2S)-2-{[(1-methyl-2-oxo-2,3-dihydro-1H-indol-5-yl)sulfonyl]amino}-3-phenylpropanoyl)amino]ethyl}boronic acid pinanediol ester |
| 13-B | {(1R)-2-cyclopropyl-1-[((2S)-2-{[(1-methyl-2-oxo-2,3-dihydro-1H-indol-5-yl)sulfonyl]amino}-3-phenylpropanoyl)amino]ethyl}boronic acid D-mannitol ester |
| 13-C | {(1R)-2-cyclopropyl-1-[((2S)-2-{[(1-methyl-2-oxo-2,3-dihydro-1H-indol-5-yl)sulfonyl]amino}-3-phenylpropanoyl)amino]ethyl}boronic acid citrate ester |
| 14-A | ((1R)-2-cyclopropyl-1-{[(2S)-3-phenyl-2-({[4-(pyridin-4-yloxy)phenyl]sulfonyl}amino)propanoyl]amino}ethyl)boronic acid pinanediol ester |
| 14-B | ((1R)-2-cyclopropyl-1-{[(2S)-3-phenyl-2-({[4-(pyridin-4-yloxy)phenyl]sulfonyl}amino)propanoyl]amino}ethyl)boronic acid D-mannitol ester |
| 14-C | ((1R)-2-cyclopropyl-1-{[(2S)-3-phenyl-2-({[4-(pyridin-4-yloxy)phenyl]sulfonyl}amino)propanoyl]amino}ethyl)boronic acid citrate ester |
| 15-A | {(1R)-1-[((2S)-2-{[(6-chloro-3-oxo-3,4-dihydro-2H-1,4-benzoxazin-7-yl)sulfonyl]amino}-3-phenylpropanoyl)amino]-2-cyclopropylethyl}boronic acid pinanediol ester |
| 15-B | {(1R)-1-[((2S)-2-{[(6-chloro-3-oxo-3,4-dihydro-2H-1,4-benzoxazin-7-yl)sulfonyl]amino}-3-phenylpropanoyl)amino]-2-cyclopropylethyl}boronic acid D-mannitol ester |
| 15-C | {(1R)-1-[((2S)-2-{[(6-chloro-3-oxo-3,4-dihydro-2H-1,4-benzoxazin-7-yl)sulfonyl]amino}-3-phenylpropanoyl)amino]-2-cyclopropylethyl}boronic acid citrate ester |
| 16-A | ((1R)-2-cyclopropyl-1-{[(2S)-3-phenyl-2-({[3-(pyridin-2-ylcarbonyl)phenyl]sulfonyl}amino)propanoyl]amino}ethyl)boronic acid pinanediol ester |

TABLE 2-continued

Proteasome Inhibitors

| | |
|---|---|
| 16-B | ((1R)-2-cyclopropyl-1-{[(2S)-3-phenyl-2-({[3-(pyridin-2-ylcarbonyl)phenyl]sulfonyl}amino)propanoyl]amino}ethyl)boronic acid D-mannitol ester |
| 16-C | ((1R)-2-cyclopropyl-1-{[(2S)-3-phenyl-2-({[3-(pyridin-2-ylcarbonyl)phenyl]sulfonyl}amino)propanoyl]amino}ethyl)boronic acid citrate ester |
| 17-A | [(1R)-2-cyclopropyl-1-({(2S)-2-[(isoquinolin-5-ylsulfonyl)amino]-3-phenylpropanoyl}amino)ethyl]boronic acid pinanediol ester |
| 17-B | [(1R)-2-cyclopropyl-1-({(2S)-2-[(isoquinolin-5-ylsulfonyl)amino]-3-phenylpropanoyl}amino)ethyl]boronic acid D-mannitol ester |
| 17-C | [(1R)-2-cyclopropyl-1-({(2S)-2-[(isoquinolin-5-ylsulfonyl)amino]-3-phenylpropanoyl}amino)ethyl]boronic acid citrate ester |
| 18-A | ((1R)-2-cyclopropyl-1-{[(2S)-3-phenyl-2-({[4-(pyridin-3-ylsulfinyl)phenyl]sulfonyl}amino)propanoyl]amino}ethyl)boronic acid pinanediol ester |
| 18-B | ((1R)-2-cyclopropyl-1-{[(2S)-3-phenyl-2-({[4-(pyridin-3-ylsulfinyl)phenyl]sulfonyl}amino)propanoyl]amino}ethyl)boronic acid D-mannitol ester |
| 18-C | ((1R)-2-cyclopropyl-1-{[(2S)-3-phenyl-2-({[4-(pyridin-3-ylsulfinyl)phenyl]sulfonyl}amino)propanoyl]amino}ethyl)boronic acid citrate ester |
| 19-A | (1R)-2-cyclopropyl-1-{[(2S)-3-phenyl-2-({[4-(pyridin-3-ylsulfonyl)phenyl]sulfonyl}amino)propanoyl]amino}ethyl)boronic acid pinanediol ester |
| 19-B | (1R)-2-cyclopropyl-1-{[(2S)-3-phenyl-2-({[4-(pyridin-3-ylsulfonyl)phenyl]sulfonyl}amino)propanoyl]amino}ethyl)boronic acid D-mannitol ester |
| 19-C | (1R)-2-cyclopropyl-1-{[(2S)-3-phenyl-2-({[4-(pyridin-3-ylsulfonyl)phenyl]sulfonyl}amino)propanoyl]amino}ethyl)boronic acid citrate ester |
| 20-A | ((1R)-2-cyclopropyl-1-{[(2S)-3-phenyl-2-({[4-(pyridin-3-ylamino)phenyl]sulfonyl}amino)propanoyl]amino}ethyl)boronic acid pinanediol ester |
| 20-B | ((1R)-2-cyclopropyl-1-{[(2S)-3-phenyl-2-({[4-(pyridin-3-ylamino)phenyl]sulfonyl}amino)propanoyl]amino}ethyl)boronic acid D-mannitol ester |
| 20-C | ((1R)-2-cyclopropyl-1-{[(2S)-3-phenyl-2-({[4-(pyridin-3-ylamino)phenyl]sulfonyl}amino)propanoyl]amino}ethyl)boronic acid citrate ester |
| 21-A | [(1R)-1-({(2S)-2-[([1]benzofuro[2,3-b]pyridin-6-ylsulfonyl)amino]-3-phenylpropanoyl}amino)-2-cyclopropylethyl]boronic acid pinanediol ester |
| 21-B | [(1R)-1-({(2S)-2-[([1]benzofuro[2,3-b]pyridin-6-ylsulfonyl)amino]-3-phenylpropanoyl}amino)-2-cyclopropylethyl]boronic acid D-mannitol ester |
| 21-C | [(1R)-1-({(2S)-2-[([1]benzofuro[2,3-b]pyridin-6-ylsulfonyl)amino]-3-phenylpropanoyl}amino)-2-cyclopropylethyl]boronic acid citrate ester |
| 22-A | ((1R)-2-cyclopropyl-1-{[(2S)-3-phenyl-2-({[4-(pyridin-2-ylamino)phenyl]sulfonyl}amino)propanoyl]amino}ethyl)boronic acid pinanediol ester |
| 22-B | ((1R)-2-cyclopropyl-1-{[(2S)-3-phenyl-2-({[4-(pyridin-2-ylamino)phenyl]sulfonyl}amino)propanoyl]amino}ethyl)boronic acid D-mannitol ester |
| 22-C | ((1R)-2-cyclopropyl-1-{[(2S)-3-phenyl-2-({[4-(pyridin-2-ylamino)phenyl]sulfonyl}amino)propanoyl]amino}ethyl)boronic acid citrate ester |
| 23-A | ((1R)-2-cyclopropyl-1-{[(2S)-3-phenyl-2-({[4-(pyridin-4-ylamino)phenyl]sulfonyl}amino)propanoyl]amino}ethyl)boronic acid pinanediol ester |
| 23-B | ((1R)-2-cyclopropyl-1-{[(2S)-3-phenyl-2-({[4-(pyridin-4-ylamino)phenyl]sulfonyl}amino)propanoyl]amino}ethyl)boronic acid D-mannitol ester |
| 23-C | ((1R)-2-cyclopropyl-1-{[(2S)-3-phenyl-2-({[4-(pyridin-4-ylamino)phenyl]sulfonyl}amino)propanoyl]amino}ethyl)boronic acid citrate ester |
| 24-A | ((1R)-2-cyclopropyl-1-{[(2S)-3-phenyl-2-({[4-(quinolin-3-yloxy)phenyl]sulfonyl}amino)propanoyl]amino}ethyl)boronic acid pinanediol ester |
| 24-B | ((1R)-2-cyclopropyl-1-{[(2S)-3-phenyl-2-({[4-(quinolin-3-yloxy)phenyl]sulfonyl}amino)propanoyl]amino}ethyl)boronic acid D-mannitol ester |
| 24-C | ((1R)-2-cyclopropyl-1-{[(2S)-3-phenyl-2-({[4-(quinolin-3-yloxy)phenyl]sulfonyl}amino)propanoyl]amino}ethyl)boronic acid citrate ester |
| 25-A | ((1R)-1-{[(2S)-2-({[4-(1,3-benzothiazol-5-yloxy)phenyl]sulfonyl}amino)-3-phenylpropanoyl]amino}-2-cyclopropylethyl)boronic acid pinanediol ester |
| 25-B | ((1R)-1-{[(2S)-2-({[4-(1,3-benzothiazol-5-yloxy)phenyl]sulfonyl}amino)-3-phenylpropanoyl]amino}-2-cyclopropylethyl)boronic acid D-mannitol ester |
| 25-C | ((1R)-1-{[(2S)-2-({[4-(1,3-benzothiazol-5-yloxy)phenyl]sulfonyl}amino)-3-phenylpropanoyl]amino}-2-cyclopropylethyl)boronic acid citrate ester |
| 26-A | ((1R)-1-{[(2S)-2-({[4-(1H-benzimidazol-5-yloxy)phenyl]sulfonyl}amino)-3-phenylpropanoyl]amino}-2-cyclopropylethyl)boronic acid pinanediol ester |

TABLE 2-continued

Proteasome Inhibitors

| | |
|---|---|
| 26-B | ((1R)-1-{[(2S)-2-({[4-(1H-benzimidazol-5-yloxy)phenyl]sulfonyl}amino)-3-phenylpropanoyl]amino}-2-cyclopropylethyl)boronic acid D-mannitol ester |
| 26-C | ((1R)-1-{[(2S)-2-({[4-(1H-benzimidazol-5-yloxy)phenyl]sulfonyl}amino)-3-phenylpropanoyl]amino}-2-cyclopropylethyl)boronic acid citrate ester |
| 27-A | ((1R)-2-cyclopropyl-1-{[(2S)-2-({[4-(1H-imidazol-5-yl)phenyl]sufonyl}amino)-3-phenylpropanoyl]amino}ethyl)boronic acid pinanediol ester |
| 27-B | ((1R)-2-cyclopropyl-1-{[(2S)-2-({[4-(1H-imidazol-5-yl)phenyl]sulfonyl}amino)-3-phenylpropanoyl]amino}ethyl)boronic acid D-mannitol ester |
| 27-C | ((1R)-2-cyclopropyl-1-{[(2S)-2-({[4-(1H-imidazol-5-yl)phenyl]sulfonyl}amino)-3-phenylpropanoyl]amino}ethyl)boronic acid citrate ester |
| 28-A | ((1R)-2-cyclopropyl-1-{[(2S)-2-({[4-(1H-indol-5-yloxy)phenyl]sulfonyl}amino)-3-phenylpropanoyl]amino}ethyl)boronic acid pinanediol ester |
| 28-B | ((1R)-2-cyclopropyl-1-{[(2S)-2-({[4-(1H-indol-5-yloxy)phenyl]sulfonyl}amino)-3-phenylpropanoyl]amino}ethyl)boronic acid D-mannitol ester |
| 28-C | ((1R)-2-cyclopropyl-1-{[(2S)-2-({[4-(1H-indol-5-yloxy)phenyl]sulfonyl}amino)-3-phenylpropanoyl]amino}ethyl)boronic acid citrate ester |
| 29-A | {(1R)-2-cyclopropyl-1-[((2S)-2-{[(2-phenoxypyrimidin-5-yl)sulfonyl]amino}-3-phenylpropanoyl)amino]ethyl}boronic acid pinanediol ester |
| 29-B | {(1R)-2-cyclopropyl-1-[((2S)-2-{[(2-phenoxypyrimidin-5-yl)sulfonyl]amino}-3-phenylpropanoyl)amino]ethyl}boronic acid D-mannitol ester |
| 29-C | {(1R)-2-cyclopropyl-1-[((2S)-2-{[(2-phenoxypyrimidin-5-yl)sulfonyl]amino}-3-phenylpropanoyl)amino]ethyl}boronic acid citrate ester |
| 30-A | ((1R)-2-cyclopropyl-1-{[(2S)-3-phenyl-2-({[4-(pyrimidin-2-yloxy)phenyl]sulfonyl}amino)propanoyl]amino}ethyl)boronic acid pinanediol ester |
| 30-B | ((1R)-2-cyclopropyl-1-{[(2S)-3-phenyl-2-({[4-(pyrimidin-2-yloxy)phenyl]sulfonyl}amino)propanoyl]amino}ethyl)boronic acid D-mannitol ester |
| 30-C | ((1R)-2-cyclopropyl-1-{[(2S)-3-phenyl-2-({[4-(pyrimidin-2-yloxy)phenyl]sulfonyl}amino)propanoyl]amino}ethyl)boronic acid citrate ester |
| 31-A | {(1R)-2-cyclopropyl-1-[((2S)-2-{[(5-phenoxypyrazin-2-yl)sulfonyl]amino}-3-phenylpropanoyl)amino]ethyl}boronic acid pinanediol ester |
| 31-B | {(1R)-2-cyclopropyl-1-[((2S)-2-{[(5-phenoxypyrazin-2-yl)sulfonyl]amino}-3-phenylpropanoyl)amino]ethyl}boronic acid D-mannitol ester |
| 31-C | {(1R)-2-cyclopropyl-1-[((2S)-2-{[(5-phenoxypyrazin-2-yl)sulfonyl]amino}-3-phenylpropanoyl)amino]ethyl}boronic acid citrate ester |
| 32-A | ((1R)-2-cyclopropyl-1-{[(2S)-3-phenyl-2-({[4-(pyrazin-2-yloxy)phenyl]sulfonyl}amino)propanoyl]amino}ethyl)boronic acid pinanediol ester |
| 32-B | ((1R)-2-cyclopropyl-1-{[(2S)-3-phenyl-2-({[4-(pyrazin-2-yloxy)phenyl]sulfonyl}amino)propanoyl]amino}ethyl)boronic acid D-mannitol ester |
| 32-C | ((1R)-2-cyclopropyl-1-{[(2S)-3-phenyl-2-({[4-(pyrazin-2-yloxy)phenyl]sulfonyl}amino)propanoyl]amino}ethyl)boronic acid citrate ester |
| 33-A | {(1R)-2-cyclopropyl-1-[((2S)-2-{[(5-phenoxypyridin-2-yl)sulfonyl]amino}-3-phenylpropanoyl)amino]ethyl}boronic acid pinanediol ester |
| 33-B | {(1R)-2-cyclopropyl-1-[((2S)-2-{[(5-phenoxypyridin-2-yl)sulfonyl]amino}-3-phenylpropanoyl)amino]ethyl}boronic acid D-mannitol ester |
| 33-C | {(1R)-2-cyclopropyl-1-[((2S)-2-{[(5-phenoxypyridin-2-yl)sulfonyl]amino}-3-phenylpropanoyl)amino]ethyl}boronic acid citrate ester |

As used herein, the term "boronic acid" refers to a chemical compound containing a —B(OH)$_2$ moiety. In some embodiments, boronic acid compounds can form oligomeric anhydrides by dehydration of the boronic acid moiety. For example, Snyder et al., *J. Am. Chem. Soc.* 80:3611 (1958), reports oligomeric arylboronic acids.

As used herein, the term "boronic acid anhydride" refers to a chemical compound formed by combination of two or more molecules of a boronic acid compound, with loss of one or more water molecules. When mixed with water, the boronic acid anhydride compound is hydrated to release the free boronic acid compound. In various embodiments, the boronic acid anhydride can comprise two, three, four, or more boronic acid units, and can have a cyclic or linear configuration. Non-limiting examples of oligomeric boronic acid anhydrides of peptide boronic acids compound of the invention are illustrated below:

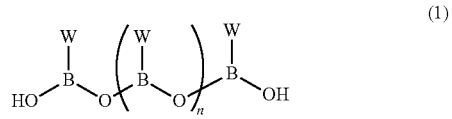

(1)

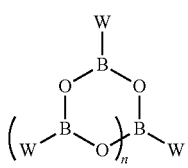

(2)

In formulae (1) and (2) directly above, the variable n is an integer from 0 to about 10, preferably 0, 1, 2, 3, or 4. In some embodiments, the boronic acid anhydride compound comprises a cyclic trimer ("boroxine") of formula (2), wherein n is 1. The variable W has the formula (3):

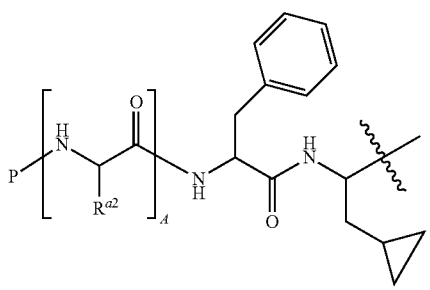

(3)

wherein the variables P, A, and $R^{a2}$ have the values and preferred values described above for formula (I).

In some embodiments, at least 80% of the boronic acid present in the boronic acid anhydride compound exists in a single oligomeric anhydride form. In some embodiments, at least 85%, 90%, 95%, or 99% of the boronic acid present in the boronic acid anhydride compound exists in a single oligomeric anhydride form. In certain preferred embodiments, the boronic acid anhydride compound consists of, or consists essentially of, a boroxine having formula (3).

The boronic acid anhydride compound preferably can be prepared from the corresponding boronic acid by exposure to dehydrating conditions, including, but not limited to, recrystallization, lyophilization, exposure to heat, and/or exposure to a drying agent. Nonlimiting examples of suitable recrystallization solvents include ethyl acetate, dichloromethane, hexanes, ether, acetonitrile, ethanol, and mixtures thereof.

In some embodiments, $Z^1$ and $Z^2$ together form a moiety derived from a boronic acid complexing agent. For purposes of the invention, the term "boronic acid complexing agent" refers to any compound having at least two functional groups, each of which can form a covalent bond with boron. Nonlimiting examples of suitable functional groups include amino, hydroxyl, and carboxyl. In some embodiments, at least one of the functional groups is a hydroxyl group. The term "moiety derived from a boronic acid complexing agent" refers to a moiety formed by removing the hydrogen atoms from two functional groups of a boronic acid complexing agent.

As used herein, the terms "boronate ester" and "boronic ester" are used interchangeably and refer to a chemical compound containing a —$B(Z^1)(Z^2)$ moiety, wherein at least one of $Z^1$ or $Z^2$ is alkoxy, aralkoxy, or aryloxy; or $Z^1$ and $Z^2$ together form a moiety derived from a boronic acid complexing agent having at least one hydroxyl group.

In the compounds of formulae (I), (I-A), (I-B), and (II), $Z^1$ and $Z^2$ are each independently hydroxy, alkoxy, aryloxy, or aralkoxy; or $Z^1$ and $Z^2$ together form a moiety derived from a boronic acid complexing agent. In some embodiments, $Z^1$ and $Z^2$ are each hydroxy. In some other embodiments, $Z^1$ and $Z^2$ together form a moiety derived from a compound having at least two hydroxyl groups separated by at least two connecting atoms in a chain or ring, said chain or ring comprising carbon atoms and, optionally, a heteroatom or heteroatoms which can be N, S, or O, wherein the atom attached to boron in each case is an oxygen atom.

As employed herein, the term "compound having at least two hydroxyl groups" refers to any compound having two or more hydroxyl groups. For purposes of the invention, the two hydroxyl groups preferably are separated by at least two connecting atoms, preferably from about 2 to about 5 connecting atoms, more preferably 2 or 3 connecting atoms. For convenience, the term "dihydroxy compound" may be used to refer to a compound having at least two hydroxyl groups, as defined above. Thus, as employed herein, the term "dihydroxy compound" is not intended to be limited to compounds having only two hydroxyl groups. The moiety derived from a compound having at least two hydroxyl groups may be attached to boron by the oxygen atoms of any two of its hydroxyl groups. Preferably, the boron atom, the oxygen atoms attached to boron, and the atoms connecting the two oxygen atoms together form a 5- or 6-membered ring.

For purposes of the present invention, the boronic acid complexing agent preferably is pharmaceutically acceptable, i.e., suitable for administration to humans. In some preferred embodiments, the boronic acid complexing agent is a sugar, as described, e.g., in Plamondon et al., WO 02/059131 and Gupta et al., WO 02/059130. The term "sugar" includes any polyhydroxy carbohydrate moiety, including monosaccharides, disaccharides, polysaccharides, sugar alcohols and amino sugars. In some embodiments, the sugar is a monosaccharide, disaccharide, sugar alcohol, or amino sugar. Nonlimiting examples of suitable sugars include glucose, sucrose, fructose, trehalose, mannitol, sorbitol, glucosamine, and N-methylglucosamine. In certain embodiments, the sugar is mannitol or sorbitol. Thus, in the embodiments wherein the sugar is mannitol or sorbitol, $Z^1$ and $Z^2$ together form a moiety of formula $C_6H_{12}O_6$, wherein the oxygen atoms of the two deprotonated hydroxyl groups form covalent attachments with boron to form a boronate ester compound. In certain particular embodiments, $Z^1$ and $Z^2$ together form a moiety derived from D-mannitol.

In some other preferred embodiments, the boronic acid complexing agent is an alpha-hydroxycarboxylic acid or a beta-hydroxycarboxylic acid, as described, e.g., in Elliott et al., WO 09/154,737, herein incorporated by reference. In some such embodiments, the boronic acid complexing agent is selected from the group consisting of glycolic acid, malic acid, hexahydromandelic acid, citric acid, 2-hydroxyisobutyric acid, 3-hydroxybutyric acid, mandelic acid, lactic acid, 2-hydroxy-3,3-dimethylbutyric acid, 2-hydroxy-3-methylbutyric acid, 2-hydroxyisocaproic acid, beta-hydroxyisovaleric acid, salicylic acid, tartaric acid, benzilic acid, glucoheptonic acid, maltonic acid, lactobionic acid, galactaric acid, embonic acid, 1-hydroxy-2-naphthoic acid, and 3-hydroxy-2-naphthoic acid. In certain such embodiments, the boronic acid complexing agent is citric acid.

In certain embodiments, wherein the alpha-hydroxy carboxylic acid or beta-hydroxy carboxylic acid is citric acid, the compound of general formula (I) is characterized by formula (III-A) or (III-B):

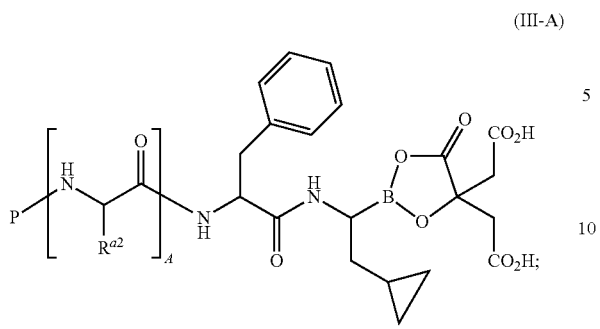
(III-A)

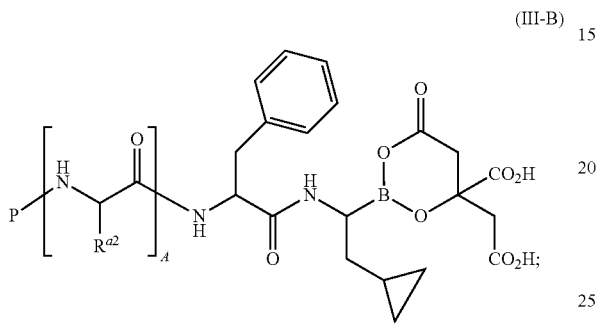
(III-B)

or a mixture thereof, wherein the variables P, A, and $R^{a2}$ have the values described herein.

In certain embodiments, wherein the alpha-hydroxy carboxylic acid or beta-hydroxy carboxylic acid is citric acid, the compound of general formula (I) is characterized by formula (IV-A) or (IV-B):

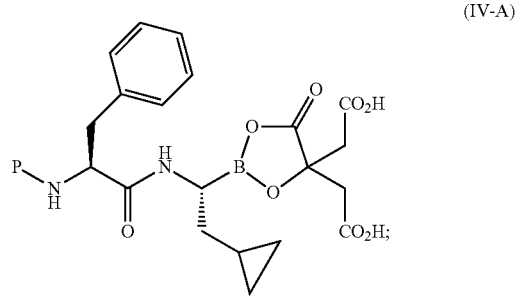
(IV-A)

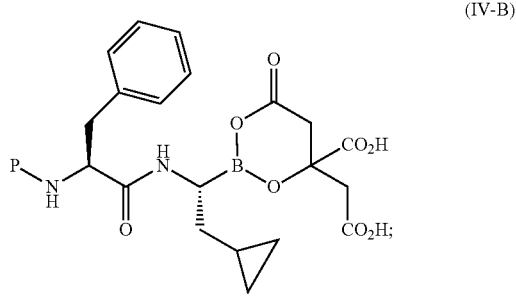
(IV-B)

or a mixture thereof, wherein the variable P has the values described herein.

In certain embodiments, wherein the alpha-hydroxy carboxylic acid or beta-hydroxy carboxylic acid is citric acid, the compound of general formula (I) is characterized by formula (IV-A) or (IV-B):

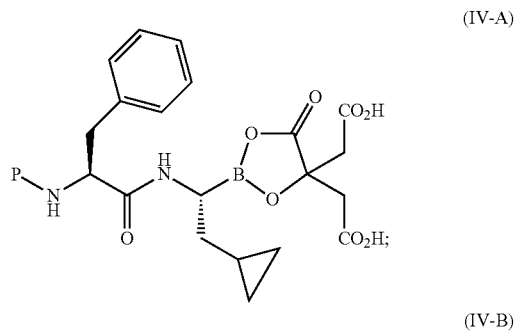
(IV-A)

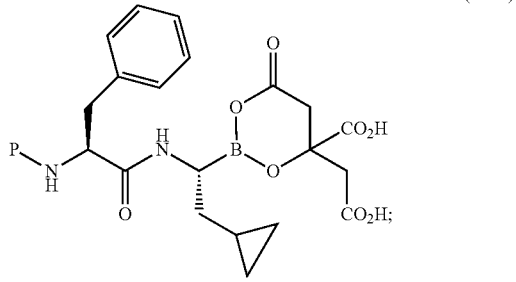
(IV-B)

or a mixture thereof, wherein:
P is $R^D$—$SO_2$—;
$R^D$ is phenyl substituted with 0-1 $R^d$; and
$R^d$ is a substituted or unsubstituted aryl, heteroaryl, heterocyclyl, or cycloaliphatic ring.

In certain such embodiments:
$R^D$ is phenyl substituted with 1 $R^d$;
$R^d$ is substituted or unsubstituted oxazolyl, thiazolyl, or imidazolyl;
wherein if substituted, $R^d$ is substituted with 1 $R^{dd}$; and
$R^{dd}$ is methyl, ethyl, trifluoromethyl, chloro, or fluoro.

In certain embodiments, wherein the alpha-hydroxy carboxylic acid or beta-hydroxy carboxylic acid is citric acid, the compound of general formula (I) is characterized by formula (IV-A) or (IV-B):

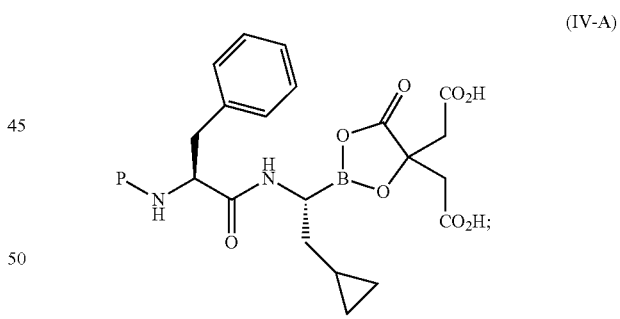
(IV-A)

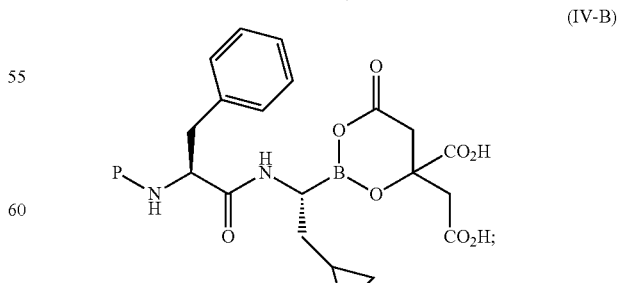
(IV-B)

or a mixture thereof, wherein:
P is $R^D$—$SO_2$—;
$R^D$ is a phenyl substituted with —O—$R^E$;

$R^E$ is a substituted or unsubstituted pyridinyl, pyrazinyl, pyrimidinyl, quinolinyl, benzothiazolyl, benzimidazolyl, or indolyl;

wherein if substituted, $R^E$ is substituted with 1-2 $R^{dd}$; and each $R^{dd}$ is independently $C_{1-4}$ aliphatic, $C_{1-4}$ fluoro-aliphatic, or halo.

In certain such embodiments:

$R^E$ is a substituted or unsubstituted pyridinyl;

wherein if substituted, $R^E$ is substituted with 1 $R^{dd}$; and $R^{dd}$ is methyl, ethyl, trifluoromethyl, chloro, or fluoro.

In certain embodiments, wherein the alpha-hydroxy carboxylic acid or beta-hydroxy carboxylic acid is citric acid, the compound of general formula (I) is characterized by formula (IV-A) or (IV-B):

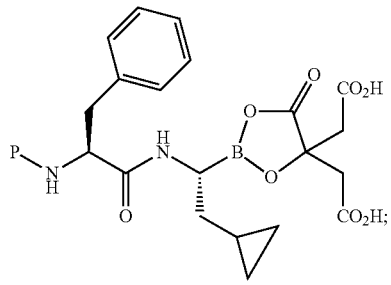

(IV-A)

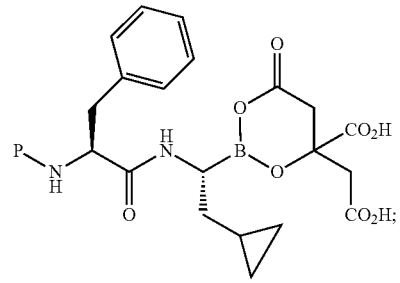

(IV-B)

or a mixture thereof, wherein:
P is $R^D$—$SO_2$—;
$R^D$ is a phenyl substituted with —C(O)—$R^E$;
$R^E$ is a substituted or unsubstituted pyridinyl, pyrazinyl, or pyrimidinyl;
wherein if substituted, $R^E$ is substituted with 1-2 $R^{dd}$; and
each $R^{dd}$ is independently $C_{1-4}$ aliphatic, $C_{1-4}$ fluoro-aliphatic, or halo.

In certain such embodiments:
$R^E$ is a substituted or unsubstituted pyridinyl;
wherein if substituted, $R^E$ is substituted with 1 $R^{dd}$; and
$R^{dd}$ is methyl, ethyl, trifluoromethyl, chloro, or fluoro.

General Synthetic Methodology

The compounds of formula (I) can be prepared by methods known to one of ordinary skill in the art. See, e.g., Adams et al., U.S. Pat. No. 5,780,454; Pickersgill et al., WO 05/097809. An exemplary synthetic route to N-acyl-peptidylboronic acid compounds of the invention (P=$R^c$—C(O)—) is set forth in Scheme 1 below.

Scheme 1

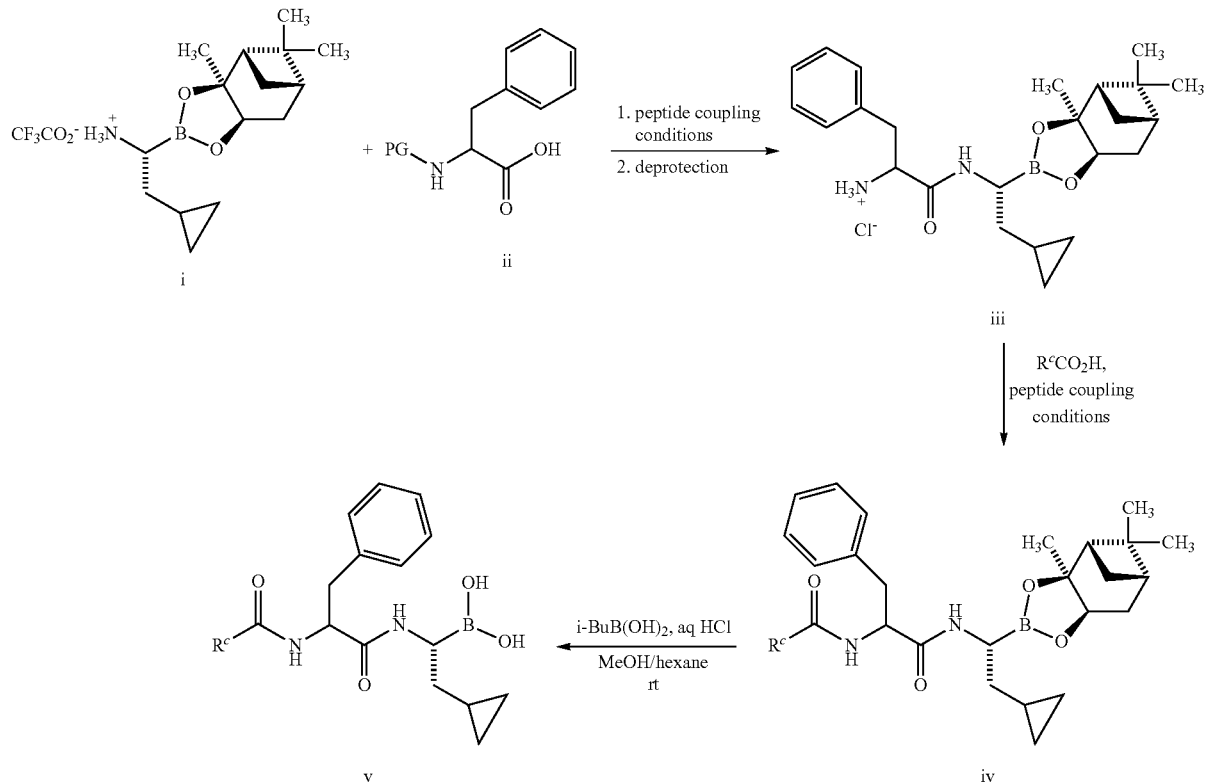

Coupling of compound i with an N-protected amino acid ii, followed by N-terminal deprotection, provides compounds of formula iii. Examples of suitable protecting groups (PG) include, without limitation, acyl protecting groups, e.g., formyl, acetyl (Ac), succinyl (Suc), and methoxysuccinyl; and urethane protecting groups, e.g., tert-butoxycarbonyl (Boc), benzyloxycarbonyl (Cbz), and fluorenylmethoxycarbonyl (Fmoc). The peptide coupling reaction can be conducted by prior conversion of the carboxylic acid moiety of compound ii to an activated ester, e.g., an O-(N-hydroxysuccinnimide) ester, followed by treatment with compound i. Alternatively, the activated ester can be generated in situ by contacting the carboxylic acid of the compound ii with a peptide coupling reagent. Examples of suitable peptide coupling reagents include, without limitation, carbodiimide reagents, e.g., dicyclohexylcarbodiimide (DCC) or 1-(3-dimethylaminopropyl)-3-ethylcarbodiimide (EDC); phosphonium reagents, e.g., benzotriazol-1-yloxytris(dimethylamino)phosphonium hexafluorophosphate (BOP); and uranium reagents, e.g., O-(1H-benzotriazol-1-yl)-N,N,N',N'-tetramthyluronium tetrafluoroborate (TBTU).

Compound iii is then coupled with a carboxylic acid ($R^cCO_2H$) to afford compound iv. The peptide coupling conditions described above for the coupling of compounds i and ii are also suitable for coupling compound iii with $R^cCO_2H$. Deprotection of the boronic acid moiety then affords compound v. The deprotection step preferably is accomplished by transesterification in a biphasic mixture comprising the boronic ester compound iv, an organic boronic acid acceptor, a lower alkanol, a $C_{5-8}$ hydrocarbon solvent, and aqueous mineral acid.

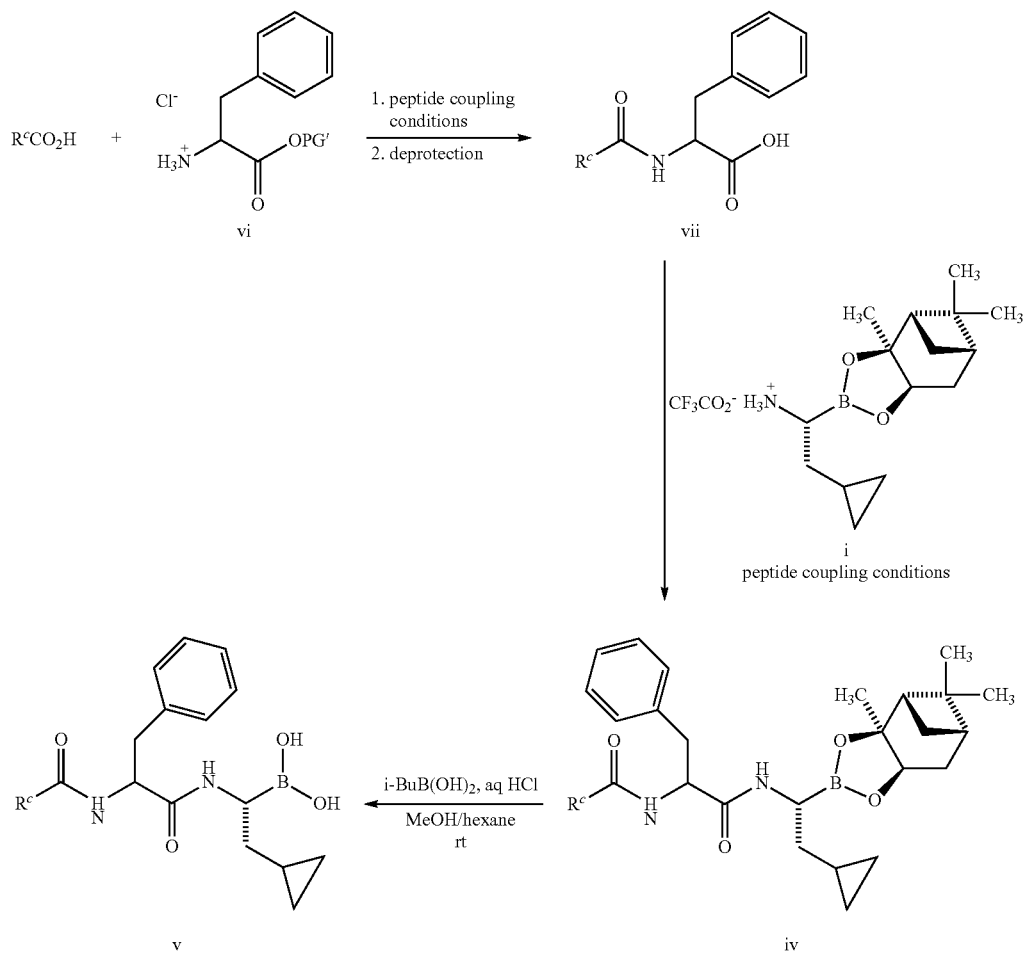

Scheme 2

Alternatively, the order of coupling reactions can be reversed, as shown in Scheme 2. Thus, an O-protected amino acid vi is first coupled with a substituted benzoic acid ($ArCO_2H$), followed by ester hydrolysis, to form compound vii. Coupling with compound i and subsequent boronic acid deprotection are then accomplished as described above for Scheme 1 to afford compound v.

An exemplary synthetic route for preparation of N-sulfonyl-peptidylboronic acid compounds of the invention ($P=R^c-S(O)_2-$) is set forth in Scheme 3 below:

Scheme 3

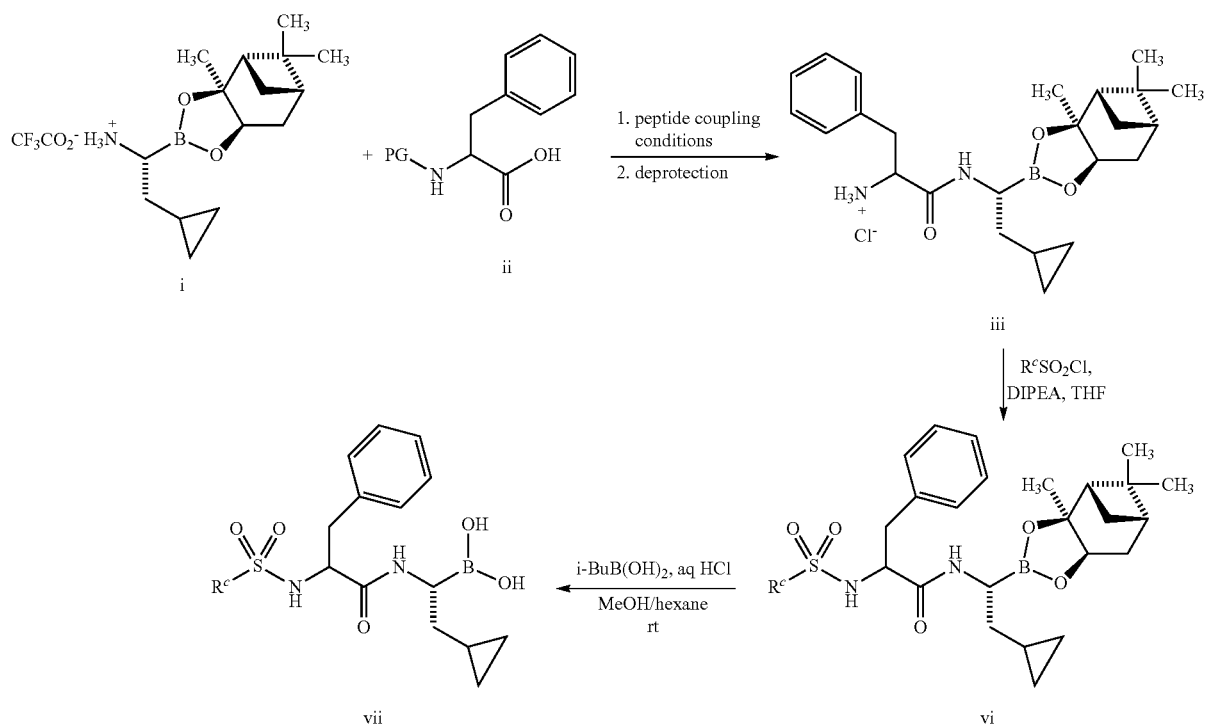

Compound iii, prepared as described above for Scheme 1, is treated with a sulfonyl chloride in the presence of a base such as diisopropylethylamine to afford compound vi. Deprotection of the boronic acid moiety is then accomplished as described above for Scheme 1 to afford compound vii. The order of reactions for preparation of compound vii also can be reversed in a manner analogous to Scheme 2.

Scheme 4

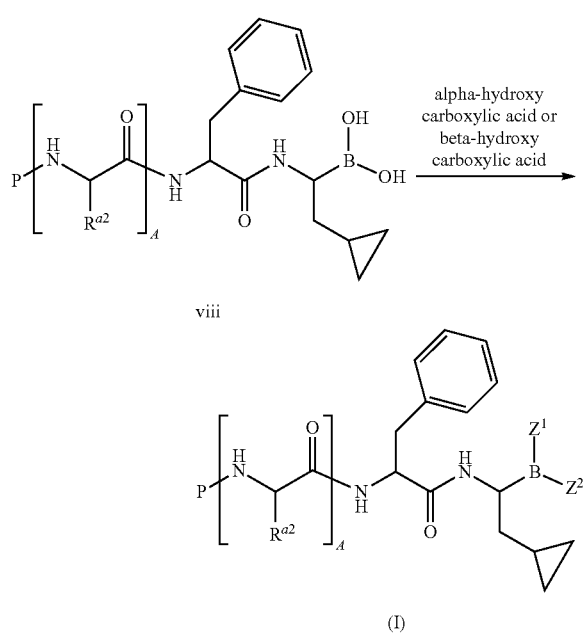

The conversion of viii to the compound of formula (I), wherein $Z^1$ and $Z^2$ together are a moiety derived from an alpha-hydroxy carboxylic acid or a beta-hydroxy carboxylic acid, can be accomplished using esterification conditions employing approximately at least a molar equivalent of the alpha-hydroxy carboxylic acid or beta-hydroxy carboxylic acid in a solvent such as ethyl acetate at a temperature of between about 40° C. and about 80° C. Examples of other suitable solvents for this conversion include, but are not limited to, methyl isobutyl ketone, acetone, acetonitrile, 2-methyltetrahydrofuran, anisole, isopropyl acetate, dimethoxyethane, tetrahydrofuran, dioxane, dichloromethane, toluene, heptane, methylcyclohexane, tert-butyl methyl ether, and mixtures thereof. The choice of the solvent will depend partly on the solubility of the alpha-hydroxy carboxylic acid or beta-hydroxy carboxylic acid used. The temperature selected for the conversion of viii to the compound of formula (I) will depend partly on the boiling point of the solvent or solvent mixture used.

The conversion of viii to the compound of formula (I) wherein $Z^1$ and $Z^2$ together are a moiety derived from an alpha-hydroxy carboxylic acid or a beta-hydroxy carboxylic acid, may be catalyzed by an organic amine base such as, but not limited to, triethylamine, triethylenediamine, pyridine, collidine, 2,6-lutidine, 4-dimethylaminopyridine, di-tertbutylpyridine, N-methylmorpholine, N-methylpiperidine, tetramethylguanidine, diazabicyclo[5.4.0]undec-7-ene (DBU), 1,4-diazabicyclo[2.2.2]octane, 1,5-diazabicycle[4.3.0]non-5-ene, N,N' diisopropylethylamine, or a mixture thereof.

The compound of formula viii and the alpha-hydroxy carboxylic acid or beta-hydroxy carboxylic acid are heated together in the solvent of choice for a period of time. Following this period of time, the reaction mixture is allowed to cool for a period of time and the compound of formula (I) which precipitates upon cooling is collected by filtration. The cooling may be uncontrolled or may be controlled by the use of a cooling apparatus. The reaction mixture may be stirred during this cooling period. Alternatively, the compound of formula (I) can also be isolated from the reaction mixture by cooling followed by evaporation of the solvent. The reaction mixture may be seeded with crystals of the compound of formula (I) in order to effect precipitation.

A co-solvent such as, but not limited to, heptane, methylcyclohexane, toluene, tert-butylmethyl ether, ethyl acetate, or a mixture thereof, may be added during the cooling period. Following the addition of the co-solvent, the reaction mixture can be cooled further leading to the precipitation of the compound of formula (I). Alternatively, once the co-solvent is added, the reaction mixture can then be heated again to generate a homogenous solution, which is then cooled leading to the precipitation of the compound of formula (I). The reaction mixture may be seeded with crystals of the compound of formula (I) in order to effect precipitation.

In some embodiments, the compound of formula (I), wherein $Z^1$ and $Z^2$ together are a moiety derived from an alpha-hydroxy carboxylic acid or a beta-hydroxy carboxylic acid is isolated in crystalline form. In some embodiments, the compound of formula (I) is isolated in substantially crystalline form. In some other embodiments, the compound of formula (I) is isolated in amorphous form.

The compound of formula (I), wherein $Z^1$ and $Z^2$ together are a moiety derived from an alpha-hydroxy carboxylic acid or a beta-hydroxy carboxylic acid, can also be generated by the co-lyophilization of compound viii and the alpha-hydroxy carboxylic acid or beta-hydroxy carboxylic acid. This is accomplished by subjecting an aqueous solution comprising the compound of formula viii and a molar excess of the alpha-hydroxy carboxylic acid or beta-hydroxy carboxylic acid to a lyophilization procedure. In some embodiments, the aqueous solution additionally comprises a water-miscible co-solvent. Examples of suitable co-solvents include, but are not limited to, tert-butyl alcohol, methanol, ethanol, and mixtures thereof. The co-lyophilization results in a composition that contains the compound of formula (I) and the excess alpha-hydroxy carboxylic acid or beta-hydroxy carboxylic acid.

Uses, Formulation, and Administration

The present invention provides compounds that are potent inhibitors of the proteasome. The compounds can be assayed in vitro or in vivo for their ability to inhibit proteasome-mediated peptide hydrolysis or protein degradation.

In another aspect, therefore, the invention provides a method for inhibiting one or more peptidase activities of a proteasome in a cell, comprising contacting a cell in which proteasome inhibition is desired with a compound described herein, or a pharmaceutically acceptable salt, boronic ester, or boronic acid anhydride thereof.

The invention also provides a method for inhibiting cell proliferation, comprising contacting a cell in which such inhibition is desired with a compound described herein. The phrase "inhibiting cell proliferation" is used to denote the ability of a compound of the invention to inhibit cell number or cell growth in contacted cells as compared to cells not contacted with the inhibitor. An assessment of cell proliferation can be made by counting cells using a cell counter or by an assay of cell viability, e.g., an MTT or WST assay. Where the cells are in a solid growth (e.g., a solid tumor or organ), such an assessment of cell proliferation can be made by measuring the growth, e.g., with calipers, and comparing the size of the growth of contacted cells with non-contacted cells.

Preferably, the growth of cells contacted with the inhibitor is retarded by at least about 50% as compared to growth of non-contacted cells. In various embodiments, cell proliferation of contacted cells is inhibited by at least about 75%, at least about 90%, or at least about 95% as compared to non-contacted cells. In some embodiments, the phrase "inhibiting cell proliferation" includes a reduction in the number of contacted cells, as compare to non-contacted cells. Thus, a proteasome inhibitor that inhibits cell proliferation in a contacted cell may induce the contacted cell to undergo growth retardation, to undergo growth arrest, to undergo programmed cell death (i.e., apoptosis), or to undergo necrotic cell death.

In another aspect, the invention provides a pharmaceutical composition comprising a compound of formula (I), or a pharmaceutically acceptable salt or boronic acid anhydride thereof, and a pharmaceutically acceptable carrier.

If a pharmaceutically acceptable salt of the compound of the invention is utilized in these compositions, the salt preferably is derived from an inorganic or organic acid or base. For reviews of suitable salts, see, e.g., Berge et al, *J. Pharm. Sci.* 66:1-19 (1977) and Remington: The Science and Practice of Pharmacy, 20*th Ed.*, ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as lithium, sodium and potassium salts; alkaline earth metal salts, such as calcium and magnesium salts; other multivalent metal salts, such as zinc salts; salts with organic bases, such as dicyclohexylamine, N-methyl-D-glucamine, t-butylamine, ethylene diamine, ethanolamine, and choline; and salts with amino acids such as arginine, lysine, and so forth. In some embodiments, the pharmaceutically acceptable salt is a base addition salt of a boronic acid compound of formula (I), wherein $Z^1$ and $Z^2$ are both hydroxy.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The terms "carrier", "adjuvant", or "vehicle" are used interchangeably herein, and include any and all solvents, diluents, and other liquid vehicles, dispersion or suspension aids, surface active agents, pH modifiers, isotonic agents, thickening or emulsifying agents, preservatives, solid binders, lubricants and the like, as suited to the particular dosage form desired. *Remington: The Science and Practice of Pharmacy, 20th Ed*, ed. A. Gennaro, Lippincott Williams & Wilkins, 2000 discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, carbonates, magnesium hydroxide and aluminum hydroxide, glycine, sorbic acid, or potassium sorbate, partial glyceride mixtures of saturated vegetable fatty acids, water, pyrogen-free water, salts or electrolytes such as protamine sulfate, disodium hydrogen phosphate, potassium hydrogen phosphate, sodium chloride, and zinc salts, colloidal silica, magnesium trisilicate, polyvinyl pyrrolidone, polyacrylates, waxes, polyethylene-polyoxypropylene-block polymers, wool fat, sugars such as lactose, glucose, sucrose, and mannitol, starches such as corn starch and potato starch, cellulose and its derivatives such as sodium carboxymethyl cellulose, ethyl cellulose and cellulose acetate, powdered tragacanth; malt, gelatin, talc, excipients such as cocoa butter and suppository waxes, oils such as peanut oil, cottonseed oil, safflower oil, sesame oil, olive oil, corn oil and soybean oil, glycols such as propylene glycol and polyethylene glycol, esters such as ethyl oleate and ethyl laurate, agar, alginic acid, isotonic saline, Ringer's solution, alcohols such as ethanol, isopropyl alcohol, hexadecyl alcohol, and glycerol, cyclodextrins such as hydroxypropyl β-cyclodextrin and sulfobutylether β-cyclodextrin, lubricants such as sodium lauryl sulfate and magnesium stearate, petroleum hydrocarbons such as mineral oil and petrolatum. Coloring agents, releasing agents, coating agents, sweetening, flavoring and perfuming agents, preservatives and antioxidants can also be present in the composition, according to the judgment of the formulator.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, cyclodextrins, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Compositions formulated for parenteral administration may be injected by bolus injection or by timed push, or may be administered by continuous infusion.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents such as phosphates or carbonates.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In some embodiments, the compound of formula (I) is administered intravenously. In some such embodiments, the compound of formula (I) wherein $Z^1$ and $Z^2$ together form a moiety derived from a boronic acid complexing agent can be prepared in the form of a lyophilized powder, as described in Plamondon et al., WO 02/059131, hereby incorporated by reference in its entirety. In some embodiments, the lyophilized powder also comprises free boronic acid complexing agent. Preferably, the free boronic acid complexing agent and the compound of formula (I) are present in the mixture in a molar ratio ranging from about 0.5:1 to about 100:1, more preferably from about 5:1 to about 100:1. In various embodiments, the lyophilized powder comprises free boronic acid complexing agent and the corresponding boronate ester in a molar ratio ranging from about 10:1 to about 100:1, from about 20:1 to about 100:1, or from about 40:1 to about 100:1.

In some embodiments, the lyophilized powder comprises boronic acid complexing agent and a compound of formula (I), substantially free of other components. However, the composition can further comprise one or more other pharmaceutically acceptable excipients, carriers, diluents, fillers, salts, buffers, bulking agents, stabilizers, solubilizers, and other materials well known in the art. The preparation of pharmaceutically acceptable formulations containing these materials is described in, e.g., *Remington: The Science and Practice of Pharmacy*, 20th Ed., ed. A. Gennaro, Lippincott Williams & Wilkins, 2000, or latest edition. In some embodiments, the pharmaceutical composition comprises a compound of formula (I), a bulking agent, and a buffer.

The lyophilized powder comprising the compound of formula (I) can be prepared according to the procedures described in Plamondon et al., WO 02/059131. Thus, in some embodiments, the method for preparing the lyophilized powder comprises: (a) preparing an aqueous mixture comprising a boronic acid compound of formula (I), wherein $Z^1$ and $Z^2$ are each hydroxy, and a boronic acid complexing agent; and (b) lyophilizing the mixture.

The lyophilized powder preferably is reconstituted by adding an aqueous solvent suitable for pharmaceutical administrations. Examples of suitable reconstitution solvents include, without limitation, water, saline, and phosphate buffered saline (PBS). Preferably, the lyophilized powder is reconstituted with normal (0.9%) saline. Upon reconstitution, an equilibrium is established between a boronate ester compound and the corresponding free boronic acid compound. In some embodiments, equilibrium is reached quickly, e.g., within 10-15 minutes, after the addition of aqueous medium. The relative concentrations of boronate ester and boronic acid present at equilibrium is dependent upon parameters such as, e.g., the pH of the solution, temperature, the nature of the boronic acid complexing agent, and the ratio of boronic acid complexing agent to boronate ester compound present in the lyophilized powder.

The pharmaceutical compositions of the invention preferably are formulated for administration to a patient having, or at risk of developing or experiencing a recurrence of, a proteasome-mediated disorder. The term "patient", as used herein, means an animal, preferably a mammal, more preferably a human. Preferred pharmaceutical compositions of the invention are those formulated for oral, intravenous, or subcutaneous administration. However, any of the above dosage forms containing a therapeutically effective amount of a compound of the invention are well within the bounds of routine experimentation and therefore, well within the scope of the instant invention. In some embodiments, the pharmaceutical composition of the invention may further comprise another therapeutic agent. In some embodiments, such other therapeutic agent is one that is normally administered to patients with the disease or condition being treated.

By "therapeutically effective amount" is meant an amount sufficient to cause a detectable decrease in proteasome activity or the severity of a proteasome-mediated disorder. The amount of proteasome inhibitor needed will depend on the effectiveness of the inhibitor for the given cell type and the length of time required to treat the disorder. It should also be understood that a specific dosage and treatment regimen for any particular patient will depend upon a variety of factors, including the activity of the specific compound employed, the age, body weight, general health, sex, and diet of the patient, time of administration, rate of excretion, drug combinations, the judgment of the treating physician, and the severity of the particular disease being treated. The amount of additional therapeutic agent present in a composition of this invention typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

In another aspect, the invention provides a method for treating a patient having, or at risk of developing or experiencing a recurrence of, a proteasome-mediated disorder. As used herein, the term "proteasome-mediated disorder" includes any disorder, disease or condition which is caused or characterized by an increase in proteasome expression or activity, or which requires proteasome activity. The term "proteasome-mediated disorder" also includes any disorder, disease or condition in which inhibition of proteasome activity is beneficial.

For example, compounds and pharmaceutical compositions of the invention are useful in treatment of disorders mediated via proteins (e.g., NFκB, p27$^{Kip}$, p21$^{WAF/CIP1}$, p53) which are regulated by proteasome activity. Relevant disorders include inflammatory disorders (e.g., rheumatoid arthritis, inflammatory bowel disease, asthma, chronic obstructive pulmonary disease (COPD), osteoarthritis, dermatosis (e.g., atopic dermatitis, psoriasis)), vascular proliferative disorders (e.g., atherosclerosis, restenosis), proliferative ocular disorders (e.g., diabetic retinopathy), benign proliferative disorders (e.g., hemangiomas), autoimmune diseases (e.g., multiple sclerosis, tissue and organ rejection), as well as inflammation associated with infection (e.g., immune responses), neurodegenerative disorders (e.g., Alzheimer's disease, Parkinson's disease, motor neurone disease, neuropathic pain, triplet repeat disorders, astrocytoma, and neurodegeneration as result of alcoholic liver disease), ischemic injury (e.g., stroke), and cachexia (e.g., accelerated muscle protein breakdown that accompanies various physiological and pathological states, (e.g., nerve injury, fasting, fever, acidosis, HIV infection, cancer affliction, and certain endocrinopathies)).

The compounds and pharmaceutical compositions of the invention are particularly useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers. In some embodiments, therefore, the invention provides the compound of formula (I), or a pharmaceutically acceptable salt or boronic acid anhydride thereof, for use in treating cancer. In some embodiments, the invention provides a pharmaceutical composition (as described above) for the treatment of cancer comprising the compound of formula (I), or a pharmaceutically acceptable salt or boronic acid anhydride thereof. In some embodiments, the invention provides the use of the compound of formula (I), or a pharmaceutically acceptable salt or boronic acid anhydride thereof, for the preparation of a pharmaceutical composition (as described above) for the treatment of cancer. In some embodiments, the invention provides the use of an effective amount of the compound of formula (I), or a pharmaceutically acceptable salt or boronic acid anhydride thereof, for the treatment of cancer.

Differences in enzyme kinetics, i.e. the dissociation half-lives, between various proteasome inhibitors may result in differences in tissue distribution of the various inhibitors, which may lead to differences in safety and efficacy profiles. For example, with slowly reversible and irreversible inhibitors a substantial proportion of the molecules may bind to proteasomes in red blood cells, the vascular endothelium, and well-perfused organs such as the liver (i.e. the most 'immediately available' proteasomes in the proximal compartments). These sites might effectively act as a 'sink' for these agents, rapidly binding the molecules and affecting distribution into solid tumors.

Without wishing to be bound by theory, the present inventors believe that compounds that more rapidly dissociate from the proteasome distribute more effectively to tumors, leading to improved antitumor activity. In some embodiments, the invention relates to a method for treating a patient with cancer, comprising administering to the patient a compound of any one of formulas (I), (I-A), (I-B), (II), wherein the compound exhibits a dissociation half-life of less than 60 minutes. In some embodiments, the compound exhibits a dissociation half-life of less than 10 minutes.

Non-limiting examples of solid tumors that can be treated with the disclosed proteasome inhibitors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

Non-limiting examples of hematologic malignancies that can be treated with the disclosed proteasome inhibitors include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); amyloidosis; Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

In some embodiments, the compound or composition of the invention is used to treat a patient having or at risk of developing or experiencing a recurrence in a cancer selected from the group consisting of multiple myeloma, mantle cell lymphoma, follicular lymphoma, amyloidosis, head and neck cancer, soft-tissue sarcoma, non-small cell lung cancer, and prostate cancer. In some embodiments, the compound or composition of the invention is used to treat a patient having or at risk of developing or experiencing a recurrence in a cancer selected from the group consisting of multiple myeloma and mantle cell lymphoma.

In some embodiments, the proteasome inhibitor of the invention is administered in conjunction with another therapeutic agent. The other therapeutic agent may also inhibit the proteasome, or may operate by a different mechanism. In some embodiments, the other therapeutic agent is one that is normally administered to patients with the disease or condition being treated. The proteasome inhibitor of the invention may be administered with the other therapeutic agent in a single dosage form or as a separate dosage form. When administered as a separate dosage form, the other therapeutic agent may be administered prior to, at the same time as, or following administration of the proteasome inhibitor of the invention.

In some embodiments, a proteasome inhibitor of formulas (I), or a pharmaceutically acceptable salt or boronic acid anhydride thereof, is administered in conjunction with an anticancer agent. As used herein, the term "anticancer agent" refers to any agent that is administered to a subject with cancer for purposes of treating the cancer.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

In order that this invention be more fully understood, the following preparative and testing examples are set forth. These examples illustrate how to make or test specific compounds, and are not to be construed as limiting the scope of the invention in any way.

EXAMPLES

| Definitions | |
|---|---|
| ACN | acetonitrile |
| DCM | methylene chloride |
| DIBAL | diisobutylaluminum hydride |
| DIEA | diisopropylethyl amine |
| DMF | dimethylformamide |
| EDCI | N-(3-dimethylaminopropyl)-N'-ethylcarbodiimide hydrochloride |
| EtOAc | ethyl acetate |
| h | hours |
| HATU | N,N,N',N'-tetramethyl-O-(7-azabenzotriazole-1-yl)uronium hexafluorophosphate |
| HOBt | 1-hydroxybenztriazole hydrate |
| HPLC | high performance liquid chromatography |
| LCMS | liquid chromatography mass spectrum |
| LHMDS | lithium hexamethyldisilazide |
| min | minutes |
| NMM | 4-methylmorpholine |
| $R_t$ | retention time from diode array spectra |
| TBTU | o-benzotriazol-1-yl-N,N,N',N'-tetramethyluronium tetrafluoroborate |
| TFA | trifluoroacetic acid |
| THF | tetrahydrofuran |
| TLC | thin layer chromatography |

Analytical LCMS Methods

LCMS Conditions

Analyses of boronic acids were run on a Waters Symmetry C18 3.5u 4.6×100 mm ID column using the following gradient:

Solvent A: 1% acetonitrile, 99% water, 0.1% formic acid

Solvent B: 95% acetonitrile, 5% water, 0.1% formic acid

| Time | A [%] | B [%] | Flow [ml/min] |
|---|---|---|---|
| 0.0 | 95.0 | 5.0 | 1.0 |
| 7.5 | 0.0 | 100.0 | 1.0 |
| 9.8 | 0.0 | 100.0 | 1.0 |
| 9.8 | 95.0 | 5.0 | 1.0 |
| 10.0 | 95.0 | 5.0 | 1.0 |

Spectra of intermediates were run on a Hewlett-Packard HP1100 using the following conditions:

Formic Acid: Phenominex Luna 5 μm C18 50×4.6 mm column at 2.5 ml/min gradient of ACN containing 0 to 100 percent 0.1% Formic Acid in $H_2O$ for 3 min Ammonium Acetate: Phenominex Luna 5 μm C18 50×4.6 mm column at 2.5 ml/min gradient of ACN containing 0 to 100 percent 10 mM Ammonium Acetate in $H_2O$ for 3 min.

Example 1

Intermediate 7

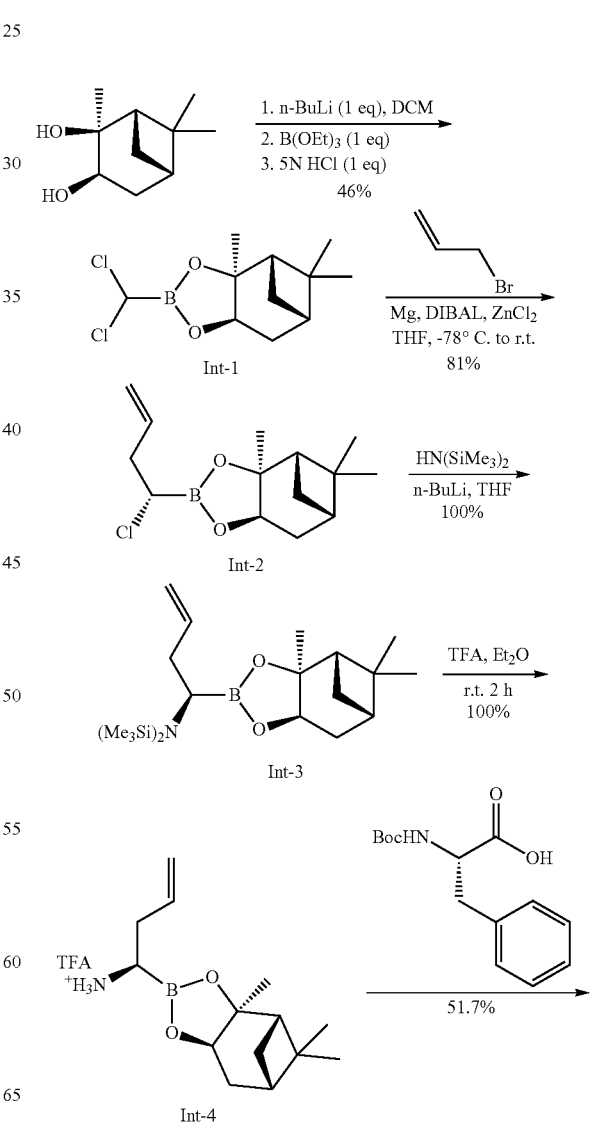

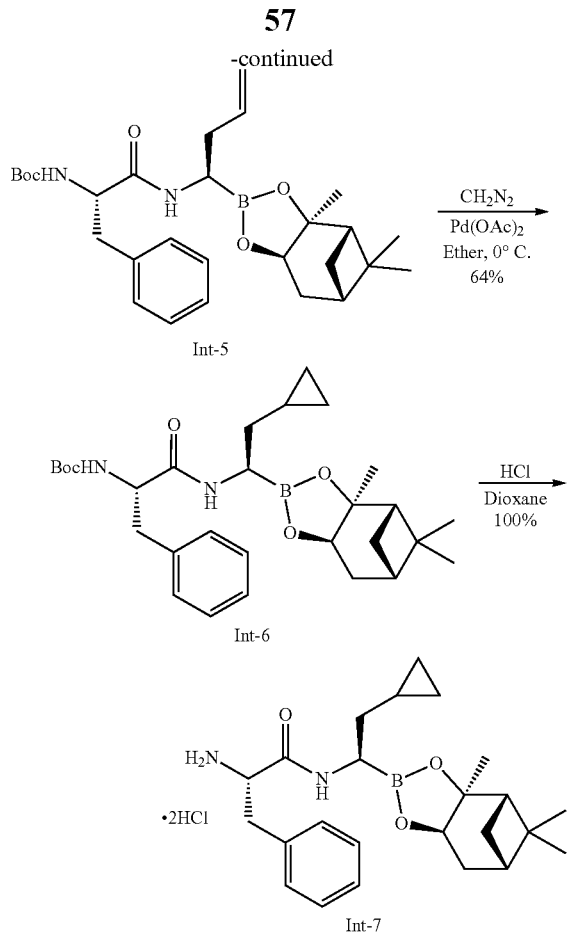

Step 1: (3aS,4S,6S)-2-(dichloromethyl)-3a,5,5-trimethylhexahydro-4,6-methano-1,3,2-benzodioxaborole Intermediate 1

To a solution of DCM (80 mL, 1.2 mol) in THF (800 mL) at −80° C. to −90° C. was added n-BuLi (2.5 M in hexane, 480 mL, 1.2 mol) under $N_2$, and the reaction mixture was stirred for 1.5 h below −80° C. B(OEt)$_3$ (200 mL, 1.2 mol) was added in one portion and the mixture was stirred for 1 h at −45° C. to −30° C. Aqueous HCl (5 M, 240 mL, 1.2 mol) was then added dropwise while maintaining the temperature below −20° C. and the resulting mixture was stirred at −20° C. for 4 h. The organic layer was separated, and the water layer was extracted with diethyl ether (100 mL×2). The combined organic layers were dried over anhydrous $Na_2SO_4$ and concentrated to give an intermediate. The intermediate was re-dissolved in diethyl ether (800 mL) and pinanediol (188 g, 1.1 mol) was added to the solution. The reaction mixture was stirred overnight at room temperature and then concentrated in vacuo. The residue was purified by column chromatography (petroleum ether:EtOAc 10:1 to 1:1) to afford Intermediate 1 (190 g, 60% yield).

Step 2: Intermediate 2

Allylmagnesium bromide (26.1 mL of 1M in THF) was added to a solution of Intermediate 1 (5.0 g in 60 mL of THF) at −78° C. The solution was stirred for 20 minutes and zinc dichloride (33.25 mL) was added in one portion. The mixture was allowed to warm from −78° C. to room temperature while stirring overnight. The reaction mixture was partitioned between EtOAc and a saturated solution of ammonium chloride. The organic layer was washed with water followed by brine and the solvent removed by roatary evaporation to give Intermediate 2.

Step 3: Intermediate 3

To a solution of LHMDS (1 M in THF, 210 mL, 0.21 mol) at −78° C. was added a solution of Intermediate 2 (51.8 g, 0.19 mol) in THF (500 mL) under $N_2$. The reaction mixture was allowed to warm to room temperature and stirred overnight. The solvent was removed by rotary evaporation and the residue was taken up in diethyl ether/hexanes (1/1; 1 L). The solution was flashed through a pad of silica gel (300 g) and washed with diethyl ether/hexanes (1/1; 500 mL). The solution was concentrated to give Intermediate 3 (75.8 g, 100%) as a colorless oil.

Step 4: Intermediate 4

To a solution of Intermediate 3 (75.8 g, 0.19 mol) in diethyl ether (750 mL) was added 90 mL of TFA dropwise at 0° C. The mixture was allowed to warm to room temperature and stirred for 30 minutes. The solvent was evaporated to give Intermediate 4 (70.1 g, 100% yield) as a white solid.

Step 5: Intermediate 5

To a solution of Intermediate 4 (30.8 g, 0.08 mol) in DCM (1 L) was added HATU (31.58 g, 0.09 mol). The solution was cooled to −45° C. and diisopropylethylamine (54 mL, 0.3 mol) was added dropwise. The mixture was allowed to warm to room temperature and stirred overnight. The reaction mixture was partitioned between EtOAc and water, and the organic layer washed with brine followed by drying over sodium sulfate. Removal of the solvent followed by silica gel chromatography (petroleum ether/EtOAc; 20:1 to 3:1 gradient) gave Intermediate 5 (29 g, 51.7%).

Step 6: Intermediate 6

To a solution of Intermediate 5 (2.0 g, 4.0 mmol) in diethyl ether (200 mL) was added dropwise a solution of diazomethane (6 mmol; prepared from Diazald) in 200 mL of diethyl ether at 0° C. Palladium acetate (42 mg, 0.188 mmol) was added and the mixture stirred until the evolution of nitrogen ceased. The solvent was removed and the product purified by flash chromatography using an EtOAc/petroleum ether gradient (1:10 to 1:5) to give Intermediate 6 (Yield: 1.3 g 64%).

Step 7: Intermediate 7

To a solution of Intermediate 6 (35.0 g, 0.686 mol) in DCM (500 mL) was added 500 mL of 1.37 M HCl in dioxane. The mixture was stirred at room temperature for two hours and the solvent removed by rotary evaporation. The residue was washed with diethyl ether to give Intermediate 7 (Yield 30.0 g, 100%).

Example 2

[(1R)-2-cyclopropyl-1-({(2S)-2-[(isoquinolin-5-yl-sulfonyl)amino]-3-phenylpropanoyl}amino)ethyl]boronic acid Compound 17

Step 1: Compound 17-A (Procedure A)

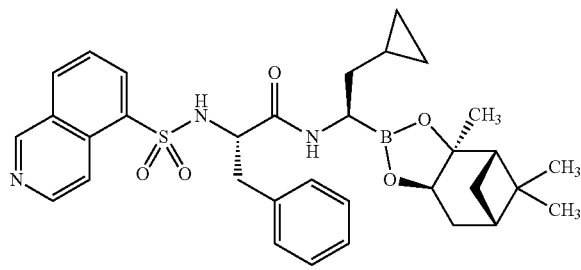 [SMILES: CC1(C)[C@@H]2C[C@H]3OB([C@H](CC4CC4)NC(=O)[C@H](Cc4ccccc4)NS(=O)(=O)c4cccc5cnccc45)O[C@@]3(C)[C@H]1C2]

To a 250 mL flask was added Intermediate 7 (0.5 g, 1.1 mmol), THF (13 mL), diisopropylethylamine (0.5 mL, 3.5 mmol) and isoquinoline-5-sulfonyl chloride (250 mg, 1.1 mmol) The mixture was stirred at room temperature overnight, then partitioned between EtOAc and water. The organic layer was washed with brine and then dried over $Na_2SO_4$. The solvent was removed by rotary evaporation and the residue purified by flash chromatography (petroleum ether:EtOAc; 22:1) to give Compound 17-A in 48% yield.

Step 2: [(1R)-2-cyclopropyl-1-({(2S)-2-[(isoquinolin-5-ylsulfonyl)amino]-3-phenylpropanoyl}amino)ethyl]boronic acid Compound 17 (Procedure B)

Compound 17-A (270 mg) was dissolved in 8 mL of methanol along with 135 mg of (2-methylpropyl)boronic acid. To the mixture was added 8 mL of 1N HCl followed by 8 mL of heptane. The mixture was stirred vigorously overnight and the methanol/1N HCl layer was separated and washed with 8 mL of heptane. The methanol/HCl was removed by rotary evaporation and the residue purified by preparative HPLC, resulting in 75 mg (31%) of the title compound. LCMS ($ES^+$—$H_2O$): 450. $^1$H NMR ($CD_3OD$, 400 MHz, δ): 9.29 (s, 1H), 8.5 (d, 1H), 8.32 (m, 3H), 7.7 (m, 1H), 6.7-6.9 (m, 5H), 4.15 (m, 1H), 3.0 (m, 1H), 2.7 (m, 2H), 1.39 (m, 1H), 1.18 (m, 1H), 0.7 (m, 1H), 0.42 (m, 2H), 0.0 (m, 2H).

Example 3

D-Mannitol ester of [(1R)-2-cyclopropyl-1-({(2S)-2-[(isoquinolin-5-ylsulfonyl)amino]-3-phenylpropanoyl}amino)ethyl]boronic acid Compound 17-B (Procedure C)

To the above product [(1R)-2-cyclopropyl-1-({(2S)-2-[(isoquinolin-5-ylsulfonyl)amino]-3-phenylpropanoyl}amino)ethyl]boronic acid (70 mg, 0.149 mmol) was added tert-butyl alcohol (8 mL), water (8 mL) and D-mannitol (510 mg, 2.98 mmol). The solution was frozen at −78° C. and placed on lypholizer for 40 h. The resulting {(1R)-1[((2S)-2-{[(2S)-2-(acetylamino)-4-phenylbutanoyl]amino}-3-phenylpropanoyl)amino]-2-cyclobutylethyl} boronic acid.20[$C_6H_{14}O_6$] was obtained as 580 mg (100% yield) of a white powder.

Example 4

Additional N-sulfonyl-peptidylboronic Acid Compounds

The following compounds were prepared by procedures A and B analogous to those described in Example 2 above using the appropriate sulfonyl chloride. $^1$H NMR data is described below. All compounds were also converted to the corresponding D-mannitol esters using Procedure C as described above in Example 3.

| Compound | $^1$H NMR (Bruker 400 mHz) |
|---|---|
| 8 | $^1$H NMR ($^6$D DMSO, 400 MHz, δ): 8.41 (s, 1H), 7.94 (m, 1H), 7.71 (s, 1H), 7.59 (m, 2H), 7.42 (m, 1H), 7.2-7.4 (m, 6H), 6.95 (m, 1H), 6.55 (d, 1H), 4.22 (m, 1H), 3.19 (m, 1H), 2.97 (m, 1H), 2.85 (m, 1H), 2.21 (br s, 2H), 1.59 (m, 1H), 1.20 (m, 1H), 0.88 (m, 1H), 0.42 (m, 1H), 0.05 (m, 1H). |
| 4 | $^1$H NMR ($CD_3OD$, 400 MHz, δ): 9.5 (s, 1H), 8.40 (s, 1H), 8.10 (d, 1H), 7.82 (d, 1H), 7.02 (m, 5H), 4.29 (m, 1H), 3.02 (m, 1H), 2.88 (m, 1H), 2.49 (m, 1H), 1.78 (m, 1H), 1.02 (m, 1H), 0.60 (m, 1H), 0.39 (m, 2H), 0.0 (m, 2H). |
| 6 | $^1$H NMR ($CD_3OD$, 400 MHz, δ): 8.50 (s, 1H), 7.8-8.0 (m, 5H), 7.2-7.4 (m, 5H), 4.38 (m, 1H), 3.16 (m, 1H), 3.0 (m, 1H), 2.65 (m, 1H), 1.4 (m, 1H), 1.2 (m, 1H), 0.72, (m, 1H), 0.49 (m, 2H), 0.0 (m, 2H). |
| 13 | $^1$H NMR ($CD_3OD$, 400 MHz, δ): 7.8 (d, 1H), 7.5 (s, 1H), 7.2 (m, 5H), 7.05 (d, 1H), 4.7 (br s, 2H), 4.25 (m, 1H), 3.30 (s, 3H), 3.12 (m, 1H), 2.90 (m, 1H), 2.62 (m, 1H), 1.35 (m, 1H), 1.15 (m, 1H), 0.7 (m, 1H), 0.45 (m, 2H), 0.0 (m, 2H). |
| 1 | $^1$H NMR ($CD_3OD$, 400 MHz, δ): 8.30 (d, 1H), 8.0 (m, 1H), 7.80 (m, 2H), 7.2-7.4 (m, 9H), 4.25 (m, 1H), 3.25 (m, 1H), 2.99 (m, 1H), 2.71 (m, 1H), 1.39 (m, 1H), 1.21 (m, 1H), 0.69 (m, 1H), 0.48 (m, 2H), 0.0 (m, 2H). |
| 15 | $^1$H NMR ($CD_3OD$, 400 MHz, δ): 7.5 (s, 1H), 7.22 (m, 5H), 6.89 (s, 1H), 4.70 (s, 2H), 4.3 (m, 1H), 3.15 (m, 1H), 2.99 (m, 1H), 2.75 (m, 1H), 1.40 (m, 1H), 1.20 (m, 1H), 0.7 (m, 1H), 0.50 (m, 2H), 0.0 (m, 2H). |
| 7 | $^1$H NMR ($CD_3OD$, 400 MHz, δ): 8.50 (s, 1H), 8.2 (m, 1H), 7.80 (m, 2H), 7.1-7.3 (m, 8H), 4.30 (m, 1H), 3.25 (m, 1H), 3.0 (m, 1H), 2.75 (m, 1H), 1.4 (m, 1H), 1.20 (m, 1H), 0.65 (m, 1H), 0.5 (m, 2H), 0.0 (m, 2H). |

-continued

| Compound | ¹H NMR (Bruker 400 mHz) |
|---|---|
| 16 | ¹H NMR (CD₃OD, 400 MHz, δ): 8.8 (d, 1H), 8.5 (s, 1H), 8.35 (d, 1H), 8.25 (m, 2H), 8.05 (d, 1H), 7.75 (m, 2H), 7.21 (m, 5H), 4.35 (m, 1H), 3.25 (m, 1H), 2.98 (m, 1H), 2.65 (m, 1H), 1.39 (m, 1H), 1.1 (m, 1H), 0.65 (m, 1H), 0.5 (m, 2H), 0.0 (m, 2H). |
| 2 | ¹H NMR (CD₃OD, 400 MHz, δ) 8.49 (d, 2H), 7.65 (s, 2H), 7.55 (m, 4H), 7.20 m, 5H), 6.98 (d, 2H), 4.25 (m, 1H), 3.25 (m, 1H), 2.99 (m, 1H), 2.70 (m, 1H), 1.38 (m, 1H), 1.21 (m, 1H), 0.70 (m, 1H), 0.49 (m, 2H), 0.0 (m, 2H). |
| 14 | ¹H NMR (CD₃OD, 400 MHz, δ) 8.50 (d, 2H), 7.85 (d, 2H), 7.2-7.4 (m, 9H), 4.25 (m, 1H), 3.25 (m, 1H), 2.99 (m, 1H), 2.70 (m, 1H), 1.38 (m, 1H), 1.21 (m, 1H), 0.70 (m, 1H), 0.49 (m, 2H), 0.0 (m, 2H). |
| 5 | ¹H NMR (CD₃OD, 400 MHz, δ): 8.40 (s, 1H), 8.25 (m, 1H), 7.98 (s, 1H), 7.88 (m, 1H), 7.70 (m, 1H), 7.25 (m, 5H), 4.45 (m, 1H), 3.25 (m, 1H), 3.05 (m, 1H), 2.97 (s, 3H), 2.60 (m, 1H), 1.40 (m, 1H), 1.15 (m, 1H), 0.65 (m, 1H), 0.49 (m, 2H), 0.0 (m, 2H). |
| 10 | ¹H NMR (CD₃OD, 400 MHz, δ): 7.7 (d, 1H), 7.55 (d, 1H), 7.35 (s, 1H), 7.22 (m, 1H), 7.02 (m, 3H), 6.8 (m, 3H), 4.22 (m, 1H), 3.9 (s, 3H), 2.95 (m, 1H), 2.65 (m, 1H), 2.5 (m, 1H), 1.35 (m, 1H), 0.97 (m, 1H), 0.55 (m, 1H), 0.39 (m, 2H), 0.0 (m, 2H). |
| 3 | ¹H NMR (CD₃OD, 400 MHz, δ): 8.49 (s, 1H), 7.7 (d, 1H), 7.2-7.4 (m, 5H), 6.75 (d, 1H), 4.25 (m, 1H), 3.85 (m, 4H), 3.75 (m, 4H), 3.12 (m, 1H), 2.95 (m, 1H), 2.54 (m, 1H), 1.38 (m, 1H), 1.22 (m, 1H), 0.69 (m, 1H), 0.47 (m, 2H), 0.0 (m, 2H). |

Example 5

[(1R)-2-cyclopropyl-1-({(2S)-3-phenyl-2-[(pyrazin-2-ylcarbonyl)amino]propanoyl}amino)ethyl]boronic acid Compound 12

Step 1: N-[(1S)-1-benzyl-2-({(1R)-2-cyclopropyl-1-[(3aS,4S,6S,7aR)-3a,5,5-trimethylhexahydro-4,6-methano-1,3,2-benzodioxaborol-2-yl]ethyl}amino)-2-oxoethyl]pyrazine-2-carboxamide Compound 12-A (Procedure D)

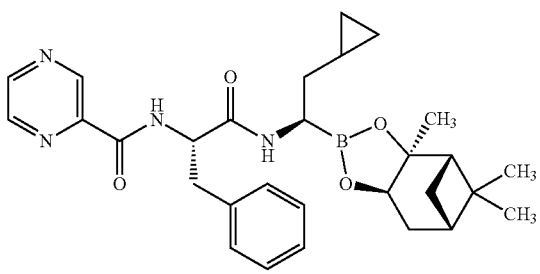 [SMILES: CC1(C)[C@@H]2C[C@H]3OB([C@H](CC4CC4)NC(=O)[C@H](Cc4ccccc4)NC(=O)c4cnccn4)O[C@@]3(C)[C@H]1C2]

Intermediate 7 (0.053 g, 0.11 mmol) was dissolved in 1 mL of DMF along with pyrazine-2-carboxylic acid (0.12 mmol), TBTU (0.13 mmol), and diisopropylethylamine (96 μL). The mixture was stirred at room temperature overnight and then partitioned between DCM and 1N NaOH. The organic layer was washed with water and the solvent removed by rotary evaporation to give 0.047 g of Compound 12-A which was used without purification in the following step.

Step 2: [(1R)-2-cyclopropyl-1-({(2S)-3-phenyl-2-[(pyrazin-2-ylcarbonyl)amino]propanoyl}amino) ethyl]boronic acid Compound 12 (Procedure B)

The title compound was prepared from Compound 12-A using procedure B as described above in Example 2. The title compound was purified by preparative TLC on silica gel plates using 1:9 methanol:DCM as eluent (Yield: 0.0039 g, 15%). The title compound showed a single peak by LCMS with the expected MW of 382 (ES⁻) and 365 (ES⁺ minus H₂O). Compound 12 was converted to its mannitol ester Compound 12-B following procedure C as described in Example 3 above.

Example 6

[(1R)-2-cyclopropyl-1-({(2S)-2-[(2,5-dichlorobenzoyl)amino]-3-phenylpropanoyl}amino)ethyl]boronic acid Compound 9

Step 1: N-[(1S)-1-benzyl-2-({(1R)-2-cyclopropyl-1-[(3aS,4S,6S,7aR)-3a,5,5-trimethylhexahydro-4,6-methano-1,3,2-benzodioxaborol-2-yl]ethyl}amino)-2-oxoethyl]-2,5-dichlorobenzamide Compound 9-A (Procedure D)

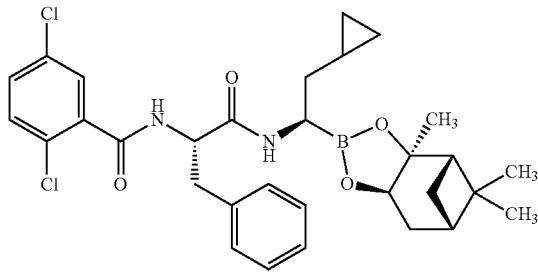 [SMILES: CC1(C)[C@@H]2C[C@H]3OB([C@H](CC4CC4)NC(=O)[C@H](Cc4ccccc4)NC(=O)c4cc(Cl)ccc4Cl)O[C@@]3(C)[C@H]1C2]

Intermediate 7 (0.053 g, 0.11 mmol) was dissolved in 1 mL of DMF along with 2,5-dichlorobenzoic acid (0.12 mmol), TBTU (0.13 mmol), and diisopropylethylamine (96 μL). The mixture was stirred at room temperature overnight and then partitioned between DCM and 1N NaOH. The organic layer was washed with water and the solvent removed by rotary evaporation to give 0.050 g (78%) of Compound 9-A which was used without purification in the following step.

Step 2: [(1R)-2-cyclopropyl-1-({(2S)-2-[(2,5-dichlorobenzoyl)amino]-3-phenylpropanoyl}amino)ethyl] boronic acid Compound 9 (Procedure B)

The title compound was prepared from Compound 9-A using procedure B as described above in Example 2. The title compound was purified by preparative TLC on silica gel plates using 1:9 methanol:DCM as eluent (Yield: 0.0073 g, 24%). The title compound showed a single peak by LCMS with the expected MW of 448 (ES) and 431 (ES$^+$ minus H$_2$O). Compound 9 was converted to its mannitol ester Compound 9-B following procedure C as described in Example 3 above.

Example 7

Citrate Ester (Procedure E)

The boronic acid of formula (I), where $Z^1$ and $Z^2$ are hydroxy groups (1.62 mmol) or a corresponding amount of the boronic acid anhydride is dissolved in acetone (30 mL, 0.4 mol) at room temperature. Citric acid monohydrate (0.340 g, 0.00162 mol) is dissolved in acetone (5 mL), and is then added to the solution of the boronic acid. The flask containing residual citric acid is rinsed into the reaction mixture with an additional 5 mL of acetone. The reaction mixture is stirred at room temperature for 5 minutes and then the acetone is removed by rotary evaporation. The resulting solid is dried under vacuum for two days.

Procedure E can also be performed using acetonitrile as the solvent instead of acetone.

Example 8

20S Proteasome Assay

β5 Selective substrate: To 1 µL of test compound dissolved in DMSO in a 384-well black microtiter plate is added 25 µL of assay buffer at 37° C. containing human PA28 activator (Boston Biochem, 12 nM final) with Ac-WLA-AMC (β5 selective substrate) (15 µM final), followed by 25 µL of assay buffer at 37° C. containing human 20S proteasome (Boston Biochem, 0.25 nM final). Assay buffer is composed of 20 mM HEPES, 0.5 mM EDTA and 0.01% BSA, pH7.4. The reaction is followed on a BMG Galaxy plate reader (37° C., excitation 380 nm, emission 460 nm, gain 20). Percent inhibition is calculated relative to 0% inhibition (DMSO) and 100% inhibition (10 µM bortezomib) controls. Compound of formula (I) are typically tested in this assay as their mannitol esters (prepared as described above). The mannitol esters are hydrolyzed to the free active boronic acid species.

β1 Selective substrate: To 1 µL of test compound dissolved in DMSO in a 384-well microtiter plate is added 25 µL of assay buffer at 37° C. containing human PA28 activator (Boston Biochem, 12 nM final) with Z-LLE-AMC (β1 selective substrate) (15 µM final), followed by 25 µL of assay buffer at 37° C. containing human 20S proteasome (Boston Biochem, 0.25 nM final). Assay buffer is composed of 20 mM HEPES, 0.5 mM EDTA and 0.01% BSA, pH7.4. The reaction is followed on a BMG Galaxy plate reader (37° C., excitation 380 nm, emission 460 nm, gain 20). Percent inhibition is calculated relative to 0% inhibition (DMSO) and 100% inhibition (10 µM bortezomib) controls. Compound of formula (I) are typically tested in this assay as their mannitol esters (prepared as described above). The mannitol esters are hydrolyzed to the free active boronic acid species.

When tested in this assay, Compounds 1, 2, 4, 6, 7, 9, and 12-17 showed the percentage inhibition values listed in Table 3 below.

TABLE 3

Percentage Inhibition in 20S Proteasome Assay

| Compound | Concentration (µM) | Inhibition β1 (%) | Concentration (µM) | Inhibition β5 (%) |
|---|---|---|---|---|
| 1 | 0.41 | 67.2 | 0.41 | 91.8 |
| 2 | 0.41 | 70.7 | 0.41 | 89 |
| 4 | 0.41 | 73.2 | 0.41 | 89.8 |
| 6 | 0.41 | 65.4 | 0.41 | 92.9 |
| 7 | 0.41 | 81.3 | 0.41 | 93 |
| 9 | 0.33 | 91.1 | 0.41 | 93.3 |
| 12 | 0.33 | 93 | 0.41 | 81.9 |
| 13 | 0.41 | 66.7 | 0.41 | 83.7 |
| 14 | 0.41 | 75.7 | 0.41 | 93.1 |
| 15 | 0.41 | 77.1 | 0.41 | 90.3 |
| 16 | 0.41 | 82.7 | 0.41 | 90.8 |
| 17 | 0.41 | 71.9 | 0.41 | 89.7 |

Example 9

Proteasome Inhibition Kinetics

Enzyme kinetic parameters including dissociation constants and half lives were determined by analysis of enzyme progress curves as follows:

Proteasome inactivation measurements were obtained by monitoring individual progress curves for the hydrolysis of the site-specific fluorogenic 7-amido-4-methylcoumarin (AMC)-labeled peptide substrates (β5, Suc-LLVY-AMC; β2, Z-VLR-AMC, and β1, Z-LLE-AMC) at different inhibitor concentrations. Cleavage of the fluorogenic peptide was continuously monitored as a change in the fluorescence emission at 460 nm ($\lambda_{ex}$=360 nm) and plotted as a function of time. All assays were performed in cuvettes with 2 mL of 50 mM HEPES (pH 7.5), 0.5 mM EDTA, at 37±0.2° C., and with continuous stirring. The concentrations of substrates varied from 10 to 25 µM (<½ $K_M$). The concentration of human 20S proteasome was 0.25 nM and was activated with 0.01% SDS. The rate constant, $k_{obs}$, describing the conversion from the initial velocity to the steady state velocity, were estimated by nonlinear least-squares regression analysis of the individual progress curves using the equation for time-dependent or slow-binding inhibition:

$$F = v_s t + \frac{v_i - v_s}{k_{obs}}[1 - \exp(-k_{obs}t)]$$

where F is fluorescence, $v_i$ and $v_s$ are the initial and steady state velocities of the reaction in the presence of inhibitor, and t is time. A plot of $k_{obs}$ as a function of [I] was made to obtain $k_{on}$ from the slope of the linear fit of the data. The apparent dissociation constant, $K^{app}_i$, was determined by nonlinear least-fit of the fractional velocity, $v_s/v_o$, as a function of [I], were $v_s$ is the steady state value obtained from the time-dependent or slow-binding equation and $v_o$ is the initial velocity in the absence of inhibitor:

$$\frac{v_s}{v_o} = \frac{1}{1 + \frac{[I]}{K_i^{app}}}$$

The dissociation constant $K_i$, was calculated from the apparent Ki using the following expression:

$$K_i = \frac{K_i^{app}}{1 + \frac{[S]}{K_m}}$$

The off rate, $k_{off}$, was mathematically calculated from the above determined parameters using the following relationship:

$$K_i = \frac{k_{off}}{k_{on}}$$

The half-life was then determined from the $k_{off}$ value using the following relationship:

$$t_{1/2} = \frac{\ln 2}{k_{off}}$$

Using this protocol, dissociation half-lives were determined for Compounds 1, 2, 5, 6, 7, 14, and 16. Compounds 1, 2, 6, and 7 exhibited a $t_{1/2}$ less than 10 min. Compounds 5, 14, and 16 exhibited a $t_{1/2}$ greater than 10 minutes and less than 60 minutes.

Example 10

Antiproliferation Assay

HCT-116 (1000) or other tumor cells in 100 μL of appropriate cell culture medium (McCoy's 5A for HCT-116, Invitrogen) supplemented with 10% fetal bovine serum (Invitrogen) are seeded in wells of a 96-well cell culture plate and incubated overnight at 37° C. Test compounds are added to the wells and the plates are incubated for 96 hours at 37° C. MTT or WST reagent (10 μL, Roche) are added to each well and incubated for 4 hours at 37° C. as described by the manufacturer. For MTT the metabolized dye is solubilized overnight according to manufacturer's instructions (Roche). The optical density for each well is read at 595 nm (primary) and 690 nm (reference) for the MTT and 450 nm for the WST using a spectrophotometer (Molecular Devices). For the MTT the reference optical density values are subtracted from the values of the primary wavelength. Percent inhibition is calculated using the values from a DMSO control set to 100%.

Example 11

In Vivo Tumor Efficacy Model

Freshly dissociated HCT-116 ($2-5\times10^6$), WSU-DLCL2 ($2-5\times10^6$), or other tumor cells in 100 μL of RPMI-1640 media (Sigma-Aldrich) are aseptically injected into the subcutaneous space in the right dorsal flank of female CD-1 nude mice (age 5-8 weeks, Charles River) using a 1 mL 26⅜-ga needle (Becton Dickinson Ref #309625). Alternatively, some xenograft models (e.g., CWR22) require the serial passaging of tumor fragments. In these cases, small fragments of tumor tissue (approximately 1 mm³) are implanted subcutaneously in the right dorsal flank of anesthetized (3-5% isoflourane/oxygen mixture) C.B-17/SCID mice (age 5-8 weeks, Charles River) via a 13-ga trocar (Popper & Sons 7927). Beginning at day 7 after inoculation tumors are measured twice weekly using a vernier caliper. Tumor volumes are calculated using standard procedures (0.5×(length×width²)). When the tumors reach a volume of approximately 200 mm³ mice are randomized into treatment groups and begin receiving drug treatment. Dosing and schedules are determined for each experiment based on previous results obtained from pharmacokinetic/pharmacodynamic and maximum tolerated dose studies. The control group will receive vehicle without any drug. Typically, test compound (100-200 μL) is administered via intravenous (27-ga needle), oral (20-ga gavage needle) or subcutaneous (27-ga needle) routes at various doses and schedules. Tumor size and body weight are measured twice a week and the study is terminated when the control tumors reach approximately 2000 mm³.

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

What is claimed is:

1. A method of treating proteasome proliferative disorders comprising administrating to a patient in need of such treatment a compound of formula (I):

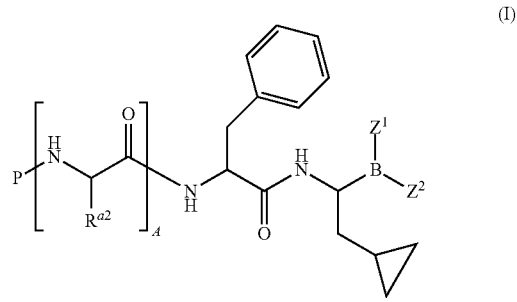

or a pharmaceutically acceptable salt or boronic acid anhydride thereof, wherein:

A is 0, 1, or 2;

P is hydrogen or an amino-group-blocking moiety;

each $R^{a2}$ independently is hydrogen, $C_{1-6}$ aliphatic, $C_{1-6}$ fluoroaliphatic, $-(CH_2)_m-CH_2-R^B$, $-(CH_2)_m-CH_2-NHC(=NR^4)NH-Y$, $-(CH_2)_m-CH_2-CON$ $(R^4)_2$, —$(CH_2)_m$—$CH_2$—$N(R^4)CON(R^4)_2$, —$(CH_2)_m$—$CH(R^6)N(R^4)_2$, —$(CH_2)_m$—$CH(R^5)$—$OR^5$, or —$(CH_2)_m$—$CH(R^5)$—$SR^5$;

each Y independently is hydrogen, —CN, —$NO_2$, or —$S(O)_2$—$R^{10}$;

each $R^B$ independently is a substituted or unsubstituted mono- or bicyclic ring system;

each $R^4$ independently is hydrogen or a substituted or unsubstituted aliphatic, aryl, heteroaryl, or heterocyclyl group; or two $R^4$ on the same nitrogen atom, taken together with the nitrogen atom, form a substituted or unsubstituted 4- to 8-membered heterocyclyl ring having, in addition to the nitrogen atom, 0-2 ring heteroatoms independently selected from N, O, and S;

each $R^5$ independently is hydrogen or a substituted or unsubstituted aliphatic, aryl, heteroaryl, or heterocyclyl group;

each $R^6$ independently is a substituted or unsubstituted aliphatic, aryl, or heteroaryl group;

each $R^{10}$ independently is $C_{1-6}$ aliphatic, $C_{6-10}$ aryl, or —$N(R^4)_2$;

m is 0, 1, or 2; and $Z^1$ and $Z^2$ are each independently hydroxy, alkoxy, aryloxy, or aralkoxy; or $Z^1$ and $Z^2$ together form a moiety derived from a boronic acid complexing agent.

2. The method of claim 1, wherein P is $R^c$—C(O)—, $R^c$—O—C(O)—, $R^c$—$N(R^{4c})$—C(O)—, $R^c$—$S(O)_2$—, or $R^c$—$N(R^{4c})$—$S(O)_2$—;

$R^c$ is selected from the group consisting of $C_{1-6}$ aliphatic, $C_{1-6}$ fluoroaliphatic, —$R^D$, -$T^1$-$R^D$, and -$T^1$-$R^{2c}$;

$T^1$ is a $C_{1-6}$ alkylene chain substituted with 0-2 independently selected $R^{3a}$ or $R^{3b}$, wherein the alkylene chain optionally is interrupted by —$C(R^5)$=$C(R^5)$—, —C≡C—, or —O—;

$R^D$ is a substituted or unsubstituted monocyclic, bicyclic or tricyclic ring system;

$R^{2c}$ is halo, —$OR^5$, —$SR^6$, —$S(O)R^6$, —$SO_2R^6$, —$SO_2N(R^4)_2$, —$N(R^4)_2$, —$NR^4C(O)R^5$, —$NR^4C(O)N(R^4)_2$, —$NR^4CO_2R^6$, —$N(R^4)SO_2R^6$, —$N(R^4)SO_2N(R^4)_2$, —O—$C(O)R^5$, —$OC(O)N(R^4)_2$, —$C(O)R^5$, —$CO_2R^5$, or —$C(O)N(R^4)_2$;

each $R^{3a}$ independently is selected from the group consisting of —F, —OH, —O($C_{1-4}$ alkyl), —CN, —$N(R^4)_2$, —C(O)($C_{1-4}$ alkyl), —$CO_2H$, —$CO_2(C_{1-4}$ alkyl), —C(O)—$NH_2$, and —C(O)—$NH(C_{1-4}$ alkyl);

each $R^{3b}$ independently is a $C_{1-3}$ aliphatic substituted or unsubstituted with $R^{3a}$ or $R^7$;

each $R^7$ is a substituted or unsubstituted aromatic group; and $R^{4c}$ is hydrogen, $C_{1-4}$ alkyl, $C_{1-4}$ fluoroalkyl, or $C_{6-10}$ ar($C_{1-4}$)alkyl, the aryl portion of which is substituted or unsubstituted.

3. The method of claim 2, characterized by formula (I-B):

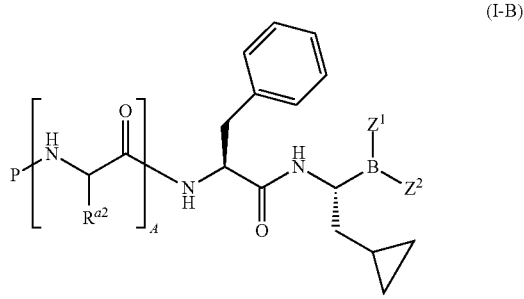

(I-B)

or a pharmaceutically acceptable salt or boronic acid anhydride thereof.

4. The method of claim 3, wherein A is 0.

5. The method of claim 3, wherein each $R^{a2}$ is independently $C_{1-6}$ aliphatic, $C_{1-6}$ fluoroaliphatic, or —$(CH_2)_m$—$CH_2$—$R^B$, and m is 0 or 1.

6. The method of claim 5, wherein $R^B$ is a substituted or unsubstituted phenyl.

7. The method of claim 3, wherein $R^D$ is substituted on substitutable ring carbon atoms with 0-2 $R^d$ and 0-2 $R^{8d}$;

each $R^d$ independently is selected from the group consisting of $C_{1-6}$ aliphatic, $C_{1-6}$ fluoroaliphatic, halo, —$R^{1d}$, —$R^{2d}$, -$T^2$-$R^{1d}$, -$T^2$-$R^{2d}$;

$T^2$ is a $C_{1-6}$ alkylene chain substituted with 0-2 independently selected $R^{3a}$ or $R^{3b}$, wherein the alkylene chain optionally is interrupted by —$C(R^5)$=$C(R^5)$—, —C≡C—, or —O—;

each $R^{1d}$ independently is a substituted or unsubstituted aryl, heteroaryl, heterocyclyl, or cycloaliphatic ring;

each $R^{2d}$ independently is —$NO_2$, —CN, —$C(R^5)$=$C(R^5)_2$, —C≡C—$R^5$, —$OR^5$, —$SR^6$, —$S(O)R^6$, —$SO_2R^6$, —$SO_2N(R^4)_2$, —$N(R^4)_2$, —$NR^4C(O)R^5$, —$NR^4C(O)N(R^4)_2$, —$N(R^4)C(=NR^4)$—$N(R^4)_2$, —$N(R^4)C(=NR^4)$—$R^6$, —$NR^4CO_2R^6$, —$N(R^4)SO_2R^6$, —$N(R^4)SO_2N(R^4)_2$, —O—$C(O)R^5$, —$OC(O)N(R^4)_2$, —$C(O)R^5$, —$CO_2R^5$, —$C(O)N(R^4)_2$, —$C(O)N(R^4)$—$OR^5$, —$C(O)N(R^4)C(=NR^4)$—$N(R^4)_2$, —$N(R^4)C(=NR^4)$—$N(R^4)$—$C(O)R^5$, or —$C(=NR^4)$—$N(R^4)_2$;

each $R^{3a}$ independently is selected from the group consisting of —F, —OH, —O($C_{1-4}$ alkyl), —CN, —$N(R^4)_2$, —C(O)($C_{1-4}$ alkyl), —$CO_2H$, —$CO_2(C_{1-4}$ alkyl), —C(O)$NH_2$, and —C(O)$NH(C_{1-4}$ alkyl);

each $R^{3b}$ independently is a $C_{1-3}$ aliphatic substituted or unsubstituted with $R^{3a}$ or $R^7$, or two substituents $R^{3b}$ on the same carbon atom, taken together with the carbon atom to which they are attached, form a 3- to 6-membered cycloaliphatic ring;

each $R^7$ independently is a substituted or unsubstituted aryl or heteroaryl ring;

each $R^{8d}$ independently is selected from the group consisting of $C_{1-4}$ aliphatic, $C_{1-4}$ fluoroaliphatic, halo, —OH, —O($C_{1-4}$ aliphatic), —$NH_2$, —$NH(C_{1-4}$ aliphatic), and —$N(C_{1-4}$ aliphatic)$_2$; and each substitutable ring nitrogen atom in $R^D$ is unsubstituted or is substituted with —$C(O)R^5$, —$C(O)N(R^4)_2$, —$CO_2R^6$, —$SO_2R^6$, —$SO_2N(R^4)_2$, $C_{1-4}$ aliphatic, a substituted or unsubstituted $C_{6-10}$ aryl, or a $C_{6-10}$ ar($C_{1-4}$)alkyl, the aryl portion of which is substituted or unsubstituted.

8. The method of claim 3, wherein:

each saturated ring carbon atom in $R^D$ is unsubstituted or is substituted with =O, $R^d$ or $R^{8d}$;

each unsaturated ring carbon atom in $R^D$ is unsubstituted or is substituted with $R^d$ or $R^{8d}$;

each $R^d$ independently is selected from the group consisting of $C_{1-6}$ aliphatic, $C_{1-6}$ fluoroaliphatic, halo, —$R^{1d}$, —$R^{2d}$, -$T^2$-$R^{1d}$, -$T^2$-$R^{2d}$;

$T^2$ is a $C_{1-6}$ alkylene chain substituted with 0-2 independently selected $R^{3a}$ or $R^{3b}$, wherein the alkylene chain optionally is interrupted by —$C(R^5)$=$C(R^5)$—, —C≡C—, or —O—;

each $R^{1d}$ independently is a substituted or unsubstituted aryl, heteroaryl, heterocyclyl, or cycloaliphatic ring;

each $R^{2d}$ independently is —$NO_2$, —CN, —$C(R^5)$=$C(R^5)_2$, —C≡C—$R^5$, —$OR^5$, —$SR^6$, —$S(O)R^6$, —$SO_2R^6$, —$SO_2N(R^4)_2$, —$N(R^4)_2$, —$NR^4C(O)R^5$, —$NR^4C(O)N(R^4)_2$, —$N(R^4)C(=NR^4)$—$N(R^4)_2$, —$N(R^4)C(=NR^4)$—$R^6$, —$NR^4CO_2R^6$, —$N(R^4)$ SO$_2$R$^6$, —N(R$^4$)SO$_2$N(R$^4$)$_2$, —O—C(O)R$^5$, —OC(O)N(R$^4$)$_2$, —C(O)R$^5$, —CO$_2$R$^5$, —C(O)N(R$^4$)$_2$, —C(O)N(R$^4$)—OR$^5$, —C(O)N(R$^4$)C(=NR$^4$)—N(R$^4$)$_2$, —N(R$^4$)C(=NR$^4$)—N(R$^4$)—C(O)R$^5$, or —C(=NR$^4$)—N(R$^4$)$_2$;

each R$^{3a}$ independently is selected from the group consisting of —F, —OH, —O(C$_{1-4}$ alkyl), —CN, —N(R$^4$)$_2$, —C(O)(C$_{1-4}$ alkyl), —CO$_2$H, —CO$_2$(C$_{1-4}$ alkyl), —C(O)NH$_2$, and —C(O)NH(C$_{1-4}$ alkyl);

each R$^{3b}$ independently is a C$_{1-3}$ aliphatic substituted or unsubstituted with R$^{3a}$ or R$^7$, or two substituents R$^{3b}$ on the same carbon atom, taken together with the carbon atom to which they are attached, form a 3- to 6-membered cycloaliphatic ring;

each R$^7$ independently is a substituted or unsubstituted aryl or heteroaryl ring;

each R$^{8d}$ independently is selected from the group consisting of C$_{1-4}$ aliphatic, C$_{1-4}$ fluoroaliphatic, halo, —OH, —O(C$_{1-4}$ aliphatic), —NH$_2$, —NH(C$_{1-4}$ aliphatic), and —N(C$_{1-4}$ aliphatic)$_2$; and each substitutable ring nitrogen atom in R$^D$ is unsubstituted or is substituted with —C(O)R$^5$, —C(O)N(R$^4$)$_2$, —CO$_2$R$^6$, —SO$_2$R$^6$, —SO$_2$N(R$^4$)$_2$, C$_{1-4}$ aliphatic, a substituted or unsubstituted C$_{6-10}$ aryl, or a C$_{6-10}$ ar(C$_{1-4}$)alkyl, the aryl portion of which is substituted or unsubstituted.

9. The method of claim 3, wherein R$^D$ is a substituted or unsubstituted monocyclic, bicyclic, or tricyclic ring system selected from the group consisting of phenyl, pyridinyl, pyrimidinyl, pyrazinyl, naphthyl, benzimidazolyl, benzothiazolyl, indolyl, quinolinyl, isoquinolinyl, quinoxalinyl, tetrahydroquinolinyl, tetrahydroisoquinolinyl, tetrahydroquinoxalinyl, oxodihydroindolyl, oxodihydrobenzoxazinyl, dihydrobenzoxazinyl, benzofuropyridyl, pyridoindolyl, and benzofuropyrazinyl.

10. The method of claim 3, characterized by formula (II):

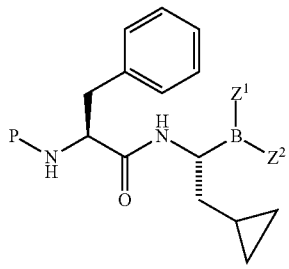

(II)

or a pharmaceutically acceptable salt or boronic acid anhydride thereof, wherein:

P has the formula R$^D$—SO$_2$— or R$^D$—C(O)—;

R$^D$ is a substituted or unsubstituted monocyclic, bicyclic, or tricyclic ring system selected from the group consisting of phenyl, pyridinyl, pyrimidinyl, pyrazinyl, naphthyl, benzimidazolyl, benzothiazolyl, indolyl, quinolinyl, isoquinolinyl, quinoxalinyl, tetrahydroquinolinyl, tetrahydroisoquinolinyl, tetrahydroquinoxalinyl, oxodihydroindolyl, oxodihydrobenzoxazinyl, dihydrobenzoxazinyl, benzofuropyridyl, pyridoindolyl, and benzofuropyrazinyl;

each saturated ring carbon atom in R$^D$ is unsubstituted or is substituted with =O, R$^d$, or R$^{8d}$;

each unsaturated ring carbon atom in R$^D$ is unsubstituted or is substituted with R$^d$ or R$^{8d}$;

each R$^d$ independently is selected from the group consisting of —R$^{1d}$, —R$^{2d}$, -T$^2$-R$^{1d}$, and -T$^2$-R$^{2d}$;

T$^2$ is a C$_{1-3}$ alkylene chain that is unsubstituted or is substituted with R$^{3a}$ or R$^{3b}$;

each R$^{1d}$ independently is a substituted or unsubstituted aryl, heteroaryl, heterocyclyl, or cycloaliphatic ring;

each R$^{2d}$ independently is —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —O—C(O)R$^5$, —OC(O)N(R$^4$)$_2$, —C(O)R$^5$, —CO$_2$R$^5$, or —C(O)N(R$^4$)$_2$; and each R$^{8d}$ independently is selected from the group consisting of C$_{1-4}$ aliphatic, C$_{1-4}$ fluoroaliphatic, halo, —OH, —O(C$_{1-4}$ aliphatic), —NH$_2$, —NH(C$_{1-4}$ aliphatic), and —N(C$_{1-4}$ aliphatic)$_2$.

11. The method of claim 10, wherein R$^d$ has the formula -Q-R$^E$; Q is —O—, —NH—, —S(O)—, —S(O)$_2$—, —C(O)—, or —CH$_2$—; and R$^E$ is a substituted or unsubstituted aryl, heteroaryl, heterocyclyl or cycloaliphatic ring.

12. The method of claim 10, wherein R$^D$ is a phenyl, pyridinyl, pyrazinyl, or pyrimidinyl, which is substituted with a substituent of formula —O—R$^E$, and R$^E$ is a substituted or unsubstituted phenyl, pyridinyl, pyrazinyl, pyrimidinyl, quinolinyl, benzothiazolyl, benzimidazolyl, or indolyl.

13. The method of claim 10, wherein:

R$^D$ is phenyl substituted with 0-1 R$^d$; and

R$^d$ is a substituted or unsubstituted aryl, heteroaryl, heterocyclyl, or cycloaliphatic ring.

14. The method of claim 13, wherein:

P is R$^D$—SO$_2$—;

R$^D$ is phenyl substituted with 1 R$^d$;

R$^d$ is substituted or unsubstituted oxazolyl, thiazolyl, or imidazolyl;

wherein if substituted, R$^d$ is substituted with 1 R$^{dd}$; and

R$^{dd}$ is methyl, ethyl, trifluoromethyl, chloro, or fluoro.

15. The method of claim 10, wherein:

P is R$^D$—SO$_2$—;

R$^D$ is phenyl substituted with —O—R$^E$,

R$^E$ is a substituted or unsubstituted pyridinyl, pyrazinyl, pyrimidinyl, quinolinyl, benzothiazolyl, benzimidazolyl, or indolyl;

wherein if substituted, R$^E$ is substituted with 1-2 occurrences of R$^{dd}$; and each R$^{dd}$ is independently C$_{1-4}$ aliphatic, C$_{1-4}$ fluoroaliphatic, or halo.

16. The method of claim 15, wherein:

R$^E$ is a substituted or unsubstituted pyridinyl;

wherein if substituted, R$^E$ is substituted with 1 occurrence of R$^{dd}$; and

R$^{dd}$ is methyl, ethyl, trifluoromethyl, chloro, or fluoro.

17. The method of claim 10, wherein:

P is R$^D$—SO$_2$—;

R$^D$ is phenyl substituted with —O—R$^E$,

R$^E$ is a substituted or unsubstituted pyridinyl, pyrazinyl, or pyrimidinyl;

wherein if substituted, R$^E$ is substituted with 1-2 occurrences of R$^{dd}$; and each R$^{dd}$ is independently C$_{1-4}$ aliphatic, C$_{1-4}$ fluoroaliphatic, or halo.

18. The method of claim 17, wherein:

R$^E$ is a substituted or unsubstituted pyridinyl;

wherein if substituted, R$^E$ is substituted with 1 occurrence of R$^{dd}$; and

R$^{dd}$ is methyl, ethyl, trifluoromethyl, chloro, or fluoro.

19. The method of claim 1, wherein the compound of formula (I) is selected from

| | |
|---|---|
| 1 | ((1R)-2-cyclopropyl-1-{[(2S)-3-phenyl-2-({[4-(pyridin-2-yloxy)phenyl]sulfonyl}amino)propanoyl]amino}ethyl)boronic acid |
| 2 | ((1R)-2-cyclopropyl-1-{[(2S)-3-phenyl-2-({[4-(pyridin-3-yloxy)phenyl]sulfonyl}amino)propanoyl]amino}ethyl)boronic acid |
| 3 | {(1R)-2-cyclopropyl-1-[((2S)-2-{[(6-morpholin-4-ylpyridin-3-yl)sulfonyl]amino}-3-phenylpropanoyl)amino]ethyl}boronic acid |
| 4 | [(1R)-1-({(2S)-2-[(1,3-benzothiazol-6-ylsulfonyl)amino]-3-phenylpropanoyl}amino)-2-cyclopropylethyl]boronic acid |
| 5 | ((1R)-2-cyclopropyl-1-{[(2S)-2-({[3-(2-methyl-1,3-thiazol-4-yl)phenyl]sulfonyl}amino)-3-phenylpropanoyl]amino}ethyl)boronic acid |
| 6 | ((1R)-2-cyclopropyl-1-{[(2S)-2-({[4-(1,3-oxazol-5-yl)phenyl]sulfonyl}amino)-3-phenylpropanoyl]amino}ethyl)boronic acid |
| 7 | {(1R)-2-cyclopropyl-1-[((2S)-3-phenyl-2-{[(3-{[5-(trifluoromethyl)pyridin-2-yl]oxy}phenyl)sulfonyl]amino}propanoyl)amino]ethyl}boronic acid |
| 8 | {(1R)-2-cyclopropyl-1-[((2S)-2-{[(6-phenoxypyridin-3-yl)sulfonyl]amino}-3-phenylpropanoyl)amino]ethyl}boronic acid |
| 9 | [(1R)-2-cyclopropyl-1-({(2S)-2-[(2,5-dichlorobenzoyl)amino]-3-phenylpropanoyl}amino)ethyl]boronic acid |
| 10 | {(1R)-2-cyclopropyl-1-[((2S)-2-{[(1-methyl-1H-indol-4-yl)sulfonyl]amino}-3-phenylpropanoyl)amino]ethyl}boronic acid |
| 11 | {(1R)-2-cyclopropyl-1-[((2S)-2-{[(4-methyl-3,4-dihydro-2H-1,4-benzoxazin-6-yl)sulfonyl]amino}-3-phenylpropanoyl)amino]ethyl}boronic acid |
| 12 | [(1R)-2-cyclopropyl-1-({(2S)-3-phenyl-2-[(pyrazin-2-ylcarbonyl)amino]propanoyl}amino)ethyl]boronic acid |
| 13 | {(1R)-2-cyclopropyl-1-[((2S)-2-{[(1-methyl-2-oxo-2,3-dihydro-1H-indol-5-yl)sulfonyl]amino}-3-phenylpropanoyl)amino]ethyl}boronic acid |
| 14 | ((1R)-2-cyclopropyl-1-{[(2S)-3-phenyl-2-({[4-(pyridin-4-yloxy)phenyl]sulfonyl}amino)propanoyl]amino}ethyl)boronic acid |
| 15 | {(1R)-1-[((2S)-2-{[(6-chloro-3-oxo-3,4-dihydro-2H-1,4-benzoxazin-7-yl)sulfonyl]amino}-3-phenylpropanoyl)amino]-2-cyclopropylethyl}boronic acid |
| 16 | ((1R)-2-cyclopropyl-1-{[(2S)-3-phenyl-2-({[3-(pyridin-2-ylcarbonyl)phenyl]sulfonyl}amino)propanoyl]amino}ethyl)boronic acid |
| 17 | [(1R)-2-cyclopropyl-1-({(2S)-2-[(isoquinolin-5-ylsulfonyl)amino]-3-phenylpropanoyl}amino)ethyl]boronic acid |
| 18 | ((1R)-2-cyclopropyl-1-{[(2S)-3-phenyl-2-({[4-(pyridin-3-ylsulfinyl)phenyl]sulfonyl}amino)propanoyl]amino}ethyl)boronic acid |
| 19 | ((1R)-2-cyclopropyl-1-{[(2S)-3-phenyl-2-({[4-(pyridin-3-ylsulfonyl)phenyl]sulfonyl}amino)propanoyl]amino}ethyl)boronic acid |
| 20 | ((1R)-2-cyclopropyl-1-{[(2S)-3-phenyl-2-({[4-(pyridin-3-ylamino)phenyl]sulfonyl}amino)propanoyl]amino}ethyl)boronic acid |
| 21 | [(1R)-1-({(2S)-2-[([1]benzofuro[2,3-b]pyridin-6-ylsulfonyl)amino]-3-phenylpropanoyl}amino)-2-cyclopropylethyl]boronic acid |
| 22 | ((1R)-2-cyclopropyl-1-{[(2S)-3-phenyl-2-({[4-(pyridin-2-ylamino)phenyl]sulfonyl}amino)propanoyl]amino}ethyl)boronic acid |
| 23 | ((1R)-2-cyclopropyl-1-{[(2S)-3-phenyl-2-({[4-(pyridin-4-ylamino)phenyl]sulfonyl}amino)propanoyl]amino}ethyl)boronic acid |
| 24 | ((1R)-2-cyclopropyl-1-{[(2S)-3-phenyl-2-({[4-(quinolin-3-yloxy)phenyl]sulfonyl}amino)propanoyl]amino}ethyl)boronic acid |
| 25 | ((1R)-1-{[(2S)-2-({[4-(1,3-benzothiazol-5-yloxy)phenyl]sulfonyl}amino)-3-phenylpropanoyl]amino}-2-cyclopropylethyl)boronic acid |
| 26 | ((1R)-1-{[(2S)-2-({[4-(1H-benzimidazol-5-yloxy)phenyl]sulfonyl}amino)-3-phenylpropanoyl]amino}-2-cyclopropylethyl)boronic acid |
| 27 | ((1R)-2-cyclopropyl-1-{[(2S)-2-({[4-(1H-imidazol-5-yl)phenyl]sulfonyl}amino)-3-phenylpropanoyl]amino}ethyl)boronic acid |
| 28 | ((1R)-2-cyclopropyl-1-{[(2S)-2-({[4-(1H-indol-5-yloxy)phenyl]sulfonyl}amino)-3-phenylpropanoyl]amino}ethyl)boronic acid |
| 29 | {(1R)-2-cyclopropyl-1-[((2S)-2-{[(2-phenoxypyrimidin-5-yl)sulfonyl]amino}-3-phenylpropanoyl)amino]ethyl}boronic acid |
| 30 | ((1R)-2-cyclopropyl-1-{[(2S)-3-phenyl-2-({[4-(pyrimidin-2-yloxy)phenyl]sulfonyl}amino)propanoyl]amino}ethyl)boronic acid |
| 31 | {(1R)-2-cyclopropyl-1-[((2S)-2-{[(5-phenoxypyrazin-2-yl)sulfonyl]amino}-3-phenylpropanoyl)amino]ethyl}boronic acid |
| 32 | ((1R)-2-cyclopropyl-1-{[(2S)-3-phenyl-2-({[4-(pyrazin-2-yloxy)phenyl]sulfonyl}amino)propanoyl]amino}ethyl)boronic acid |
| 33 | {(1R)-2-cyclopropyl-1-[((2S)-2-{[(5-phenoxypyridin-2-yl)sulfonyl]amino}-3-phenylpropanoyl)amino]ethyl}boronic acid. |

20. The method of claim 1, wherein the compound of formula (I) is selected from

| | |
|---|---|
| 1 | ((1R)-2-cyclopropyl-1-{[(2S)-3-phenyl-2-({[4-(pyridin-2-yloxy)phenyl]sulfonyl}amino)propanoyl]amino}ethyl)boronic acid |
| 2 | ((1R)-2-cyclopropyl-1-{[(2S)-3-phenyl-2-({[4-(pyridin-3-yloxy)phenyl]sulfonyl}amino)propanoyl]amino}ethyl)boronic acid |
| 4 | [(1R)-1-({(2S)-2-[(1,3-benzothiazol-6-ylsulfonyl)amino]-3-phenylpropanoyl}amino)-2-cyclopropylethyl]boronic acid |
| 6 | ((1R)-2-cyclopropyl-1-{[(2S)-2-({[4-(1,3-oxazol-5-yl)phenyl]sulfonyl}amino)-3-phenylpropanoyl]amino}ethyl)boronic acid |
| 7 | {(1R)-2-cyclopropyl-1-[((2S)-3-phenyl-2-{[(3-{[5-(trifluoromethyl)pyridin-2-yl]oxy}phenyl)sulfonyl]amino}propanoyl)amino]ethyl}boronic acid |
| 9 | [(1R)-2-cyclopropyl-1-({(2S)-2-[(2,5-dichlorobenzoyl)amino]-3-phenylpropanoyl}amino)ethyl]boronic acid |
| 12 | [(1R)-2-cyclopropyl-1-({(2S)-3-phenyl-2-[(pyrazin-2-ylcarbonyl)amino]propanoyl}amino)ethyl]boronic acid |
| 13 | {(1R)-2-cyclopropyl-1-[((2S)-2-{[(1-methyl-2-oxo-2,3-dihydro-1H-indol-5-yl)sulfonyl]amino}-3-phenylpropanoyl)amino]ethyl}boronic acid |
| 14 | ((1R)-2-cyclopropyl-1-{[(2S)-3-phenyl-2-({[4-(pyridin-4-yloxy)phenyl]sulfonyl}amino)propanoyl]amino}ethyl)boronic acid |
| 15 | {(1R)-1-[((2S)-2-{[(6-chloro-3-oxo-3,4-dihydro-2H-1,4-benzoxazin-7-yl)sulfonyl]amino}-3-phenylpropanoyl)amino]-2-cyclopropylethyl}boronic acid |
| 16 | ((1R)-2-cyclopropyl-1-{[(2S)-3-phenyl-2-({[3-(pyridin-2-ylcarbonyl)phenyl]sulfonyl}amino)propanoyl]amino}ethyl)boronic acid |
| 17 | [(1R)-2-cyclopropyl-1-({(2S)-2-[(isoquinolin-5-ylsulfonyl)amino]-3-phenylpropanoyl}amino)ethyl]boronic acid. |

21. The method of claim 1, wherein the disorder is multiple myeloma, lymphoma, or recurrence of multiple myeloma or lymphoma.

* * * * *